US008062635B2

(12) United States Patent
Hattori et al.

(10) Patent No.: US 8,062,635 B2
(45) Date of Patent: Nov. 22, 2011

(54) BISPECIFIC ANTIBODY SUBSTITUTING FOR FUNCTIONAL PROTEINS

(75) Inventors: Kunihiro Hattori, Shizuoka (JP); Tetsuo Kojima, Shizuoka (JP); Taro Miyazaki, Shizuoka (JP); Tetsuhiro Soeda, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 893 days.

(21) Appl. No.: 10/575,193

(22) PCT Filed: Oct. 8, 2004

(86) PCT No.: PCT/JP2004/014911
§ 371 (c)(1),
(2), (4) Date: Oct. 24, 2006

(87) PCT Pub. No.: WO2005/035756
PCT Pub. Date: Apr. 21, 2005

(65) Prior Publication Data
US 2007/0041978 A1 Feb. 22, 2007

(30) Foreign Application Priority Data

Oct. 10, 2003 (WO) .................. PCT/JP03/13062
Oct. 14, 2003 (WO) .................. PCT/JP03/13123

(51) Int. Cl.
*A61K 39/395* (2006.01)
(52) U.S. Cl. ............... 424/136.1; 424/133.1; 424/145.1; 424/146.1; 424/94.64; 514/13.5; 514/13.7; 514/14.1; 514/14.4
(58) Field of Classification Search .................. None
See application file for complete search history.

(56) References Cited

U.S. PATENT DOCUMENTS

| | | | |
|---|---|---|---|
| 4,208,479 A * | 6/1980 | Zuk et al. ...................... 435/7.9 |
| 4,444,878 A * | 4/1984 | Paulus ........................... 435/7.1 |
| 4,474,893 A | 10/1984 | Reading | |
| 5,496,549 A | 3/1996 | Yamazaki et al. | |
| 5,591,828 A | 1/1997 | Bosslet et al. | |
| 5,744,446 A * | 4/1998 | Lollar et al. ..................... 514/12 |
| 5,945,311 A | 8/1999 | Lindhofer et al. | |
| 6,005,091 A * | 12/1999 | Blackburn et al. ......... 536/23.53 |
| 6,010,902 A | 1/2000 | Ledbetter et al. | |
| 7,033,590 B1 * | 4/2006 | Scheiflinger et al. ...... 424/145.1 |
| 2002/0009430 A1 | 1/2002 | Lindhofer et al. | |
| 2002/0062010 A1 | 5/2002 | Arathoon et al. | |
| 2002/0142374 A1 | 10/2002 | Gallo et al. | |
| 2003/0207346 A1 | 11/2003 | Arathoon et al. | |
| 2005/0130224 A1 | 6/2005 | Saito et al. | |
| 2005/0164307 A1 | 7/2005 | Kojima et al. | |
| 2005/0196397 A1 | 9/2005 | Scheiflinger et al. | |
| 2005/0244416 A1 | 11/2005 | Jung | |
| 2006/0159673 A1 | 7/2006 | Kojima | |
| 2007/0087381 A1 | 4/2007 | Kojima | |
| 2008/0075712 A1 | 3/2008 | Hattori et al. | |
| 2009/0117097 A1 | 5/2009 | Igawa et al. | |
| 2009/0263392 A1 | 10/2009 | Igawa et al. | |
| 2009/0324589 A1 | 12/2009 | Igawa et al. | |
| 2010/0003254 A1 | 1/2010 | Hattori et al. | |
| 2010/0015133 A1 | 1/2010 | Igawa et al. | |
| 2010/0055092 A1 | 3/2010 | Hasegawa et al. | |
| 2011/0076275 A1 | 3/2011 | Igawa et al. | |
| 2011/0111406 A1 | 5/2011 | Igawa et al. | |

FOREIGN PATENT DOCUMENTS

| | | |
|---|---|---|
| AU | 2009290162 | 4/2010 |
| CA | 2 019 559 | 12/1990 |
| CA | 2 603 264 | 10/2006 |
| EP | 0 369 566 | 5/1990 |
| EP | 0 404 097 | 12/1990 |
| EP | 1 505 148 A1 | 2/2005 |
| EP | 1510943 | 3/2005 |
| EP | 0 979 281 | 7/2005 |
| EP | 1 688 488 | 8/2006 |
| EP | 1 693 448 | 8/2006 |
| EP | 1 220 923 | 6/2007 |
| EP | 1870459 | 12/2007 |
| EP | 1 876 236 | 1/2008 |
| EP | 2 275 443 | 1/2011 |
| JP | 2-145187 | 6/1990 |
| JP | 5-501543 | 3/1993 |
| JP | 5-184383 | 7/1993 |
| JP | 5-199894 | 8/1993 |
| JP | 5-203652 | 8/1993 |
| JP | 5-213775 | 8/1993 |
| JP | 5-304992 | 11/1993 |
| JP | 09506001 | 6/1997 |
| JP | 10-165184 | 6/1998 |
| JP | 10-511085 | 10/1998 |
| JP | 11-71288 | 3/1999 |
| JP | 11-506310 | 6/1999 |
| JP | 2001-523971 | 11/2001 |
| JP | 2002-518041 | 6/2002 |

(Continued)

OTHER PUBLICATIONS

Bolton-Maggs et al. The Lancet, 2003, 1801-1809.*
Hsia et al., Am. J. Hematol. 1008, 83:318-320.*
Menegatti et al., Semin Thromb Hemost 2009 35:407-415.*
Bajaj et al., J Biol Chem 1985, 260:11574-11580.*
Bessos et al., Thrombosis Research, 1985, 40:863-867.*
Nilsson et al., 1986, Proc. Natl Acad Sci USA, 83:9169-9173.*
Price et al., Anaesthesia, 2004,59:483-492.*
Rudikoff et al., Proc Natl Acad Sci U S A. Mar. 1982;79(6):1979-83.*
Janeway et al., Immunobiology, 3rd edition, 1997, Garland Press, pp. 3:1 to 3:11.*
William E. Paul, M.D. ed., Fundamental Immunology, 3d ed. 1993, p. 242.*
Portolano et al., J Immunol., 1993, 150:880-887.*
Asselta et al., Semin Thromb Hemost 2009 35:382-389.*

(Continued)

*Primary Examiner* — Michael Szperka
(74) *Attorney, Agent, or Firm* — Fish & Richardson P.C.

(57) ABSTRACT

The present inventors succeeded in constructing bispecific antibodies, which bind to both the blood coagulation factor IX/activated blood coagulation factor IX and blood coagulation factor X, and functionally substitute for blood coagulation factor VIII/activated blood coagulation factor VIII which enhances the enzymatic reaction.

33 Claims, 18 Drawing Sheets

FOREIGN PATENT DOCUMENTS

| | | |
|---|---|---|
| JP | 2003-055398 | 2/2003 |
| JP | 2003-509049 | 3/2003 |
| WO | WO 91/08770 | 6/1991 |
| WO | WO 93/11161 | 6/1993 |
| WO | 9533844 | 12/1995 |
| WO | 9601653 | 1/1996 |
| WO | WO 96/16673 | 6/1996 |
| WO | 9627011 | 9/1996 |
| WO | WO 96/26964 | 9/1996 |
| WO | 9803546 | 1/1998 |
| WO | WO 98/50431 | 11/1998 |
| WO | WO 99/10494 | 3/1999 |
| WO | WO 99/67359 | 12/1999 |
| WO | WO 01/19992 | 3/2001 |
| WO | WO 03/091424 | 1/2003 |
| WO | WO 03/035835 | 5/2003 |
| WO | WO 03/042231 | 5/2003 |
| WO | WO 03/087163 | 10/2003 |
| WO | WO 2004/065611 | 8/2004 |
| WO | WO 2005/035754 | 4/2005 |
| WO | WO 2005/035756 | 4/2005 |
| WO | 2006106905 | 10/2006 |
| WO | WO 2006/106903 | 10/2006 |
| WO | WO 2006/109592 | 10/2006 |
| WO | WO 2007/114325 | 10/2007 |
| WO | WO 2007/142325 | 12/2007 |
| WO | WO 2009/041621 | 4/2009 |
| WO | WO 2009/041643 | 4/2009 |
| WO | WO 2009/125825 | 10/2009 |
| WO | WO 2009/139822 | 11/2009 |
| WO | WO 2010/035769 | 4/2010 |

OTHER PUBLICATIONS

Association of Hemophilia Clinic Directors of Canada, "Hemophilia and Von Willebrand's disease: 2. Management Association of Hemophilia Clinic Directors of Canada", Canadian Medical Association Journal 153(2):147-157, 1995.

Davie et al., "The coagulation cascade: Initiation, maintenance, and regulation", Biochemistry 30(43):10363-10370, 1991.

Grosse-Hovest et al., "A recombinant bispecific single-chain antibody induces targeted, supra-agonistic CD28-stimulation and tumor cell killing", European Journal of Immunology 33(5):1334-1340, 2003.

Lenting et al., "The life cycle of coagulation factor VIII in view of its structure and function", Blood 92(11):3983-3996, 1998.

Piper et al., "Interferon therapy in primary care", Primary Care Update for Ob/Gyns 8(4):163-169, 2001.

Ruef et al., "A bispecific antifibrin-antiplatelet urokinase conjugate (BAAUC) induces enhanced clot lysis and inhibits platelet aggregation", Thombosis and Haemostasis 82(1):109-114, 1999.

Shima et al., "Factor VIII Taitei Kotai (2), Ketsuyubyo A Kanja Katsueki ni okeru in vitro Gyoko Kassei no Kento", Rinsho Ketsueki 46(8):777, 2005 (with English translation).

Soeda et al., "Factor VIII Taitei Kotai (1) Ko FIXa/FX bispecific Kotai no Sakusei oyobi characterization", Rinsho Ketsueki, 46(8):728, 2005 (with English translation).

Soeda et al., "Phage library-ho ni yori Sakusei shita Ko-FIXa/Ko-FX bispecific Kotai no FVIII Taitei Sayo", Japanese Journal of Thrombosis and Hemstasis, 16(5):526, 2005 (with English translation).

Bebbington et al., "High-Level Expression of a Recombinant Antibody from Myeloma Cells Using a Glutamine Synthetase Gene as an Amplifiable Selectable Marker," Biotechnology (N Y), 10:169-175 (1992).

Bos et al., "Enhanced Transfection of a Bacterial Plasmid into Hybridoma Cells by Electroporation: Application for the Selection of Hybrid Hybridoma (Quadroma) Cell Lines," Hybridoma, 11:41-51 (1992).

Brennan et al., "Preparation of Bispecific Antibodies by Chemical Recombination of Monoclonal Immunoglobulin G1 Fragments," Science, 229:81-83 (1985).

Carter, "Bispecific human IgG by design," J. Immunol. Methods, 248:7-15 (2001).

Deng et al., "An Agonist Murine Monoclonal Antibody to the Human c-Mpl Receptor Stimulates Megakaryocytopoiesis," Blood, 92:1981-1988 (1998).

Francois et al., "Construction of a Bispecific Antibody Reacting with the α-and β-Chains of the Human IL-2 Receptor," J. Immunol., 150:4610-4619 (1993).

GenPept Accession No. AAC26541, "anti BoNT/A Hc scFv antibody [synthetic construct]," 1 page (Aug. 1, 2001).

Hämmerling et al., "Use of Hybrid Antibody with Anti-γG and Anti-Ferritin Specificities in Locating Cell Surface Antigens by Electron Microscopy," J. Exp. Med., 128:1461-1473 (1968).

Holliger et al., "'Diabodies': Small bivalent and bispecific antibody fragments," Proc. Natl. Acad. Sci. USA, 90:6444-6448 (1993).

Huse et al., "Generation of a Large Combinatorial Library of the Immunoglobulin Repertoire in Phage Lambda," Science, 246:1275-1281 (1989).

Kang et al., "Linkage of recognition and replication functions by assembling combinatorial antibody Fab libraries along phage surfaces," Proc. Natl. Acad. Sci. USA, 88:4363-4366 (1991).

Karpovsky et al., "Production of Target-Specific Effector Cells Using Hetero—Cross-Linked Aggregates Containing Anti-Target Cell and Anti-Fcγ Receptor Antibodies," J. Exp. Med., 160:1686-1701 (1984).

Kim et al., "Mammalian type I interferon receptors consists of two subunits: IFNaR1 and IFNaR2," Gene, 196:279-286 (1997).

Kroesen et al., "Phase I study of intravenously applied bispecific antibody in renal cell cancer patients receiving subcutaneous interleukin 2," Br. J. Cancer, 70:652-661 (1994).

Kurokawa et al., "Enhanced Fibrinolysis by a Bispecific Monoclonal Antibody Reactive to Fibrin and Tissue Plasminogen Activator," Bio/Technology, 7:1163-1167 (1989).

Lapan et al., "Interaction of the A1 Subunit of Factor VIIIa and the Serine Protease Domain of Factor X Identified by Zero-length Cross-linking," Thromb. Haemost., 80:418-422 (1998).

Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J. Nucl. Med., 34:1662-1671 (1993).

Link et al., "Production and Characterization of a Bispecific IgG Capable of Inducing T-Cell—Mediated Lysis of Malignant B Cells," Blood, 81:3343-3349 (1993).

Löfqvist et al., "Haemophilia prophylaxis in young patients—a long-term follow-up," J. Intern. Med., 241:395-400 (1997).

Lu et al., "Di-diabody: a novel tetravalent bispecific antibody molecule by design," J. Immunol. Methods, 279:219-232 (2003).

Lu et al., "Fab-scFv fusion protein: an efficient approach to production of bispecific antibody fragments," J. Immunol. Methods, 267:213-226 (2002).

Massino et al., "Quantitative analysis of the products of IgG chain recombination in hybrid hybridomas based on affinity chromatography and radioimmunoassay," J. Immunol. Methods, 201:57-66 (1997).

McCafferty et al., "Phage antibodies: filamentous phage displaying antibody variable domains," Nature, 348:552-554 (1990).

Mertens et al., "Factor VIII-Factor IX Interactions: Molecular Sites Involved in Enzyme-Cofactor Complex Assembly," Thromb. Haemost., 82:209-217 (1999).

Milstein et al., "Hybrid hybridomas and their use in immunohistochemistry," Nature, 305:537-540 (1983).

"National Haemophilia Foundation (NHF) Medical and Scientific Advisory Council (MASAC) Recommendations Concerning Prophylaxis," MedicalBulletin, No. 193, 1 page (1994).

Nilsson et al., "Twenty-five years' experience of prophylactic treatment in severe haemophilia A and B," J. Intern. Med., 232:25-32 (1992).

Nitta et al., "Preliminary trial of specific targeting therapy against malignant glioma," Lancet, 335:368-371 (1990).

Ridgway et al., "'Knobs-into-holes' engineering of antibody $C_H3$ domains for heavy chain heterodimerization," Protein Eng., 9:617-621 (1996).

Segal et al., "Introduction: bispecific antibodies," J. Immunol. Methods, 248:1-6 (2001).

Shalaby et al., "Development of Humanized Bispecific Antibodies Reactive with Cytotoxic Lymphocytes and Tumor Cells Overexpressing the HER2 Protooncogene," *J. Exp. Med.*, 175:217-225 (1992).

Stickney et al., "Bifunctional Antibody: A Binary Radiopharmaceutical Delivery System for Imaging Colorectal Carcinoma," *Cancer Res.*, 51:6650-6655 (1991).

Suresh et al., "Advantages of bispecific hybridomas in one-step immunocytochemistry and immunoassays," *Proc. Natl. Acad. Sci. USA*, 83:7989-7993 (1986).

Suresh et al., "Bispecific Monoclonal Antibodies from Hybrid Hybridomas," *Methods Enzymol.*, 121:210-228 (1986).

Taki, *The Journal of Japanese Society on Thrombosis and Hemostasis*, 13:109-113 (2002) (see reference AXX for concise English explanation).

Weiner et al., "A Human Tumor Xenograft Model of Therapy with a Bispecific Monoclonal Antibody Targeting c-*erb*B-2 and CD16," *Cancer Res.*, 53:94-100 (1993).

Weiner et al., "The Role of T Cell Activation in Anti-CD3×Antitumor Bispecific Antibody Therapy," *J. Immunol.*, 152:2385-2392 (1994).

Xiang et al., "Production of Murine V-Human Cr1 Chimeric Anti-TAG72 Antibody Using V Region cDNA Amplified by PCR," *Mol. Immunol.*, 27:809-817 (1990).

European Search Report for App. Ser. No. 06 73 0769, dated Jun. 18, 2009 (8 pages).

Fish & Richardson P.C., Amendment and Response to Restriction Requirement dated Jun. 25, 2009 in U.S. Appl. No. 10/575,905, filed Sep. 25, 2009, 14 pages.

USPTO Restriction Requirement in U.S. Appl. No. 10/575,905, mailed Nov. 18, 2009, 14 pages.

Schmidt et al., Human Physiology, Moscow, 2:431-436 (1996), and English translation: Schmidt et al., "Hemostatis and Coagulation," Human Physiology, R.F. Schmidt, G. Thews (Eds.), Second, Completely Revised Edition, 418-423 [translated by Marguerite A. Biederman-Thorson], Springer-Verlag, 1989.

Schmidt et al., Human Physiology, Moscow, 3:764 (1996), and English translation: Schmidt et al., "Enzymes of the pancreatic juice," Human Physiology, R.F. Schmidt, G. Thews (Eds.), Second, Completely Revised Edition, 716 [translated by Marguerite A. Biederman-Thorson], Springer-Verlag, 1989.

Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," *J. Immunol.*, 157:3250-59 (1996).

USPTO Non-Final Office Action in U.S. Appl. No. 10/575,905, mailed Jun. 23, 2010, 10 pages.

Adams et al., "Humanization of a recombinant monoclonal antibody to produce a therapeutic HER dimerization inhibitor, pertuzumab," Cancer Immunol. Immunother., 55:717-727 (2006).

Binz et al., "Engineering novel binding proteins from nonimmunoglobulin domains," Nat. Biotechnol., 23:1257-68 (2005).

Branden and Tooze, "Recognition of Foreign Molecules by the Immune System," Introduction to Protein Structure, 2d Ed., Garland Publishing, pp. 299-323 (1999).

Comper and Glasgow, "Charge selectivity in kidney ultrafiltration," Kidney Int., 47:1242-51 (1995).

Couto et al., "Anti-BA46 Monoclonal Antibody Mc3: Humanization Using a Novel Positional Consensus and in Vivo and in Vitro Characterization," Cancer Res., 55:1717-22 (1995).

Deen et al., "Structural determinants of glomerular permeability," Am. J. Physiol. Renal. Physiol., 281:F579-F596 (2001).

Del Rio et al., "An Engineered Penicillin Acylase with Altered Surface Charge Is More Stable in Alkaline pH," Ann. NY Acad. Sci., 799:61-64 (1996).

Dillon et al., "Structural and functional characterization of disulfide isoforms of the human IgG2 subclass," J. Biol. Chem., 283(23):16206-15 (2008).

Ewert et al., "Stability improvement of antibodies for extracellular and intracellular applications: CDR grafting to stable frameworks and structure-based framework engineering," Methods, 34:184-199 (2004).

Ghetie and Ward, "FcRn: the MHC class I-related receptor that is more than an IgG transporter," Immunol. Today, 18:592-598 (1997).

Ghetie et al., "Increasing the serum persistence of an IgG fragment by random mutagenesis," Nat. Biotechnol., 15:637-640 (1997).

Ghetie et al., "Multiple roles for the major histocompatibility complex class I-related receptor FcRn," Annu. Rev. Immunol., 18:739-766 (2000).

Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (1998).

Goode et al., "The glomerular basement membrane charge-selectivity barrier: an oversimplified concept?," Nephrol. Dial. Transplant., 11:1714-16 (1996).

Graves et al., "Molecular modeling and preclinical evaluation of the humanized NR-LU-13 antibody," Clin. Cancer Res., 5:899-908 (1999).

Gupta et al., "Affinity chromatography and co-chromatography of bispecific monoclonal antibody immunoconjugates," J. Biochem. Biophys. Methods, 51:203-216 (2002).

Hanson et al., "Catalytic antibodies and their applications," Curr. Opin. Biotechnol., 16:631-636 (2005).

He et al., "Humanization and pharmacokinetics of a monoclonal antibody with specificity for both E- and P-selectin," J. Immunol., 160:1029-35 (1998).

Hinton et al., "An engineered human IgG1 antibody with longer serum half-life," J. Immunol., 176:346-356 (2006).

Ito et al., "The His-probe method: effects of histidine residues introduced into the complementarity-determining regions of antibodies on antigen-antibody interactions at different pH values," FEBS Lett., 309:85-88 (1992).

Kashmiri et al., "Generation, characterization, and in vivo studies of humanized anticarcinoma antibody CC49," Hybridoma, 14:461-473 (1995).

Khawli et al., "Improved tumor localization and radioimaging with chemically modified monoclonal antibodies," Cancer Biother. Radiopharm., 11:203-215 (1996).

Kim et al., "Antibody Engineering for the Development of Therapeutic Antibodies," Mol. Cells, 20:17-29 (2005).

Kim et al., "Chemical modification to reduce renal uptake of disulfide-bonded variable region fragment of anti-tac monoclonal antibody labeled with 99mTc," Bioconjugate Chem., 10:447-453 (1999).

Kim et al., "Lowering of pI by acylation improves the renal uptake of 99mTc-labeled anti-Tac dsFv: effect of different acylating reagents," Nucl. Med. Biol., 29:795-801 (2002).

Kobayashi et al., "The pharmacokinetic characteristics of glycolated humanized anti-Tac Fabs are determined by their isoelectric points," Cancer Res., 59:422-430 (1999).

Kreutz et al., "Efficient bispecific monoclonal antibody purification using gradient thiophilic affinity chromatography," J. Chromatogr. B, 714:161-170 (1998).

Lindhofer et al., "Preferential Species-Restricted Heavy/Light Chain Pairing in Rat/Mouse Quadromas," J. Immunol., 155:219-225 (1995).

Lobo et al., "Antibody pharmacokinetics and pharmacodynamics," J. Pharm. Sci., 93:2645-68 (2004).

Manzke et al., "Single-step purification of bispecific monoclonal antibodies for immunotherapeutic use by hydrophobic interaction chromatography," J. Immunol. Methods, 208:65-73 (1997).

Martin et al., "Crystal structure at 2.8 A of an FcRn/heterodimeric Fc complex: mechanism of pH-dependent binding," Mol. Cell, 7:867-877 (2001).

Marvin et al., "Recombinant approaches to IgG-like bispecific antibodies," Acta. Pharmacol. Sin., 26:649-658 (2005).

Marvin et al., "Redesigning an antibody fragment for faster association with its antigen," Biochemistry, 42:7077-83 (2003).

Merchant et al., "An efficient route to human bispecific IgG," Nat. Biotechnol., 16:677-681 (1998).

Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).

Pavlinkova et al., "Charge-modified single chain antibody constructs of monoclonal antibody CC49: Generation, characterization, pharmacokinetics, and biodistribution analysis," Nucl. Med. Biol., 26:27-34 (1999).

Pavlou et al., "The therapeutic antibodies market to 2008," Eur. J. Pharm. Biopharm., 59:389-396 (2005).

Poduslo et al., "Polyamine modification increases the permeability of proteins at the blood—nerve and blood-brain barriers," J. Neurochem., 66:1599-1609 (1996).

Rajpal et al., a general method for greatly improving the affinity of antibodies by using combinatorial libraries, Proc. Natl. Acad. Sci. USA, 102:8466-71 (2005).

Rathanaswami et al., "Demonstration of an in vivo generated subpicomolar affinity fully human monoclonal antibody to interleukin-8," Biochem. Biophys. Res. Commun., 334:1004-13 (2005).

Reichert et al., "Monoclonal antibody successes in the clinic," Nat. Biotechnol., 23:1073-78 (2005).

Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).

Schaeffer et al. "The Rat Glomerular Filtration Barrier Does Not Show Negative Charge Selectivity," Microcirculation, 9:329-342 (2002).

Segal et al., "Bispecific antibodies in cancer therapy," Curr. Opin. Immunol., 11:558-562 (1999).

Shaul, "Exploring the charge space of protein-protein association: a proteomic study," Proteins, 60:341-352 (2005).

Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001).

Tarditi et al., "Selective high-performance liquid chromatographic purification of bispecific monoclonal antibodies," J. Chromatogr., 599:13-20 (1992).

Ten Kate et al., "Effect of isoelectric point on biodistribution and inflammation: imaging with indium-111-labelled IgG," Eur. J. Nucl. Med., 17:305-309 (1990).

Tsurushita et al., "Design of humanized antibodies: From anti-Tac to Zenapax," Methods, 36:69-83 (2005).

Wu et al., "Development of motavizumab, an ultra-potent antibody for the prevention of respiratory syncytial virus infection in the upper and lower respiratory tract," J. Mol. Biol., 368:652-65 (2007).

Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).

Yang et al., "Tailoring structure-function and pharmacokinetic properties of single-chain Fv proteins by site-specific PEGylation," Protein Eng., 16:761-770 (2003).

Zuckier et al., "Chimeric human-mouse IgG antibodies with shuffled constant region exons demonstrate that multiple domains contribute to in vivo half-life," Cancer Res., 58:3905-08 (1998).

International Search Report for App. Ser. No. PCT/JP2009/057309, mailed Jul. 7, 2009, 8 pages.

USPTO Restriction Requirement in U.S. Appl. No. 12/295,039, dated Oct. 12, 2010, 9 pages.

International Preliminary Report on Patentability for App. Ser. No. PCT/JP2007/057036, dated Oct. 21, 2008, 6 pages.

International Search Report for App. Ser. No. PCT/JP2007/057036, dated May 1, 2007, 2 pages.

European Search Report for App. Ser. No. 07 74 0494, dated Sep. 3, 2009, 3 pages.

Brinkman et al. "Phospholipid-binding domain of factor VIII is involved in endothelial cell-mediated activation of factor X by factor IXa," Arterioscler. Thromb. Vasc. Biol., 22(3):511-516 (2002).

Hoad et al. "Characterization of monoclonal antibodies to human factor X.Xa: Initial observations with a quantitative ELISA procedure," J. Immunol. Methods, 136(2):269-278 (1991).

Okubo et al. "The production and characterization of four monoclonal antibodies to human factor X," Nara Med Assoc., 38(1):20-28 (1987).

Sato et al., "Properties of Two VEGF Receptors, Flt-1 and KDR, in Signal Transduction," Ann N.Y. Acad. Sci, 902:201-207 (May 2000).

Japanese Patent Office, International Search Report for App. Ser. No. PCT/JP2003/013123, mailed Nov. 25, 2003, 4 pages.

Japanese Patent Office, International Preliminary Report on Patentability for App. Ser. No. PCT/JP2003/013123, dated Oct. 20, 2005, 7 pages.

European Search Report for App. Ser. No. EP 03 75 1478, dated Jan. 11, 2008, 3 pages.

International Preliminary Report on Patentability for App. Ser. No. JP2006/306821, dated Oct. 9, 2007, 7 pages.

Japanese Patent Office, International Search Report for App. Ser. No. JP2006/306821, mailed Jul. 11, 2006, 6 pages.

Japanese Patent Office, International Search Report for App. Ser. No. PCT/JP2004/014911, mailed Jan. 25, 2005, 3 pages.

Japanese Patent Office, International Preliminary Report on Patentability for App. Ser. No. PCT/JP2004/014911, 6 pages translation, Jan. 25, 2005.

European Search Report for App. Ser. No. EP 04 79 2180, dated Jan. 17, 2008, 3 pages.

USPTO Restriction Requirement in U.S. Appl. No. 10/575,905, mailed Jun. 25, 2009, 10 pages.

Fish & Richardson P.C., Amendment and Response to Restriction Requirement dated Nov. 18, 2009 in U.S. Appl. No. 10/575,905, filed Apr. 16, 2010, 12 pages.

Fish & Richardson P.C., Amendment in Reply to Action dated Jun. 23, 2010 in U.S. Appl. No. 10/575,905, filed Dec. 22, 2010, 10 pages.

International Preliminary Report on Patentability for App. Ser. No. PCT/JP2009/057309, dated Nov. 30, 2010, 7 pages.

International Preliminary Report on Patentability for App. Ser. No. PCT/JP2007/057058, dated Oct. 21, 2008, 11 pages.

International Search Report App. Ser. No. PCT/JP2007/057058, mailed May 7, 2001, 2 pages.

USPTO Restriction Requirement in U.S. Appl. No. 12/295,075, dated Feb. 22, 2011, 9 pages.

USPTO Final Office Action in U.S. Appl. No. 10/575,905, mailed Feb. 24, 2011, 7 pages.

Panka et al., "Variable region framework differences result in decreased or increased affinity of variant anti-digoxin antibodies," Proc. Natl. Acad. Sci. USA, 85:3080-84 (1988).

Calbiochem® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.

Chamow et al., "A humanized, bispecific immunoadhesin-antibody that retargets CD3+ effectors to kill HIV-1-infected cells," J. Immunol., 153:4268-80 (1994).

USPTO Restriction Requirement in U.S. Appl. No. 11/910,836, dated Mar. 18, 2011, 7 pages.

Fish & Richardson P.C., Response to Restriction Requirement dated Oct. 12, 2010 in U.S. Appl. No. 12/295,039, filed on Apr. 11, 2011, 9 pages.

USPTO Restriction Requirement in U.S. Appl. No. 11/910,128, dated Jun. 9, 2011, 10 pages.

* cited by examiner

FIG. 12

| | | ANTI-F. IXa | | | | | | | | | |
|---|---|---|---|---|---|---|---|---|---|---|---|
| | | A19 | A25 | A31 | A38 | A39 | A40 | A41 | A44 | A50 | A69 | XB12 |
| ANTI-F. X | B2 | | | | | | + | | | | | |
| | B5 | | | | | + | | + | | | | |
| | B9 | | | | | | | | | | | + |
| | B10 | | | | + | + | + | + | | | | + |
| | B11 | | | + | + | + | | + | | + | | + |
| | B12 | | | | + | + | + | + | | | | + |
| | B13 | | | + | | + | + | + | | | | + |
| | B14 | | | | + | + | + | + | | | | + |
| | B15 | | | | | + | | + | | | | + |
| | B16 | | | + | + | + | | + | | | | + |
| | B18 | | | | | | | + | | | | |
| | B19 | | | | | | | | + | | | |
| | B20 | | | | | | | | + | | | |
| | B21 | | | | | | | | | | | |
| | B23 | | | | | | | | | | | |
| | B25 | | | | | | | | | | | |
| | B26 | | + | | | + | | + | + | | + | + |
| | B27 | | | | | + | | + | | | | |
| | B31 | + | | + | + | + | + | + | | | | + |
| | B34-1 | | | | | + | | + | | | | |
| | B34-2 | | | | + | + | + | + | | | | |
| | B35 | | | + | + | + | + | + | | + | | + |
| | B36 | | | + | | + | | + | | | | |
| | B38 | | | + | + | + | | + | | | | + |
| | B42 | | | | | | | + | | | | |
| | SB04 | + | | + | + | + | + | + | | + | | + |
| | SB15 | | | | | + | | + | | | | + |
| | SB27 | | | | | | | | | | | + |

FIG. 13

|  | ANTI-F.IXa | | | | | | | | | | |
|---|---|---|---|---|---|---|---|---|---|---|---|
|  |  | A19 | A25 | A31 | A38 | A39 | A40 | A41 | A44 | A50 | A69 | XB12 |
| ANTI-F.X | B2 |  |  |  |  |  |  |  | + |  |  |  |
|  | B5 |  |  |  |  |  |  |  | ++ |  |  |  |
|  | B9 |  |  |  |  |  |  |  |  |  |  |  |
|  | B10 |  |  |  |  |  |  |  |  |  |  | ++ |
|  | B11 |  |  |  |  |  |  |  |  | ++ |  | ++ |
|  | B12 |  |  |  |  |  |  |  |  |  |  | ++ |
|  | B13 |  |  |  |  |  |  |  |  |  |  | +++ |
|  | B14 |  |  |  |  |  |  |  | + |  |  | ++ |
|  | B15 |  |  |  |  |  |  |  | + |  |  | ++ |
|  | B16 |  |  | + |  |  |  |  |  |  |  | +++ |
|  | B18 |  |  |  |  |  |  |  | ++ |  |  |  |
|  | B19 |  |  |  |  |  |  |  | + |  |  |  |
|  | B20 |  |  |  |  |  |  |  | ++ |  |  |  |
|  | B21 |  |  |  |  |  |  |  | ++ |  |  |  |
|  | B23 |  |  |  |  |  |  |  | ++ |  |  |  |
|  | B25 |  |  |  |  |  |  |  | ++ |  |  |  |
|  | B26 |  |  |  |  |  |  | + | ++++ |  | ++++ |  |
|  | B27 |  |  |  |  |  |  |  | ++ |  |  |  |
|  | B31 | ++ |  |  |  |  |  |  |  |  |  | +++ |
|  | B34-1 |  |  |  |  |  |  |  |  |  |  |  |
|  | B34-2 |  |  |  |  |  |  |  |  |  |  |  |
|  | B35 |  |  | + |  |  |  |  |  | ++ |  | ++ |
|  | B36 |  |  |  |  |  |  |  |  |  |  |  |
|  | B38 |  |  |  |  |  |  |  |  |  |  |  |
|  | B42 |  |  |  |  |  |  |  |  |  |  |  |
|  | SB04 | ++ |  | + | ++ | ++ |  | ++ | ++ | +++ |  | +++ |
|  | SB15 |  |  |  |  |  |  |  | ++ |  |  |  |
|  | SB27 |  |  |  |  |  |  |  |  |  |  |  |

BISPECIFIC ANTIBODY SUBSTITUTING FOR FUNCTIONAL PROTEINS

CROSS-REFERENCE TO RELATED APPLICATIONS

This application is the National Stage of International Application No. PCT/JP2004/014911, filed on Oct. 8, 2004, which claims the benefit of International Applications No. PCT/JP2003/13062, filed on Oct. 10, 2003, and PCT/JP2003/13123, filed on Oct. 14, 2003. The contents of all of the foregoing applications are hereby incorporated by reference in their entireties.

TECHNICAL FIELD

The present invention relates to bispecific antibodies that functionally substitute for the cofactors which enhance enzymatic reaction, and pharmaceutical compositions comprising the antibody as an active ingredient.

BACKGROUND ART

Antibodies have received much attention as a medicine because of their high stability in blood and low antigenicity. Of these are bispecific antibodies that can simultaneously recognize two types of antigens. Bispecific antibodies have been proposed for some time; however, only antibodies that simply connect two types of antigens, such as those for retargeting NK cells, macrophages, and T cells (see Non-Patent Document 7), have been reported. For example, MDX-210, which is currently under clinical study, is a bispecific antibody that merely retargets FcγRI-expressing monocytes and such to HER-2/neu-expressing cancer cells. Thus, there is no example so far that utilizes a bispecific antibody as an alternative means to functionally substitute for the cofactor which enhances enzymatic reaction.

Examples of cofactors are tissue factor (TF), blood coagulation factor V (F.V), activated blood coagulation factor V (F.Va), blood coagulation factor VIII (F.VIII), activated blood coagulation factor VIII (F.VIIIa), thrombomodulin (TM), protein S (PS), protein Z (PZ), heparin, complement C4b, complement regulatory factor H, membrane cofactor protein (MCP), and complement receptor 1 (CR1).

Of these, F.VIII/F.VIIIa is a cofactor required for sufficient activity expression of activated blood coagulation factor IX (F.IXa). Scheiflinger F. et al. discovered that a certain anti-F.IXDF.IXa antibody acts to promote the activation of blood coagulation factor X (F.X) by F.IXa in a chromogenic assay (Patent Document 1). However, in an assay that examines the ability for coagulation recovery in F.VIII-deficient plasma, the coagulation recovery ability was observed only when F.IXa was added exogenously, but not if this antibody was used alone.

F.VIIIa has been known to interact with not only F.IXa but also with F.X (see Non-Patent Documents 5 and 6). In this respect, the antibody of Scheiflinger F. et al. cannot be said to sufficiently substitute for the function of F.VIII/F.VIIIa, and its activity also seems to be insufficient.

Through dedicated research, the present inventors succeeded in producing bispecific antibodies that functionally substitute for the cofactors which enhance enzymatic activity, and thereby completed this invention.

[Patent Document 1] WO 01/19992
[Patent Document 2] U.S. Pat. No. 4,474,893
[Patent Document 3] EP 404,097
[Patent Document 4] WO 93/11161
[Patent Document 5] Japanese Patent Application No: 2002-112369
[Patent Document 6] Japanese Patent Application No: 2003-012648
[Patent Document 7] Japanese Patent Application Kokai Publication No. (JP-A) H5-304992 (unexamined, published Japanese patent application)
[Patent Document 8] JP-A H2-145187
[Patent Document 9] JP-A H5-213775
[Patent Document 10] JP-A H110-165184
[Patent Document 11] JP-A H111-71288
[Patent Document 12] JP-A 2002-518041
[Patent Document 13] JP-A H 11-506310
[Patent Document 14] JP-A H5-199894
[Patent Document 15] JP-A H110-511085
[Patent Document 16] JP-A H5-184383
[Non-Patent Document 1] Nilsson I M et al., "J. Intern. Med." 1992, Vol.235, p.25-32
[Non-Patent Document 2] Lofqvist T et al,. "J. Intern. Med" 1997, Vol.241, p.395-400 (the "o" of Lofqvist is written with an umlaut)
[Non-Patent Document 3] 24$^{th}$ Meeting of The Japanese Society on Thrombosis and Hematosis, Special Committee on Examining Hemophilia Standardization, Mini-symposium, 2001, http://wwwjsth.org
[Non-Patent Document 4] Medical Bulletin #193 1994
[Non-Patent Document 5] Mertens K et al., "Thromb. Haemost." 1999, Vol.82, p.209-217
[Non-Patent Document 6] Lapan K A et al., "Thromb. Haemost." 1998, Vol.80, p.418-422
[Non-Patent Document 7] Segal D M et al., "Journal of Immunological Methods" 2001, Vol.248, p.1-6
[Non-Patent Document 8] Bos R and Nieuwenhuitzen W, "Hybridoma" 1992, Vol.11, No. 1, p.41-51
[Non-Patent Document 9] Brennan M et al., "Science" 1985, Vol.229, No.1708, p.81-3
[Non-Patent Document 10] Karpovsky B et al., "J. Exp. Med." 1984, Vol.160, No.6, p.1686-701
[Non-Patent Document 11] Suresh M R et al., "Methods Enzymol." 1986, Vol.121, p. 210-28
[Non-Patent Document 12] Massimo Y S et al., "J. Immunol. Methods" 1997, Vol.201, p.57-66
[Non-Patent Document 13] Brennan M et al., "Science" 1985, Vol.229, p.81
[Non-Patent Document 14] Shalaby M R et al., "J. Exp. Med." 1992, Vol.175, p.217-25
[Non-Patent Document 15] Holliner P et al., "Proc. Natl. Acad. Sci. USA" 1993, Vol.90, p. 6444-8
[Non-Patent Document 16] Ridgway J B et al., "Protein Eng." 1996, Vol.9, p. 617-21
[Non-Patent Document 17] Hammerling U et al., "J. Exp. Med." 1968, Vol.128, p.1461-73
[Non-Patent Document 18] Kurokawa T et al., "Bio/Technology" 1989, Vol.7, p.1163
[Non-Patent Document 19] Link B K et al., "Blood" 1993, Vol.81, p.3343
[Non-Patent Document 20] Nitta T et al., "Lancet" 1990, Vol.335, p.368-71
[Non-Patent Document 21 ] deLeij L et al., "Foundation Nationale de Transfusion Sanguine, Les Ulis France" 1990, p.249-53
[Non-Patent Document 22] Le Doussal J M et al., "J. Nucl. Med." 1993, Vol.34, p.1662-71
[Non-Patent Document 23] Stickney D R et al., "Cancer Res." 1991, Vol.51, p.6650-5
[Non-Patent Document 24] Weiner L M et al., "Cancer Res." 1993, Vol.53, p.94-100

[Non-Patent Document 25] Kroesen B J et al., "Br. J. Cancer" 1994, Vol.70, p.652-61

[Non-Patent Document 26] Weiner G J et al., "J. Immunol." 1994, Vol.152, p.2385

[Non-Patent Document 27] Suresh M R et al., "Proc. Natl. Acad. Sci. USA" 1986, Vol.83, p.7989-93

[Non-Patent Document 28] Milstein C and Cuello A C, "Nature" 1983, Vol.305, p.537

[Non-Patent Document 29] Xiang J et al., "Mol. Immunol." 1990, Vol.27, p.809

[Non-Patent Document 30] Bebbington C R et al., "Bio/Technology" 1992, Vol.10, p.169

[Non-Patent Document 31] Huse W D et al., "Science" 1989, Vol. 246, p.1275

[Non-Patent Document 32] McCafferty J et al., "Nature" 1990, Vol.348, p.552

[Non-Patent Document 33] Kang A S et al., "Proc. Natl. Acad. Sci. USA" 1991, Vol.88, p.4363

DISCLOSURE OF THE INVENTION

An objective of the present invention is to provide bispecific antibodies that functionally substitute for the cofactors which enhance enzymatic reaction.

Through dedicated research, the present inventors succeeded in discovering bispecific antibodies that specifically bind to both F.DUF.IXa and F.X and substitute for the function of cofactor F.VIIIa (i.e., a function to promote F.X activation by F.IXa). That is, the present inventors succeeded in producing bispecific antibodies that recognize both an enzyme and its substrate and functionally substitute for cofactors of the enzyme.

The present invention relates to bispecific antibodies that functionally substitute for the cofactors which enhance enzymatic reaction, and more specifically to:

[1] An antibody recognizing both an enzyme and a substrate thereof, wherein said antibody is a bispecific antibody which functionally substitutes for a cofactor that enhances the enzymatic reaction.

[2] The antibody according to [1], wherein said enzyme is a proteolytic enzyme.

[3] The antibody according to [2], wherein said proteolytic enzyme, substrate, and cofactor are blood coagulation/fibrinolysis-associated factors.

[4] The antibody according to [3], wherein the enzyme of a blood coagulation/fibrinolysis-associated factor is blood coagulation factor IX and/or activated blood coagulation factor IX; the substrate is blood coagulation factor X; and the cofactor is blood coagulation factor VIII and/or activated blood coagulation factor VIII.

[5] The antibody according to any one of [1] to [4], wherein said antibody comprises a complementarity determining region comprising the amino acid sequence of anti-blood coagulation factor Ix/IXa antibody CDR3 of the following (a1) or (a2) or a complementarity determining region functionally equivalent thereto, and a complementarity determining region comprising the amino acid sequence of anti-blood coagulation factor X antibody CDR3 described in any one of the following (b1) to (b9) or a complementarity determining region functionally equivalent thereto:

(a1) H chain CDR 3 amino acid sequence described in SEQ ID NO: 16;

(a2) H chain CDR 3 amino acid sequence described in SEQ ID NO: 20;

(b1) H chain CDR 3 amino acid sequence described in SEQ ID NO: 24;

(b2) H chain CDR 3 amino acid sequence described in SEQ ID NO: 28;

(b3) H chain CDR 3 amino acid sequence described in SEQ ID NO: 32;

(b4) H chain CDR 3 amino acid sequence described in SEQ ID NO: 36;

(b5) H chain CDR 3 amino acid sequence described in SEQ ID NO: 40;

(b6) H chain CDR 3 amino acid sequence described in SEQ ID NO: 44;

(b7) H chain CDR 3 amino acid sequence described in SEQ ID NO: 48;

(b8) H chain CDR 3 amino acid sequence described in SEQ ID NO: 52;

(b9) H chain CDR 3 amino acid sequence described in SEQ ID NO: 56.

[6] The antibody according to any one of [1] to [4], wherein said antibody comprises a complementarity determining region comprising the amino acid sequence of anti-blood coagulation factor Ix/Ixa antibody CDR of the following (a1) or (a2) or a complementarity determining region functionally equivalent thereto, and a complementarity determining region comprising the amino acid sequence of anti-blood coagulation factor X antibody CDR described in any one of the following (b1) to (b9) or a complementarity determining region functionally equivalent thereto:

(a1) H chain CDR 1, 2, and 3 amino acid sequences described in SEQ ID NOs: 14, 15, and 16, respectively;

(a2) H chain CDR 1, 2, and 3 amino acid sequences described in SEQ ID NOs: 18, 19, and 20, respectively;

(b1) H chain CDR 1, 2, and 3 amino acid sequences described in SEQ ID NOs: 22, 23, and 24, respectively;

(b2) H chain CDR 1, 2, and 3 amino acid sequences described in SEQ ID NOs: 26, 27, and 28, respectively;

(b3) H chain CDR 1, 2, and 3 amino acid sequences described in SEQ ID NOs: 30, 31, and 32, respectively;

(b4) H chain CDR 1, 2, and 3 amino acid sequences described in SEQ ID NOs: 34, 35, and 36, respectively;

(b5) H chain CDR 1, 2, and 3 amino acid sequences described in SEQ ID NOs: 38, 39, and 40, respectively;

(b6) H chain CDR 1, 2, and 3 amino acid sequences described in SEQ ID NOs: 42, 43, and 44, respectively;

(b7) H chain CDR 1, 2, and 3 amino acid sequences described in SEQ ID NOs: 46, 47, and 48, respectively;

(b8) H chain CDR 1, 2, and 3 amino acid sequences described in SEQ ID NOs: 50, 51, and 52, respectively;

(b9) H chain CDR 1, 2, and 3 amino acid sequences described in SEQ ID NOs: 54, 55, and 56, respectively.

[7] A composition comprising the antibody according to any one of [1] to [6] and a pharmaceutically acceptable carrier.

[8] The composition according to [7], wherein said composition is a pharmaceutical composition used for preventing and/or treating bleeding, disorder accompanied by bleeding, or disorder caused by bleeding.

[9] The composition according to [8], wherein the bleeding, disorder accompanied by bleeding, or disorder caused by bleeding is a disorder that arises and/or progresses as a result of an activity decrease or deficiency of blood coagulation factor VIII and/or activated blood coagulation factor VIII.

[10] The composition according to [9], wherein the disorder that arises and/or progresses as a result of an activity decrease or deficiency of blood coagulation factor VIII and/or activated blood coagulation factor VIII is hemophilia A.

[11] The composition according to [9], wherein the disorder that arises and/or progresses as a result of an activity decrease or deficiency of blood coagulation factor VIII and/or activated blood coagulation factor VIII is a disorder in which an inhibitor against blood coagulation factor VIII and/or activated blood coagulation factor VIII is generated.

[12] The composition according to [9], wherein the disorder that arises and/or progresses as a result of an activity decrease or deficiency of blood coagulation factor VIII and/or activated blood coagulation factor VIII is acquired hemophilia.

[13] The composition according to [9], wherein the disorder that arises and/or progresses as a result of an activity decrease of blood coagulation factor VIII and/or activated blood coagulation factor VIII is von Willebrand's disease.

[14] A method for preventing and/or treating bleeding, disorder accompanied by bleeding, or disorder caused by bleeding, wherein said method comprises the step of administering the antibody according to any one of [1] to [6], or the composition according to any one of [7] to [13].

[15] Use of the antibody according to any one of [1] to [6] for preparing the composition according to any one of [7] to [13].

[16] A kit used in the method of preventing and/or treating disorders according to [14], wherein said kit comprises at least the antibody according to any one of [1] to [6] or the composition according to [7].

[17] A method of preventing and/or treating bleeding, disorder accompanied by bleeding, or disorder caused by bleeding, wherein said method comprises the step of administering the antibody according to any one of [4] to [6] or the composition according to any one of [7] to [13] in combination with blood coagulation factor VIII.

[18] A kit used in the method of preventing and/or treating bleeding, disorder accompanied by bleeding, or disorder caused by bleeding according to [17], wherein said kit comprises at least the antibody according to any one of [4] to [6], or the composition according to [7], and blood coagulation factor VIII.

BRIEF DESCRIPTION OF THE DRAWINGS

FIG. 12 depicts results of measuring the F.VIIIa-mimetic activity using culture supernatants of the expressed bispecific antibodies, which are combinations of an anti-F.IXa antibody (A19, A25, A31, A38, A39, A40, A41, A44, A50, A69, or XB12) and an anti-F.X antibody (B2, B5, B9, B10, B11, B12, B13, B14, B15, B16, B18, B19, B20, B21, B23, B25, B26, B27, B31, B34-1, B34-2, B35, B36, B38, B42, SB04, SB15, or SB27). "+" represents cases where the F.VIIIa-mimetic activity is 0.1 or more.

FIG. 13 depicts results of a plasma coagulation assay performed using purified preparations of expressed bispecific antibodies, which are combined from an anti-F.IXa antibody (A19, A25, A31, A38, A39, A40, A41, A44, A50, A69, or XB12) and an anti-F.X antibody (B2, B5, B9, B10, B11, B12, B13, B14, B15, B16, B18, B19, B20, B21, B23, B25, B26, B27, B31, B34-1, B34-2, B35, B36, B38, B42, SB04, SB15, or SB27). The coagulation time was shortened by 10 to 20 seconds ("+"), 20 to 40 seconds ("++"), 40 to 50 seconds ("+++") or 50 seconds ("++++") or more with the antibody addition compared with when the antibodies were not added.

DETAILED DESCRIPTION

Figure 1:
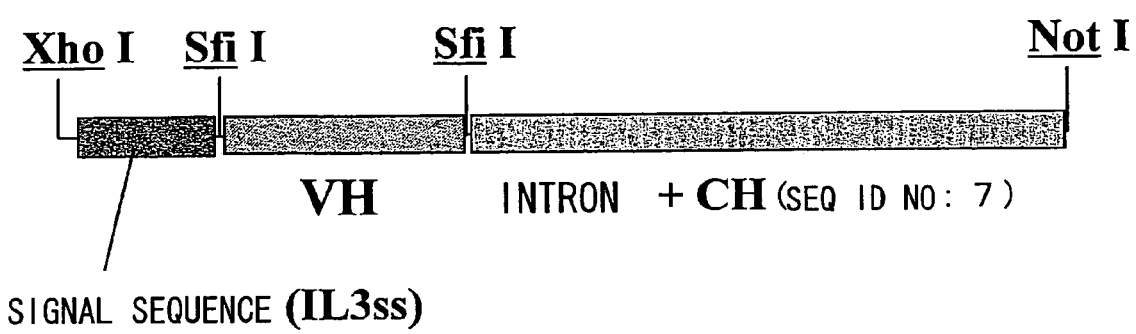
FIG. 1 depicts the insertion region of pcDNA4-g4H.

A bispecific antibody according to the present invention is a molecule comprising two types of antibodies or antibody fragments having specificities for different antigens. The bispecific antibody is, not particularly limited, but preferably monoclonal.

The bispecific antibodies of the present invention are preferably recombinant antibodies, generated using gene recombination techniques (see, e.g., Borrebaeck C A K and Larrick J W, THERAPEUTIC MONOCLONAL ANTIBODIES, Published in the United Kingdom by MACMILLAN PUBLISHERS LTD, 1990). A recombinant antibody can be obtained by cloning an antibody-encoding DNA from antibody-producing cells, such as hybridomas or sensitized lymphocytes, incorporating the DNA into an appropriate vector, and introducing the vector into a host for antibody production.

Further, antibodies of the present invention may be antibody fragments or modified antibodies. Antibody fragments include diabody (Db), linear antibody, single-strand antibody (hereinafter also referred to as scFv) molecules, etc. Herein, "Fv" fragment represents the smallest antibody fragment, comprising a complete antigen recognition site and binding site. An "Fv" fragment is a dimer ($V_H$-$V_L$ dimer) in which one heavy (H) chain variable region ($V_H$) and one light (L) chain variable region ($V_L$) are strongly connected by a non-covalent bond. Three complementarity determining regions (CDRs) of each variable region interact to form an antigen-binding site on the surface of a $V_H$-$V_L$ dimer. Six CDRs confer an antigen-binding site on an antibody. However, even one variable region (or half of an Fv which contains only three antigen-specific CDRs) is capable of recognizing an antigen and binding thereto, although its affinity is lower than that of the entire binding site.

In addition, Fab fragment (also referred to as (F(ab)) further contains an L chain constant region and an H chain constant region (CH1). A Fab' fragment differs from a Fab fragment in that the former contains several additional residues derived from the carboxyl terminal of an H chain CH1 region, which comprises one or more cysteines from the hinge region of an antibody. Fab'-SH refers to Fab' having a free thiol group in one or more cysteine residues of the constant region. F(ab') fragments are generated by cleaving the disulfide bond in the cysteines of the hinge portion of a F(ab')$_2$ pepsin digest. Other chemically bound antibody fragments are also known to those skilled in the art.

Diabody refers to a bivalent antibody fragment constructed by gene fusion (Holliger P et al., Proc. Natl. Acad. Sci. USA 90: 6444-6448 (1993); EP 404,097; WO 93/11161; etc.). Diabody is a dimer comprising two peptide chains; in each polypeptide chain, an L chain variable region ($V_L$) is connected to an H chain variable region ($V_H$) on the same chain via a linker that is too short to allow paring between the two regions (for example, about 5 residues). $V_L$ and $V_H$ encoded on the same polypeptide chain form a dimer because they cannot form a single-stranded variable region fragment due to the short linker between them. Thus, a diabody ends up with two antigen binding sites.

A single-strand antibody or scFv fragment contains the $V_H$ and $V_L$ regions of an antibody, and these regions exist in a single polypeptide chain. In general, an Fv polypeptide further contains a polypeptide linker between $V_H$ and $V_L$ regions, such that scFv is able to form a structure that is necessary for antigen binding (see Pluckthun "The Pharmacology of Monoclonal Antibodies" Vol. 113 (Rosenburg and Moore ed (Springer Verlag, New York) pp. 269-315, 1994 for general remarks on scFv). The linkers of the present invention are not particularly limited, as long as they do not inhibit expression of the antibody variable regions connected to both ends of a linker.

An IgG type bispecific antibody can be secreted by a hybrid hybridoma (quadroma) formed by fusing two types of hybridomas that produce IgG antibodies (Milstein C et al., Nature 1983, 305: 537-540). It can also be secreted by introducing into cells genes of the L chains and H chains that constitute the two IgGs of interest (a total of four types of genes) for co-expression.

However, theoretically, there are as many as ten combinations of H chains and L chains in the IgGs produced by these methods. It is difficult to purify an IgG comprising the desired combination of H and L chains from ten different types of IgGs. Furthermore, in theory, the amount of the combination of interest is dramatically decreased, and thus large-scale cell culture is required, leading to a further increase in manufacturing cost.

In this case, by appropriately substituting amino acid(s) in the CH3 region of an H chain, it is possible to preferentially secrete IgGs that have a heterologous combination of H chains (Ridgway, JB et al. Protein Engineering 1996, 9: 617-621, Merchant, AM et al. Nature Biotechnology 1998, 16: 677-681).

As for L chains, an L chain variable region is less diverse compared to an H chain variable region; therefore, acquisition of a common L chain that provides binding activities with two H chains can be expected. Efficient expression of a bispecific IgG becomes possible by introducing genes of this common L chain and both of the H chains into a cell for IgG expression (Nature Biotechnology. 1998, 16, 677-681). However, the possibility of two randomly selected types of antibodies containing the same L chain is low; thus, it is difficult to put the aforementioned idea into practice. In this respect, a method has been proposed for selection of a common L chain adapting arbitrary different H chains to show high binding ability (WO 2004/065611). An H chain having the above-described CH3 variant (Nature Biotechnology. 1998, 16, 677-681) is rarely secreted in the absence of the other H chain. By making use of this characteristic to first induce expression of the right-arm L chain and H chain and stop the expression, and then induce expression of the left-arm L chain and H chain, the proportion of IgGs expressed in the combination of interest may be increased (PCT/JP2004/008585).

A bispecific antibody can also be prepared by chemically cross-linking Fab's. A bispecific F(ab')$_2$ can be produced, for example, by maleimidating a Fab' prepared from one antibody with o-PDM (ortho-phenylenedi-maleimide) and reacting the product with a Fab' prepared from another antibody, so as to cross-link Fab's derived from different antibodies (Keler T et al. Cancer Research 1997, 57: 4008-4014). Further, a method for chemically connecting antibody fragments such as a Fab'-thionitrobenzoic acid (TNB) derivative and Fab'-thiol (SH) is also known (Brennan M et al. Science 1985, 229: 81-83).

Instead of cross linkage, a leucine zipper derived from Fos and Jun or the like can be used. Although Fos and Jun also form a homodimer, their preferential heterodimer formation is utilized. A Fab' added with a Fos leucine zipper and a second Fab' added with a Jun leucine zipper are expressed for preparation. By mixing and reacting monomeric Fab'-Fos and Fab'-Jun, which have been reduced under mild conditions, a bispecific F(ab')$_2$ can be formed (Kostelny S A et al. J. of Immunology, 1992, 148: 1547-53). This method is not limited to Fab' and can also be applied to scFv, Fv, etc.

A bispecific antibody can also be prepared in a form of diabody. A bispecific diabody is a heterodimer comprising two cross-over scFv fragments. That is, a bispecific diabody can be prepared by constructing a heterodimer using $V_H(A)$-$V_L(B)$ and $V_H(B)$-$V_L(A)$, which have been formed by connecting $V_H$ and $V_L$ derived from two types of antibodies: A and B, with a relatively short linker of about 5 amino acid residues (Holliger P et al. Proc. of the National Academy of Sciences of the USA 1993, 90: 6444-6448).

In this case, construction of a bispecific diabody of interest can be promoted by performing appropriate amino acid substitutions (knobs-into-holes: Zhu Z et al. Protein Science. 1997, 6: 781-788) so as to link two types of scFv's with a flexible and relatively long linker of about 15 amino acid residues (a single-chain diabody: Kipriyanov S M et al. J. of Molecular Biology. 1999, 293: 41-56).

sc(Fv)$_2$ which can be prepared by linking two types of scFv's with a flexible and relatively long linker of about 15 amino acid residues can also become a bispecific antibody (Mallender W D et al. J. of Biological Chemistry, 1994, 269: 199-206).

A modified antibody may be, for example, an antibody that binds to various molecules such as polyethylene glycol (PEG). In the modified antibodies of the present invention, substances to be bound are not limited. Such modified antibodies can be obtained by chemically modifying the antibodies obtained. These methods have already been established in this field.

The antibodies of the present invention include human antibody, mouse antibody, rat antibody and such, without any limitation on their origins, and may be genetically modified antibodies such as chimera antibody and humanized antibody.

Methods for obtaining human antibodies are known, and a human antibody of interest can be obtained, for example, by immunizing a transgenic animal having all repertoires of human antibody genes with an antigen of interest (see WO 93/12227, WO 92/03918, WO 94/02602, WO 94/25585, WO 96/34096, WO 96/33735).

Genetically modified antibodies can be produced by known methods. Specifically, for example, a chimera antibody comprises variable regions from the H and L chains of an antibody from immunized animals, and constant regions from the H and L chains of a human antibody. A chimera antibody can be obtained by linking a DNA encoding the variable region of an antibody derived from immunized animals with a DNA encoding the constant region of a human antibody, inserting the resulting DNA into an expression vector, and introducing the recombinant vector into a host for production.

A humanized antibody is a modified antibody also referred to as reshaped human antibody. A humanized antibody is constructed by grafting the complementarity determining region (CDR) of an antibody derived from immunized animals into the CDR of a human antibody. General genetic engineering technologies are also known.

Specifically, a DNA sequence designed to link the CDR of a mouse antibody to the framework region (FR) of a human antibody is synthesized by PCR, using several oligonucleotides that have been prepared to contain overlapping portions at their terminal regions. After linking the obtained DNA to a DNA encoding the constant region of a human antibody, the resulting DNA is incorporated into an expression vector and introduced into a host to produce a humanized antibody (see EP 239400 and WO 96/02576). As a human antibody FR to be linked via CDR, one that is capable of forming an antigen-binding site with a good complementarity determining region is selected. Amino acids of the framework region in an antibody variable region may be substituted as necessary, so that the complementarity determining region of a reshaped human antibody forms an appropriate antigen-binding site (Sato K et al, Cancer Research 1993, 53: 851-856). The framework region may be substituted with framework regions derived from various human antibodies (see WO 99/51743).

The present invention provides bispecific antibodies which functionally substitute for cofactors that recognize both an enzyme and its substrate.

Cofactors of the present invention are not particularly limited, as long as they are capable of acting on an enzyme to enhance the enzymatic reaction. A cofactor of the present invention is, for example, a cofactor of a proteolytic enzyme. Specific examples of a cofactor of a proteolytic enzyme are cofactors for blood coagulation and fibrinolysis associated factors (F.VIII/F.VIIIa, F.V/F.Va, PZ, TM, TM/PS system), cofactors for complement reactions (C4b, MCP, CR1, H factor), and such.

The following combinations can be listed as specific examples of enzyme and enzyme substrate, as well as enzyme cofactors.

(a) Cofactor for Blood Coagulation and Fibrinolysis Associated Factor (Example 1)
   Enzyme: F.IXa
   Substrate: F.X
   Cofactor: F.VIII/F.VIIIa Cofactor F.VIIIa binds to both F.IXa and F.X and enhances F.X activation by F.IXa. Among bispecific antibodies that recognize both the above-described enzyme F.IXa and substrate F.X, some have an enhancing effect on F.X activation. Some of these antibodies are thought to have an effect of substituting for the function of cofactor F.VIII/F.VIIIa.

(b) Cofactor for Blood Coagulation and Fibrinolysis Associated Factor (Example 2)
Enzyme: ZPI
Substrate: F.X/F.Xa
Cofactor: PZ Cofactor PZ binds to ZPI of the serpin family and activated blood coagulation factor X (F.Xa) to enhance the F.Xa-inhibiting activity of ZPI. Specifically, some bispecific antibodies that recognize both ZPI and F.X/F.Xa are thought to have an effect of substituting for the PZ function.

(c) Cofactor for Blood Coagulation and Fibrinolysis Associated Factor (Example 3)
Enzyme: thrombin
Substrate: TAFI
Cofactor: TM Cofactor TM enhances TAFI activation by thrombin. Specifically, some bispecific antibodies that recognize both thrombin and TAFI are thought to have an effect of substituting for the TM function.

(d) Cofactors for Blood Coagulation and Fibrinolysis Associated Factor (Example 4)
Enzyme: thrombin
Substrate: PC
Cofactors: TM/PS The TM/PS system enhances PC activation by thrombin. Specifically, some bispecific antibodies that recognize both thrombin and PC are thought to functionally substitute for the TM/PS system.

(e) Cofactor for Blood Coagulation and Fibrinolysis Associated Factor (Example 5)
Enzyme: F.Xa
Substrate: Prothrombin
Cofactor: F.V/F.Va Cofactor F.Va binds to both F.Xa and prothrombin to enhance prothrombin activation by F.Xa. Among bispecific antibodies that recognize both the above-described enzyme F.Xa and its substrate prothrombin, some have enhancing effects on prothrombin activation. Some of these antibodies are thought to have a function that substitutes for the function of cofactor F.V/F.Va.

(f) Cofactor for Complement Reaction (Example 1)
Enzyme: C1s
Substrate: C2
Cofactor: C4b C4b has C1s' promoting effect on C2 decomposition. Specifically, some bispecific antibodies that recognize both C1s and C2 are thought to functionally substitute for C4b.

(g) Cofactors for Complement Reaction (Example 2)
Enzyme: Complement Regulatory Factor I
Substrate: C3b
Cofactors: Complement Regulatory Factor H,
  Membrane Cofactor Protein (MCP), and
  Complement Receptor 1 (CR1)

Complement Regulatory Factors H, MCP, and CR1 have the promoting effect of Complement Regulatory Factor 1 on C3b degradation. Specifically, among bispecific antibodies that recognize both Complement Regulatory Factor 1 and C3b, some are thought to functionally substitute for Complement Regulatory Factors H, MCP, and CR1.

Among the above-described cofactors, F.VIII/F.VIIIa is particularly preferable. Although F.VIIV/F.VIIIa undergoes limited proteolysis by proteolytic enzymes such as thrombin, as long as it has F.VIII/F.VIIIa activity, its form does not matter. Further, F.VIIIVF.VIIIa variants and F.VIII/F.VIIIa that have been artificially modified by gene recombination techniques are also included in F.VIII/F.VIIIa, as long as they retain F.VIII/F.VIIIa cofactor activity.

Methods for obtaining bispecific antibodies which functionally substitute for cofactors of the present invention are not particularly limited, and may be obtained by any methods. For example, when obtaining a bispecific antibody that functionally substitutes for enzyme A and substrate B, enzyme A and substrate B are each immunized to an animal to obtain anti-enzyme A antibody and anti-substrate B antibody. Subsequently, a bispecific antibody comprising the anti-enzyme A antibody H and L chains and the anti-substrate B antibody H and L chains is produced. Herein, it is desirable to obtain several types of each of the anti-enzyme A antibody and the anti-substrate B antibody, such that these antibodies can be preferably used to produce as many combinations of bispecific antibodies as possible. After bispecific antibodies are produced, antibodies with an activity that substitutes for cofactor function are selected.

Antibodies against an enzyme or a substrate can be obtained by methods known to those skilled in the art. For example, antibodies can be prepared by immunizing animals with antigens. Antigens for immunizing animals are, for example, complete antigens having immunogenicity and incomplete antigens (including hapten) without immunogenicity. In the present invention, an enzyme whose cofactor can be functionally substituted by an antibody of the present invention which acts as the cofactor, or a substrate of the enzyme, is used as the above-described antigen (immunogen). As animals to be immunized, for example, mouse, rat, hamster, guinea pig, rabbit, chicken, rhesus monkey and such can be used. Immunization of these animals with antigens can be performed by methods known to those skilled in the art. In the present invention, antibody L chain and H chain variable regions are preferably collected from immunized animals or cells thereof. This procedure can be performed by one skilled in the art by using generally known methods. Antigen-immunized animals express antibodies against the antigen, especially in the spleen cells. Therefore, for example, mRNA can be prepared from spleen cells of an immunized animal, and variable regions of the L chain and H chain can be recovered by RT-PCR using primers to the animal's variable regions.

Specifically, animals are immunized with an enzyme or a substrate. The enzyme and substrate used as immunogens may be whole proteins or partial peptides thereof. Further, depending on the circumstances, a candidate antigen bound to another molecule to form a soluble antigen, or fragments of which, may be used as an immunogen for immunizing animals.

Spleen cells are isolated from the spleens of immunized mice, and fused with mouse myeloma cells to produce hybridomas. After selecting hybridomas that bind to the respective antigens, variable regions of the L chain and H chain are recovered by RT-PCR, using for example, primers corresponding to the variable regions. Primers to CDR, primers to framework regions which are less diversified than CDR, or primers to signal sequences and CH1 or L chain constant region ($C_L$) may also be used.

Alternatively, mRNA is extracted from the spleen cells of immunized animals, and cDNAs of the L chain and H chain variable regions are recovered by RT-PCR, using primers to vicinity of the variable regions. Further, lymphocytes can also be immunized in vitro, and used to construct scFv or Fab presenting libraries. The variable regions may be obtained by concentrating and cloning an antigen-binding antibody clone by panning. In this case, screening can also be performed using similar libraries constructed from mRNAs derived from the peripheral blood monocytes, spleen, tonsil and such of human and non-immunized animals as materials.

The variable regions are then used to prepare antibody expression vectors. By introducing an anti-enzyme antibody expression vector and an anti-substrate antibody expression vector into a same cell and expressing the antibodies, a bispecific antibody can be obtained.

Antibodies that have a cofactor function-substituting activity can be selected, for example, by the methods described below.

(1) In a reaction system comprising the enzyme and the substrate, the selection is performed using elevation of enzyme activity (substrate degradation ability) as an index, wherein the elevation of enzyme activity is a result of antibody addition.

(2) In a system for measuring or simulating the biological functions which the enzyme, substrate, and cofactor are involved in (for example, a system for measuring plasma coagulation), the selection is performed using activity of functional recovery as an index, wherein the activity of functional recovery is a result of antibody addition in the absence of the cofactor.

The antibody thus obtained can be purified to homogeneity. Separation and purification of the antibody may be performed by separation and purification methods used for general proteins. For example, antibodies can be separated and purified by appropriately selecting and combining chromatography columns such as affinity chromatography, filter, ultrafiltration, salting out, dialysis, SDS polyacrylamide gel electrophoresis, isoelectric electrophoresis and so on (Antibodies: A Laboratory Manual. Ed Harlow and David Lane, Cold Spring Harbor Laboratory, 1988), but the methods are not limited thereto. A column used in affinity chromatography is, for example, protein A column, protein G column and such.

For example, when F.VIII/F.VIIIa is the substitute cofactor, that is, when the enzyme and substrate combination is plasma coagulation and fibrinolysis associated factors F.IXa and F.X, the bispecific antibody of the present invention preferably has a structure comprising the variable region of an anti-F.IXa antibody and the variable region of an anti-F.X antibody.

Bispecific antibodies of the present invention which functionally substitute for F.VIII/F.VIIIa were generated by the following method. Mice were subcutaneously immunized with commercial F.IXa or F.X. Spleen cells were isolated from spleens of the immunized mice with an elevated antibody titer, and fused with mouse myeloma cells to form hybridomas. Hybridomas that bind to antigen F.IXa or F.X were selected, and the L chain and H chain variable regions were recovered by RT-PCR, using primers to the variable regions. The L chain variable region was incorporated into a $C_L$-containing L chain expression vector, and the H chain variable region was inserted into an H chain expression vector containing an H chain constant region. In addition, mRNA was extracted from the spleens of these immunized mice, and each cDNA of the L chain and H chain variable regions was recovered by RT-PCR, using primers to the respective variable region. Using these variable regions, an scFv-presenting phage library was constructed. Antigen-binding antibody clones were concentrated and cloned by panning and the antibody expression vectors were formed using the variable region thereof. The anti-F.IXa antibody (H chain, L chain) expression vectors and anti-F.X antibody (H chain, L chain) expression vectors were introduced into same cells for antibody expression and bispecific antibodies were obtained.

Bispecific antibodies thus obtained were assessed for their effects to functionally substitute for F.VIII/F.VIIIa (cofactors for F.X activation by F.IXa) in an assay system comprising F.XIa (F.IX activating enzyme), F.IX, F.X, a synthetic substrate (S-2222) for F.Xa, and phospholipid. In principle, as a bispecific antibody having activity to functionally substitute for F.VIII/F.VIIIa, bispecific antibodies showing F.VIIIa-mimetic activity of 0.1 or more in this assay system were selected based on the assay results. The F.VIIIa-mimetic activity referred to herein is a value obtained during 30 or 60 minutes by subtracting the value of absorbance change of a solvent or culture supernatant that does not express the antibody from the value of absorbance change of an antibody solution or a culture supernatant that expresses the antibody.

Bispecific antibodies selected above or bispecific antibodies closely related to them were measured for their ability to restore coagulation in a coagulation time assay system that uses human F.VIII-deficient plasma. As a result, bispecific antibodies which are capable of shortening coagulation time as compared to when not added were obtained. The coagulation time referred to herein is, as shown in Example 7, the activated partial thromboplastin time measured using human F.VIII-deficient plasma. Among these bispecific antibodies, preferable bispecific antibodies have the ability to shorten coagulation time by 10 seconds or more, more preferably by 20 seconds or more, even more preferably by 40 seconds or more, and most preferably by 50 seconds or more.

The H chain CDR3s of the present invention's antibodies are not particularly limited, but specifically have a complementarity determining region comprising an amino acid sequence described in any one of the H chain CDR3 sequences (SEQ ID NO: 16, 20, 60, 64, 68, 72, 76, 80, 84, 88,92, and 96) of XB12, XT04, A19, A25, A31, A38, A39, A40, A41, A44, A50, and A69 described in the examples described below or those functionally equivalent thereto, and the complementarity determining region comprising an amino acid sequence described in any one of the H chain CDR3 sequences (SEQ ID NO: 24, 28, 32, 36, 40, 44, 48, 52, 56, 100, 104, 108, 112, 116, 120, 124, 128, 132, 136, 140, 144, 148, 152, 156, 160, 164, 168, 172, 176, 180, 184, 188, 192, 196, 200, and 204) in SB04, SB05, SB06, SB07, SB21, SB30, SB34, SB38, SB42, B2, B5, B9, B10, B11, B12, B13, B14, B15, B16, B18, B19, B20, B21, B23, B25, B26, B27, B31, B34-1, B34-2, B35, B36, B38, B42, SB15, and SB27, respectively, or those functionally equivalent thereto.

Further, a specific example of the above-described antibodies is preferably combined from an antibody having a complementarity determining region comprising any one of the H chain CDR amino acid sequences of XB12, XT04, A19, A25, A31, A38, A39, A40, A41, A44, A50, and A69 (SEQ ID NO: 14-16, 18-20, 58-60, 62-64, 66-68, 70-72, 74-76, 78-80, 82-84, 86-88, 90-92, and 94-96) or a complementarity determining region functionally equivalent thereto, and an antibody having a complementarity determining region comprising any one of the H chain CDR amino acid sequences (SEQ ID NO: 22-24, 26-28, 30-32, 34-36, 38-40, 42-44, 46-48, 50-52, 54-56, 98-100, 102-104, 106-108, 110-112, 114-116, 118-120, 122-124, 126-128, 130-132, 134-136, 138-140, 142-144, 146-148, 150-152, 154-156, 158-160, 162-164, 166-168, 170-172, 174-176, 178-180, 182-184, 186-188, 190-192, 194-196, 198-200, and 202-204) in SB04, SB05, SB06, SB07, SB21, SB30, SB34, SB38, SB42, B2, B5, B9, B10, B11, B12, B13, B14, B15, B16, B18, B19, B20, B21, B23, B25, B26, B27, B31, B34-1, B34-2, B35, B36, B38, B42, SB15, and SB27), or a complementarity determining region functionally equivalent thereto Amino acid sequences of the H chain variable regions of XB12, XT04, A19, A25, A31, A38, A39, A40, A41, A44, A50, A69, SB04, SB05, SB06, SB07, SB21, SB30, SB34, SB38, SB42, B2, B5, B9, B10, B11, B12, B13, B14, B15, B16, B18, B19, B20, B21, B23, B25, B26, B27, B31, B34-1, B34-2, B35, B36, B38, B42, SB15, and SB27 disclosed in the present invention are shown as SEQ ID NOs: 13, 17, 57, 61, 65, 69, 73, 77, 81, 85, 89, 93, 21, 25, 29, 33, 37, 41, 45, 49, 53, 97, 101, 105, 109, 113, 117, 121, 125, 129, 133, 137, 141, 145, 149, 153, 157, 161, 165, 169, 173, 177, 181, 185, 189, 193, 197, and 201.

Amino acid sequences of the L chain variable regions of A44, B26, XB12, and SB04 disclosed in the present invention are shown as SEQ ID NOs: 205, 209, 213, and 217. The L chain CDR sequences of A44, B26, XB12, and SB04 are shown as SEQ ID NOs: 206-208, 210-212, 214-216, and 218-220. The H chain CDR nucleotide sequences of XB12, SB04, A44, and B26 are shown as SEQ ID NOs: 221 (222), 223 (224), 225 (226), 233 (234), 235 (236), 237 (238), 245 (246), 247 (248), 249 (250), 257 (258), 259 (260), and 261 (262) (sequences within brackets are amino acid sequences encoded by the respective nucleic acids), and their L chain CDR nucleotide sequences are shown as SEQ ID NOs: 227 (228), 229(230),231 (232), 239 (240), 241 (242), 243 (244), 251 (252), 253 (254), 255 (256), 263 (264), 265 (266), and 267 (268).

SEQ ID NOs: 58, 62, 66, 70, 74, 78, 82, 86, 90, 94, 98, 102, 106, 110, 114, 118, 122, 126, 130, 134, 138, 142, 146, 150, 154, 158, 162, 166, 170, 174, 178, 182, 186, 190, 194, 198, 202, 206, 210, 214, 218, 222, 228, 234, 240, 246, 252, 258, and 264 represent CDR1.

SEQ ID NOs: 59, 63, 67, 71, 75, 79, 83, 87, 91, 95, 99, 103, 107, 111, 115, 119, 123, 127, 131, 135, 139, 143, 147, 151, 155, 159, 163, 167, 171, 175, 179, 183, 187, 191, 195, 199, 203, 207, 211, 215, 219, 224, 230, 236, 242, 248, 254, 260, and 266 represent CDR2.

SEQ ID NOs: 60, 64, 68, 72, 76, 80, 84, 88, 92, 96, 100, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 226, 232, 238, 244, 250, 256, 262, and 268 represent CDR3.

Antibodies of the present invention are, not particularly limited, but preferably the bispecific antibodies combined from an anti-factor IXa antibody and an anti-factor X antibody, which have the same epitopes as the aforementioned antibodies or epitopes closely related thereto. Antibodies having a same or closely related epitope herein refer to, for example, those that compete with one another on antigen binding in competitive ELISA, etc. Without being limited thereto, in this competitive ELISA method, factor Ix/IXa or factor X is immobilized onto a 96-well MicroWell plate, an appropriately labeled antibody and an antibody to be assessed are simultaneously added, and bound antibody is detected by using the label. This label is not particularly limited and includes alkaline phosphatase label, peroxidase label, biotin labelled-streptavidin binding enzyme (alkaline phosphatase, peroxidase and so on), FITC and such. There is an epitope overlap if at least 50% competition is observed when the antibody is present in a concentration of up to 100,000-fold excess of an antibody to be assessed.

When preparing a full-length antibody using the variable regions disclosed in the present invention, constant regions of the antibody are not particularly limited, and those known to one skilled in the art, for example, ones-described in "Sequences of proteins of immunological interest, (1991), U.S. Department of Health and Human Services. Public Health Service National Institutes of Health" and "An efficient route to human bispecific IgG, (1998). Nature Biotechnology vol.16, 677-681", and such can be used.

In one embodiment of the antibodies of the present invention, the antibodies have an effect to functionally substitute for cofactors, and are thus expected to become effective drugs for diseases caused by decrease in the activity (function) of these cofactors. In cases where the cofactor functionally substituted by an antibody of the present invention is a blood coagulation and fibrinolysis-associated factor, the above-described diseases are, for example, bleeding, diseases accompanied by bleeding, diseases caused by bleeding, and such. In particular, functional reduction and deficiency in F.VIII/F.VIIIa, F.IX/F.IXa, and F.XI/F.XIa have been known to cause abnormal hemorrhage referred to as hemophilia.

Of the hemophilias, abnormal hemorrhage due to congenital hypofunction of F.VIII/F.VIIIa or deficiency in F.VIII/F.VIIIa is referred to as hemophilia A. When a hemophilia A patient bleeds, replacement therapy with a F.VIII formulation is performed. In addition, preventive administration of a F.VIII formulation may be performed (see Non-Patent Documents 1 and 2) on the day of vigorous exercise or on field trip, when frequent intra-articular bleeding occurs, or when the patient is classified as severe hemophilia. Since this preventive administration of F.VIII formulation remarkably reduces hemorrhage episodes of patients with hemophilia A, it has recently become widely popular. Reduction of bleeding episodes not only reduces lethal and nonlethal bleeding risks and the accompanying agony, but also prevents hemophilic arthropathy caused by frequent intra-articular hemorrhage. As a result, it greatly contributes to the improvement of hemophilia A patients' QOL.

The half life of a F.VIII formulation in blood stream is as short as about 12 to 16 hours. Therefore, for continuous prevention, it is necessary to administer a F.VIII formulation about three times a week. This is equivalent to maintaining approximately 1% F.VIII activity or more (see Non-Patent Documents 3 and 4). Also, in replacement therapies for bleeding event, it is necessary to periodically administer booster F.VIII formulations for a certain period of time, except when the bleeding is mild, in order to prevent rebleeding and establish complete hemostasis.

Further, F.VIII formulations are intravenously administered. There are technical difficulties in performing intravenous administration, and it becomes even more difficult particularly when performing administration on young patients whose veins are thin.

In the above-described preventive administration of F.VIII formulation and emergency administration thereof in cases of bleeding event, home treatment and self-injection are used in most cases. The need for frequent administration and the technical difficulties involved not only inflict pain on patients, but also become a reason that hinders home treatment and self-injection from becoming popular.

Accordingly, there have been strong demands for, as compared to current blood coagulation factor VIII formulations, drugs that have longer administration intervals and drugs that can be easily administered.

Further, anti-F.VIII antibodies which are referred to as inhibitors may be generated in hemophilia A patients, particularly in severe hemophilia A patients. If an inhibitor is generated, effects of F.VIII formulation become hindered by the inhibitor. As a result, hemostasis control becomes very difficult for patients.

When such a hemophilia A inhibitor patient bleeds, neutralization therapy using a mass dose of F.VIII formulation, or bypass therapy using a complex concentrate or F.VIIa formulation is usually performed. However, in neutralization therapy, administration of a mass dose of F.VIII formulation may adversely enhance the inhibitor (anti-F.VIII antibody) titer. Additionally, in bypass therapy, the relatively short half-lives (about 2 to 8 hours) of complex concentrates and the F.VIIa formulation are becoming problematic. Furthermore, since their action mechanisms are independent of the F.VIII/F.VIIIa function, that is, a function to catalyze the activation of F.X by F.IXa, hemostatic mechanism may not function well and become nonresponsive. Therefore, in many cases of hemophilia A inhibitor patients, sufficient hemostatic effects are not obtained, when compared to hemophilia A non-inhibitor patients.

Therefore, there have been strong demands for drugs that are unaffected by the presence of inhibitors and which can functionally substitute for F.VIII/F.VIIIa.

In addition to hemophilia and acquired hemophilia caused by anti-F.VIII autoantibody, von Willebrand's disease which is caused by functional abnormality or deficiency of vWF has been known as an abnormal bleeding disorder associated with F.VIII/F.VIIIa. vWF is necessary not only for the normal adhesion of platelets to subendothelial tissues at sites of vessel wall damage, but also for the formation of complexes with F.VIII to maintain a normal plasma F.VIII level. In patients with von Willebrand's disease, these functions decline and functional abnormality of hemostasis occurs.

In the above-described respects, methods that utilize antibodies may be considered for creation of drugs that (i) have long administration intervals, (ii) are easily administered and (iii) are unaffected by the presence of inhibitors, and (iv) can functionally substitute for F.VIII/F.VIIIa in a F.VIII/F.VIIIa-independent manner. Generally, the half-lives of antibodies in blood stream are relatively long—from several days to several weeks. Further, antibodies are known to migrate into the blood stream after subcutaneous administration. That is, antibody drugs in general meet the above-described requirements of (i) and (ii).

The present invention provides pharmaceutical compositions comprising an antibody of the present invention as an active ingredient. For example, when an antibody of the present invention is one of the antibodies that recognize both F.IX/F.IXa and F.X, and can functionally substitute for F.VIIIa, the antibody is expected to become a pharmaceutical (pharmaceutical composition) or drug for preventing or treating bleeding, disorders accompanied by bleeding, or disorders caused by bleeding. Furthermore, when an antibody of the present invention is one of the antibodies that recognize both F.X/F.Xa and prothrombin, and can functionally substitute for F.Va, the antibody is expected to become a pharmaceutical (pharmaceutical composition) or drug for preventing or treating bleeding, disorders accompanied by bleeding, or disorders caused by bleeding.

At the same time, it is expected that an antibody that binds to ZPI and F.X and functionally substitutes for PZ becomes a pharmaceutical (pharmaceutical composition) or drug with anti-thrombotic action, an antibody that binds to thrombin and TAFI and functionally substitutes for TM becomes a pharmaceutical (pharmaceutical composition) or drug with an hemostasis-promoting effect, and an antibody that binds to thrombin and PC and functionally substitutes for PS/TM system becomes a pharmaceutical (pharmaceutical composition) or drug with an coagulation-modulating effect.

In addition, since complement C4 deficiency causes systemic lupus erythematosus (SLE), an antibody that functionally substitutes for C4b is expected to become a pharmaceutical (pharmaceutical composition) or drug with an effect that suppresses SLE occurrence. Since H factor deficiency causes suppurative infection and autoimmune glomerulonephritis, an antibody that functionally substitutes for H factor is expected to become a pharmaceutical (pharmaceutical composition) or drug with an effect of suppressing the onset of these diseases.

For formulation of pharmaceuticals, pharmaceutical compositions comprising an antibody of the present invention used for treatment or prevention as an active ingredient may be mixed with an appropriate pharmaceutically acceptable carrier, medium and such that are inert thereto, if needed. For example, sterile water or physiological saline, stabilizer, excipient, antioxidant (ascorbic acid etc.), buffer (phosphoric acid, citric acid, other organic acids, etc.), antiseptic, surfactant (PEG, Tween, etc.), chelating agent (EDTA, etc.), binding agent and such can be cited. Pharmaceutical compositions may also contain other low molecular weight polypeptides, proteins such as serum albumin, gelatin, and immunoglobulin, amino acids such as glycine, glutamine, asparagine, arginine, and lysine, sugars such as polysaccharide and monosaccharide and carbohydrates, and sugar alcohols such as mannitol and sorbitol. When preparing aqueous solutions for injection, for example, solubilizing agents include physiological saline, isotonic solutions containing glucose and other adjunctive agents such as D-sorbitol, D-mannose, D-mannitol, and sodium chloride, and may be used in combination with appropriate solubilizing agents such as alcohol (ethanol etc.), polyalcohol (propylene glycol, PEG etc.), and non-ionic surfactant (polysorbate 80, HCO-50 etc.).

Further, if necessary, antibodies of the present invention may be encapsulated into microcapsuls (microcapsuls made of hydroxymethyl cellulose, gelatin, poly(methyl methacrylate), etc.), or included in a colloidal drug delivery system (liposome, albumin microsphere, microemulsion, nanoparticle, and nanocapsule, etc.) (see "Remington's Pharmaceutical Science 16th edition", Oslo Ed. (1980) etc.). Methods for formulating sustained-release drugs are also known, and can be applied to antibodies of the present invention (Langer et al., J.Biomed.Mater.Res. 15: 267-277 (1981); Langer, Chemtech. 12: 98-105 (1982); U.S. Pat. No. 3,773,919; European Patent Application No (EP): 58,481; Sidman et al., Biopolymers 22: 547-556 (1983); EP133,988).

Antibodies or pharmaceutical compositions of the present invention can be used in combination with blood coagulation factor VIII. Antibodies or pharmaceutical compositions of the present invention may be administered with blood coagulation factor VIII simultaneously or with some interval between them. Administration may be performed in a kit that combines an antibody or pharmaceutical composition of the present invention with blood coagulation factor VIII. When an antibody or pharmaceutical composition of the present invention is used in combination with blood coagulation factor VIII, if desired, it is also possible to use dosages lower than when they are used alone.

Although the dosage of the pharmaceutical compositions of the present invention is appropriately determined considering the type of formulation, method of administration, age and body weight of patients, symptoms of patients, type and progress of disease, etc., and ultimately by doctors, generally, doses of 0.1 to 2000 mg/day can be divided into one to several administrations for adults. The dosage is preferably 1 to 1000 mg/day, more preferably 5 to 500 mg/day, and most preferably 100 to 300 mg/day. Although the dosage varies according to the body weight and age of patients, administration methods and such, one skilled in the art can suitably select an appropriate dosage. Preferably, the dosing period is also appropriately determined according to, for example, the healing process of patients.

Further, it is also possible to perform gene therapy by inserting a gene encoding an antibody of the present invention into gene therapy vectors. As an administration method apart from direct administration of naked plasmids, the genes may be administered by packaging into liposome and such, or insertion into various virus vectors such as retrovirus vector, adenovirus vectors, vaccinia virus vectors, pox virus vectors, adeno-associated virus vectors, and HVJ vectors (see Adolph "Virus Genome Method" C RC Press, Florid (1996)), or by coating onto carrier beads such as colloidal gold particle (WO93/17706 etc.). However, the gene may be administered by any methods, as long as the antibody can be expressed in vivo to exert its action. Preferably, a sufficient dose is administered through an appropriate parenteral route, such as intravenous, intraperitoneal, subcutaneous, intracutaneous, intra-adipose tissue, intramammary, and intramuscular injection and infusion, inhalation, gas-inducible particle bombardment method (with an electron gun and such), or mucosal route using nasal drop. Genes encoding an antibody of the present invention may be administered by introducing the gene into blood cells, cells derived from bone marrow and such, using ex vivo liposome transfection, particle bombardment method (U.S. Pat. No. 4,945,050) or virus infection, and re-introducing these cells into animals. In gene therapy, any gene encoding an antibody of the present invention, for example, genes comprising nucleotide sequences of CDRs of the above-described XB12, SB04, A44, and B26 may be used.

The present invention also provides methods for preventing and/or treating bleeding, disorders accompanied by bleeding, or disorders caused by bleeding, comprising the steps of administering an antibody or composition of this invention. Antibodies or compositions can be administered, for example, by the aforementioned methods.

The present invention also relates to use of the antibodies of this invention for manufacturing (pharmaceutical) compositions of this invention.

Further, the present invention provides kits comprising at least an antibody or composition of this invention to be used in the above-described methods. Glass syringe, injection needle, pharmaceutically acceptable medium, alcohol cotton, bandage, instruction manual that describes the usage, or such may also be optionally packaged into the kits.

All documents of prior arts cited in the present specification have been incorporated herein by reference.

Herein below, the present invention will be specifically described with reference to Examples, but it is not to be construed as being limited thereto.

EXAMPLE 1

Preparation of Non-neutralizing Antibody Against Factor IXa (F.IXa)

1-1. Immunization and Preparation of Hybridomas

Eight BALB/c mice (male, 6 weeks old when immunization was initiated (Charles River, Japan)) and five MRL/lpr mice (male, 6 weeks old when immunization was initiated (Charles River, Japan)) were immunized with human factor IXaβ (Enzyme Research Laboratories, Inc.) as described below. As an initial immunization, factor IXaβ (40 μg/head) emulsified with FCA (Freund's complete adjuvant H37 Ra (Difco laboratories)) was subcutaneously administered. Two weeks later, factor IXaβ (40 μg/head) emulsified with FIA (Freund's incomplete adjuvant (Difco laboratories)) was subcutaneously administered. Afterward, three to seven booster immunizations were performed at one week intervals. After the titer of a plasma antibody against factor IXaβ was confirmed to be elevated by ELISA (Enzyme linked immunosorbent assay) described in 1-2, factor IXaβ (40 μg/head) diluted in PBS(−) (phosphate buffered saline free of calcium ion and magnesium ion) was intravenously administered as a final immunization. Three days after the final immunization, spleens were excised from mice. While a portion thereof was used in Example 10-2, the remaining spleen cells were fused with mouse myeloma cells P3X63Ag8U.1 (referred to as P3U1, ATCC CRL-1597) by a standard method using PEG1500 (Roche Diagnosticks). Fused cells suspended in RPMI1640 medium (Invitrogen) containing 10% FBS (Invitrogen) (hereinafter referred to as 10% FBS/RPMI1640) were seeded in a 96-well culture plate, and 1, 2, 3, and 5 days after the fusion, the medium was replaced with a HAT selection medium (10% FBS/RPMI1640/2% HAT 50× concentrate (Dainippon Pharmaceutical Co. Ltd)/5% BM-Condimed H1 (Roche Diagnostics) to selectively culture hybridomas. Using the supernatants collected on the $8^{th}$ or $9^{th}$ day after fusion, factor IXa-binding activity was measured by ELISA described in 1-2 to select hybridomas having factor IXa-binding activity. Subsequently, the activity of neutralizing factor IXa enzymatic activity was measured by the method described in 1-3 to select hybridomas that do not have factor IXa-neutralizing activity. Hybridomas were cloned twice by performing limiting dilutions in which one cell is seeded in each well of a 96-well culture plate. Single colony cells confirmed by microscopic observation were subjected to ELISA and neutralization activity assay as described in 1-2 and 1-3 was performed for clone selection. Ascites containing the cloned antibody was prepared by the method described in 1-4, and the antibody was purified from the ascites. The purified antibody was unable to extend APTT (activated partial thromboplastin time) and this was confirmed by the method described in 1-5.

1-2. Factor IXa ELISA

Factor IXaβ was diluted to 1 μg/mL with a coating buffer (100 mM sodium bicarbonate, pH 9.6, 0.02% sodium azide) and distributed in Nunc-Immuno plate (Nunc-Immuno™ 96 MicroWell™ plates MaxiSorp™ (Nalge Nunc International)) at 100 μL/well. Then, the plate was incubated at 4° C. overnight. After washing the plate with PBS(−) containing Tween® 20 thrice, it was blocked with a diluent buffer (50 mM Tris-HCl, pH 8.1, 1% bovine serum albumin, 1 mM $MgCl_2$, 0.15 M NaCl, 0.05% Tween® 20, 0.02% sodium azide) at room temperature for 2 hours. After removal of the buffer, a diluent buffer-diluted mouse antiserum or hybridoma. culture supernatant was added at 100 μL/well, and incubated at room temperature for 1 hour. After washing the plate thrice, alkaline phosphatase-labeled goat anti-mouse IgG (H+L) (Zymed Laboratories) which had been diluted to 1/2000 with the diluent buffer was added at 100 μL/well, and incubated at room temperature for 1 hour. After washing the plate six times, a colorimetric substrate Blue-Phos™ Phosphate Substrate (Kirkegaad & Perry Laboratories) was added at 100 μL/well, and incubated at room temperature for 20 minutes. After adding the Blue-Phos™ Stop Solution (Kirkegaad & Perry Laboratories) (100 μL/well), absorbance at 595 nm was measured with a Model 3550 Microplate Reader(Bio-Rad Laboratories).

1-3. Measurement of Factor IXa Neutralizing Activity

Phospholipid (Sigma-Aldrich) was dissolved in distilled water for injection, and ultrasonicated to prepare a phospholipid solution (400 μg/mL). Tris buffered saline containing 0.1% bovine serum albumin (hereinafter abbreviated as TBSB) (40 μL), 30 ng/mL factor IXaβ (Enzyme Research Laboratories) (10 μL), 400 μg/mL phospholipid solution (5 μL), TBSB containing 100 mM $CaCl_2$ and 20 mM $MgCl_2$ (5 μL), and hybridoma culture supernatant (10 μL) were mixed in a 96-well plate, and incubated at room temperature for 1 hour. To this mixed solution, 50 μg/mL factor X (Enzyme Research Laboratories) (20 μL) and 3 U/mL factor VIIIa (American diagnostica) (10 μL) were added and reacted at room temperature for 30 minutes. The reaction was stopped by adding 0.5 M EDTA (10 µL). After addition of an S-2222 solution (50 µL; Chromogenix) and incubation at room temperature for 30 minutes, the absorbance was measured at measurement wavelength 405 nm and reference wavelength 655 nm on a Model 3550 Microplate Reader (Bio-Rad Laboratories, Inc.).

1-4. Ascites Preparation and Antibody Purification

Ascites of the established hybridomas was produced according to standard procedures. That is, the hybridoma was cultured in vitro ($2\times10^6$) and transplanted into the peritoneal cavity of a BALB/c mouse (male, 5 to 7 weeks old at the time experiment was started, Japan Charles River) or BALB/c nude mouse (female, 5 to 6 weeks old at the time experiment was started, Japan Charles River and Japan CLEA), which was intraperitoneally administered twice with pristane (2,6,10,14-tetramethylpentadecane, WAKO Pure Chemical Industries) in advance. One to four weeks after the transplantation, ascites was collected from the mouse with an inflated abdomen.

The antibody was purified from the ascites using a Protein G Sepharose™ 4 Fast Flow column (Amersham Biosciences). The ascites was diluted 2-fold with a binding buffer (20 mM sodium acetate, pH 5.0) and applied to the column, which had been washed with 10 column volumes of the binding buffer. The antibody was eluted with 5 column volumes of an elution buffer (0.1 M glycine-HCl, pH 2.5), and neutralized with a neutralizing buffer (1 M Tris-HCl, pH 9.0). The resulting solution was concentrated using a Centriprep™ 10 (Millipore), and the solvent was replaced with TBS (50 mM Tris-buffered saline). The antibody concentration was calculated from the absorbance at 280 nm with A (1%, 1 cm)=13.5. Absorbance was measured with DU-650 (Beckman Coulter).

1-5. Measurement of APTT (Activated Partial Thromboplastin Time)

APTT was measured with a CR-A (Amelung)-connected KC10A (Amelung). A mixture of the TBSB-diluted antibody solution (50 µL), standard human plasma (Dade Behring) (50 µL), and APTT reagent (Dade Behring) (50 µL) was warmed at 37° C. for 3 minutes. To this mixture, 20 mM $CaCl_2$ (Dade Behring) (50 µL) was added to start a coagulation reaction, and the coagulation time was measured.

EXAMPLE 2

Preparation of Non-factor X (F.X)-neutralizing Antibody 2-1. Immunization and Hybridoma Preparation Eight BALB/c mice (male, 6 weeks old when immunization was initiated, Japan Charles River) and five MRL/lpr mice (male, 6 weeks old when immunization was initiated, Japan Charles River) were immunized with human factor X (Enzyme Research Laboratories) as described below. As an initial immunization, factor X (40 µg/head) emulsified with FCA was subcutaneously administered. Two weeks later, factor X (20 or 40 µg/head) emulsified with FIA was subcutaneously administered. Subsequently, three to six booster immunizations were given at one week intervals. After the titer of a plasma antibody against factor X was confirmed to be elevated by ELISA as described in 2-2, factor X (20 or 40 µg/head) diluted in PBS (−) was administered intravenously as a final immunization. Three days after the final immunization, mouse spleens were excised. While a portion thereof was used in Example 10-2, the remaining spleen cells were fused with mouse myeloma P3U1 cells, according to a standard method using PEG1500. Fused cells suspended in 10% FBS/RPMI1640 medium were seeded in a 96-well culture plate, and hybridomas were selectively cultured by replacing the medium with a HAT selection medium 1, 2, 3 and 5 days after the fusion. Binding activity toward factor X was measured by ELISA described in 2-2, using the culture supernatant collected on the $8^{th}$ day after fusion. Hybridomas having factor X-binding activity were selected, and their activities to neutralize factor Xa enzymatic activity were measured by the method described in 2-3. Hybridomas that do not have a neutralizing activity toward factor Xa were cloned by performing limiting dilution twice. Ascites containing the cloned antibody was prepared by the method described in 1-4, and the antibody was purified from the ascites. The purified antibody was unable to extend APTT and this was confirmed by the method described in 1-5.

2-2. Factor X ELISA

Factor X was diluted to 1 µg/mL with a coating buffer, and dispersed into Nunc-Immuno plate at 100 µL/well. Then the plate was incubated at 4° C. overnight. After washing the plate with PBS (−) containing Tween® 20 thrice, it was blocked with a diluent buffer at room temperature for 2 hours. After removal of the buffer, a diluent buffer-diluted mouse antiserum or hybridoma culture supernatant was added to the plate, and incubated at room temperature for 1 hour. After washing the plate thrice, alkaline phosphatase-labeled goat anti-mouse IgG (H+L) which had been diluted to 1/2000 with the diluent buffer was added, and incubated at room temperature for 1 hour. After washing the plate six times, a colorimetric substrate Blue-Phosr™ Phosphate Substrate (Kirkegaad & Perry Laboratories) was added at 100 µL/well, and incubated at room temperature for 20 minutes. After adding Blue-Phos™ Stop Solution (Kirkegaad & Perry Laboratories) (100 µL/well), absorbance ate 595 nm was measured with a Model 3550 Microplate Reader (Bio-Rad Laboratories).

2-3. Measurement of Factor Xa-neutralizing Activity

Hybridoma culture supernatant diluted to 1/5 with TBSB (10 µL) was mixed with 40 µL of TBCP (TBSB containing 2.78 mM $CaCl_2$ and 22.2 µM phospholipids (phosphatidyl choline:phosphatidyl serine=75:25, Sigma-Aldrich) containing 250 µg/mL factor Xa (Enzyme Research Laboratories), and incubated at room temperature for 1 hour. To this mixed solution, TBCP (50 µL) containing prothrombin (Enzyme Research Laboratories) (20 µg/mL) and 100 ng/mL activated coagulation factor V (factor Va (Haematologic Technologies)) were added, and reacted at room temperature for 10 minutes. The reaction was stopped by adding 0.5 M EDTA (10 µL). To this reaction solution, 1 mM S-2238 solution (Chromogenix) (50 µL) was added, and after incubation at room temperature for 30 minutes, absorbance at 405 nm was measured with a Model 3550 Microplate Reader (Bio-Rad Laboratories).

EXAMPLE 3

Construction of Chimera Bispecific Antibody Expression Vector 3-1. Preparation of Antibody Variable Region-encoding DNA Fragments from Hybridomas From the hybridomas that produce anti-F.IXa antibody or anti-F.X antibody, total RNA was extracted using the QIAGEN® RNeasy® Mini Kit (QIAGEN) according to the method described in the instruction manual. The total RNA was dissolved in sterile water (40 µL). Single-stranded cDNA was synthesized by RT-PCR using the SuperScript cDNA synthesis system (Invitrogen) with the purified RNA (1 to 2 µg) as template, according to the method described in the instruction manual.

3-2. PCR Amplification of Antibody H Chain Variable Region and Sequence Analysis As primers for amplifying the mouse antibody H chain variable region (VH) cDNA, an HB primer mixture and HF primer mixture described in the report by Krebber et al. (J. Immunol. Methods 1997; 201: 35-55) were prepared. Using 0.5 µL each of the 100 µM HB primer mixture and 100 µM HF primer mixture, a reaction solution (25 µL) (cDNA solution prepared in 3-1 (2.5 µL), KOD plus buffer (TOYOBO), 0.2 mM dNTPs, 1.5 mM $MgCl_2$, 0.75 units DNA polymerase KOD plus (TOYOBO)) was prepared. Using a thermal cycler Gen-eAmp PCR system 9700 (Parkin Elmer), PCR was performed according to amplification efficiency of the cDNA fragments, either under conditions A (3 min heating at 98° C. followed by 32 cycles of reaction (98° C., 20 sec, 58° C., 20 sec, and 72° C., 30 sec in one cycle)) or conditions B (3 min heating at 94° C. followed by 5 cycles of reaction (94° C., 20 sec, 46° C., 20 sec, and 68° C., 30 sec in one cycle) and 30 cycles of reaction (94° C., 20 sec, 58° C., 20 sec, and 72° C., 30 sec in one cycle)). After PCR, the reaction solution was subjected to 1% agarose gel electrophoresis. Amplified fragments of the desired size (about 400 bp) were purified using a QIAquick Gel Extraction Kit (QIAGEN) according to the methods described in the attached instruction manual, and eluted with sterile water (30 µL). Nucleotide sequences of the DNA fragments were determined using a BigDye Terminator Cycle Sequencing Kit (Applied Biosystems) on a DNA sequencer ABI PRISM 3100 Genetic Analyzer (Applied Biosystems), according to the method described in the attached instruction manual. Sequence groups determined by this method were comparatively analyzed using an analytical software, GENETYX-SV/RC Version 6.1 (Genetyx), and DNAs with different sequences were selected.

3-3. Preparation of Antibody Variable Region DNA Fragments for Cloning

The following procedure was performed to add restriction enzyme Sfi I cleavage sites for cloning to both termini of the antibody variable region amplification fragments.

To amplify the VH fragments added with an Sfi I cleavage site (Sfi I-VH), a primer (primer VH-5' end) in which the primer HB (Gly4Ser)2-linker sequence was replaced with a sequence containing Sfi I cleavage site (SEQ ID NO: 5) was prepared. Using 0.5 µL each of the 10 µM sequence-specific primer VH-5' end and 10 µM primer scfor (J. Immunol. Methods 1997; 201: 35-55), a reaction solution (20 µL) (purified solution of VH cDNA amplification fragment prepared in 3-2 (1 µL), KOD plus buffer (TOYOBO), 0.2 mM dNTPs, 1.5 mM $MgCl_2$, 0.5 units DNA polymerase KOD plus (TOYOBO)) was prepared. Using a thermal cycler GeneAmp PCR system 9700 (Parkin Elmer), PCR was performed according to amplification efficiency of the cDNA fragments, either under conditions A (3 min heating at 98° C. followed by 32 cycles of reaction (98° C., 20 sec, 58° C., 20 sec, and 72° C., 30 sec in one cycle)) or conditions B (3 min heating at 94° C. followed by 5 cycles of reaction (94° C., 20 sec, 46° C., 20 sec, and 68° C., 30 sec in one cycle) and 30 cycles of reaction (94° C., 20 sec, 58° C., 20 sec, and 72° C., 30 sec in one cycle)). After PCR, the reaction solution was subjected to 1% agarose gel electrophoresis. Amplified fragments of the desired size (about 400 bp) were purified using a QIAquick Gel Extraction Kit (QIAGEN) by the method described in the attached instruction manual, and eluted with sterile water (30 µL).

To amplify the mouse antibody L chain variable region (VL) cDNA fragments, 0.5 µL each of the 100 µM LB primer mixture and 100 µM LF primer mixture described in the report by Krebber et al. (J. Immunol. Methods 1997; 201: 35-55) was first used, and a reaction solution (25 µL) (cDNA solution prepared in 3-1 (2.5 µL), KOD plus buffer (TOYOBO), 0.2 mM dNTPs, 1.5 mM $MgCl_2$, 0.75 units DNA polymerase KOD plus (TOYOBO)) was prepared. Using a thermal cycler GeneAmp PCR system 9700 (Parkin Elmer), PCR was performed according to amplification efficiency of the fragments, under conditions of 3 minutes heating at 94° C. followed by 5 cycles of reaction (94° C., 20 sec, 46° C., 20 sec, and 68° C., 30 sec in one cycle) and 30 cycles of reaction (94° C., 20 sec, 58° C., 20 sec, and 72° C., 30 sec in one cycle). After PCR, the reaction solution was subjected to 1% agarose gel electrophoresis. Amplified fragments of the desired size (about 400 bp) were purified using the QIAquick Gel Extraction Kit (QIAGEN) by the method described in the attached instruction manual, and eluted with sterile water (30 µL). The fragments are in a state in which the primer LF-derived (Gly4Ser)3-linker sequence is added to their C termini. In order to add an Sfi I cleavage site to the C termini of the fragments, a primer (primer VL-3' end) in which the primer LF (Gly4Ser)3-linker sequence was replaced with a sequence having Sfi I cleavage site (SEQ ID NO: 6) was prepared. To amplify the VL fragments added with an Sfi I cleavage site (Sfi I-VL), 0.5 µL each of the 10 µM VL-3' end primer mixture and 10 µM scback primer was used, and a reaction mixture (20 µL) (purified solution of VL cDNA amplification fragment (1 µL), KOD plus buffer (TOYOBO), 0.2 mM dNTPs, 1.5 mM $MgCl_2$, 0.5 units DNA polymerase KOD plus (TOYOBO)) was prepared. PCR was performed using a thermal cycler GeneAmp PCR system 9700 (Parkin Elmer) under conditions of 3-minutes heating at 94° C. followed by 5 cycles of reaction (94° C., 20 sec, 46° C., 20 sec, and 68° C., 30 sec in one cycle) and 30 cycles of reaction (94° C., 20 sec, 58° C., 20 sec, and 72° C., 30 sec in one cycle). After PCR, the reaction solution was subjected to 1% agarose gel electrophoresis. Amplified fragments of the desired size (about 400 bp) were purified using the QIAquick Gel Extraction Kit (QIAGEN) by the method described in the attached instruction manual, and eluted with sterile water (30 µL).

The purified Sfi I-VH and Sfi I-VL fragments were digested with Sfi I (Takara Bio) at 50° C. overnight in a reaction solution prepared according to the method described in the attached instruction manual. Subsequently, the reaction solution was purified using a QIAquick PCR Purification Kit (QIAGEN) by the method described in the attached instruction manual, and eluted with Buffer EB (30 µL) included in the kit.

3-4. Bispecific IgG Antibody Expression Plasmid

When producing the bispecific IgG antibody of interest, the knobs-into-holes technique of IgG1 (Ridgway et al., Protein Eng. 1996; 9: 617-621) was referred to when preparing IgG4 with an amino acid-substituted CH3 portion to form heteromolecules for each H chain. Type a (IgG4γa) is substituted with Y349C and T366W, and type b (IgG4γb) is substituted with E356C, T366S, L368A, and Y407V. Further, a substitution (-ppcpScp-→-ppcpPcp-) was also introduced at the hinge regions of both types. Almost all the H chains become heteromolecules by this technique; however, this does not necessarily apply to L chains, and the formation of unnecessary antibody molecules may affect subsequent activity measurements. Therefore, to separately express the arms of each antibody molecule (called HL molecule), which have different specificities, and efficiently form the type of bispecific IgG antibody of interest within cells, those that are inducible by different drugs were used as the expression vectors for each HL molecule.

Figure 2:
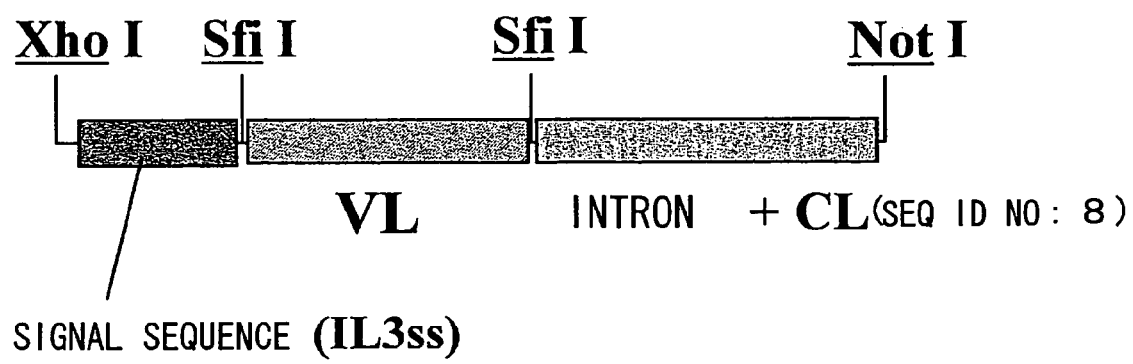
FIG. 2 depicts the insertion regions of pcDNA4-g4L and pIND-g4L.

As an expression vector for an arm of the antibody molecule (called right arm HL molecule for convenience), pcDNA4-g4H or pcDNA4-g4L (FIG. 1 or FIG. 2) was prepared, in which the respective H chain or L chain region, that is, an appropriate mouse antibody variable region (VH or VL) and a human IgG4γa constant region (SEQ ID NO: 7) or K constant region (SEQ ID NO: 8), were incorporated into the tetracycline-inducible type vector pcDNA4 (Invitrogen) downstream of the signal sequence (IL3ss) for animal cells (Proc. Natl. Acad. Sci. USA. 1984; 81: 1075). First, Eco RV and Not I (Takara Bio) were used to digest pcDNA4 at the restriction enzyme cleavage sites that are present in its multi-cloning site. The right arm H chain- or L chain-expression unit (about 1.6 kb or about 1.0 kb respectively) of a chimera bispecific antibody having appropriate antibody variable regions was digested with XhoI (Takara Bio). Then, it was purified with the QIAquick PCR Purification Kit (QIAGEN) by the method described in the attached instruction manual, and reacted with DNA polymerase KOD (TOYOBO) at 72° C. for 10 minutes in a reaction solution composition described in the attached instruction manual to blunt the ends. The blunt-end fragments were purified with the QIAquick PCR Purification Kit(QIAGEN) by the method described in the attached instruction manual, and digested with Not I (Takara Bio). The Not I/blunt end fragments (about 1.6 kb or 1.0 kb respectively) and the Eco RV/Not I-digested pcDNA4 were subjected to a ligation reaction using Ligation High (TOYOBO), according to the method described in the attached instruction manual. An *E. coli* DH5α strain (Competent high DH5α (TOYOBO)) was transformed with the above-described reaction solution. From the ampicillin-resistant clones thus obtained, respective plasmid DNAs were isolated using the QIAprep Spin Miniprep Kit (QIAGEN).

Figure 3:
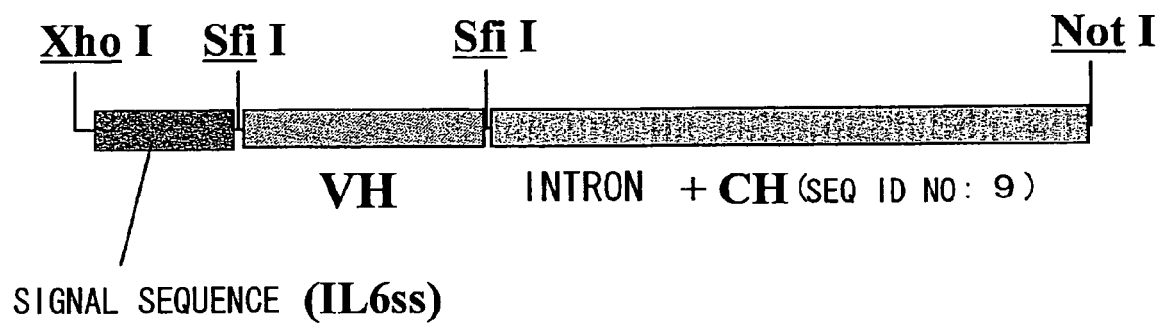
FIG. 3 depicts the insertion region of pIND-g4H.

As an expression vector for the antibody molecule's other arm (called left arm HL molecule for convenience), pIND-g4H or pIND-g4L (FIG. 2 or FIG. 3) was prepared according to the above-described method, in which the H chain or L chain respective region, that is, an appropriate mouse antibody variable region (VH or VL) and a human IgG4γb constant region (SEQ ID NO: 9) or κ constant region (SEQ ID NO: 8), were incorporated into the ecdysone analogue inducible type vector pIND (Invitrogen) downstream of the signal sequence (IL3ss) for animal cells (EMBO. J. 1987; 6: 2939), and the respective plasmid DNAs were isolated.

3-5. Construction of Bispecific Antibody Expression Vector

The tetracycline-inducible type expression plasmid prepared in 3-4 (pcDNA4-g4H or pcDNA4-g4L) was digested with Sfi I, and was subjected to 1% agarose gel electrophoresis. Fragments (about 5 kb) lacking the intrinsic antibody variable region part (VH or VL (see FIG. 1 or FIG. 2)) were purified using the QIAquick Gel Extraction Kit (QIAGEN) by the method described in the attached instruction manual, and eluted with sterile water (30 μL). The fragments, and the corresponding Sfi I-VH or Sfi-VL fragment derived from the Sfi I-digested anti-F.IXa antibody prepared in 3-3, were subjected to a ligation reaction using the Quick Ligation Kit (New England Biolabs) according to the method described in the attached instruction manual. An *E. coli* DH5α strain (Competent high DH5α (TOYOBO)) was transformed with the above-described reaction solution. Further, fragments obtained by removing the antibody variable region part by a similar technique as described above (VH or VL (see FIG. 2 or FIG. 3)) from the Sfi I-digested ecdysone analogue-inducible type expression plasmid (pIND-g4H or pIND-4GL) prepared in 3-4 and the corresponding Sfi I-digested anti-F.X antibody-derived Sfi I-VH or Sfi I-VL fragment were incorporated by a similar method.

In each of the ampicillin-resistant transformants thus obtained, insertion of the fragment of interest was confirmed by colony PCR method using primers that sandwich the inserted fragment. First, for the anti-F.IXa antibody chimeric H chain or L chain expression vector, a 21-mer CMVF primer (SEQ ID NO: 10) which anneals to the CMV forward priming site upstream of the insertion site, and an 18-mer BGHR primer (SEQ ID NO: 11) which anneals to the BGH reverse priming site downstream of the insertion site were synthesized (Sigma Genosys). For the anti-F.X antibody chimeric H chain or L chain expression vector, a 24-mer EcdF primer (SEQ ID NO: 12) which anneals to the upstream of the insertion site and an 18-mer BGHR primer (SEQ ID NO: 11) which anneals to the BGH reverse priming site downstream of the insertion site were synthesized (Sigma Genosys). For colony PCR, a reaction solution (20 μL) (0.2 μL primer (10 μM), KOD dash buffer (TOYOBO), 0.2 mM dNTPs, and 0.75 units DNA polymerase KOD dash) (TOYOBO)) was prepared. To this reaction solution, cells of the transformant strain were added in appropriate amounts and PCR was performed. PCR was performed using a thermal cycler Gene-Amp PCR system 9700 (Parkin Elmer) under conditions of 1 minute heating at 96° C. followed by 30 cycles of reaction (96° C., 10 sec, 55° C., 10 sec, and 72° C., 30 sec in one cycle). After PCR, the reaction solution was subjected to 1% agarose gel electrophoresis, and clones from which amplification fragments of the desired size were obtained, were selected. The PCR product was treated with an ExoSAP-IT (Amersham Biosciences) to inactivate excess primers and dNTPs according to the attached instruction manual. Nucleotide sequences of the DNA fragments were determined using a BigDye Terminator Cycle Sequencing Kit (Applied Biosystems) on a DNA sequencer ABI PRISM 3100 Genetic Analyzer (Applied Biosystems), according to the method described in the attached instruction manual. Sequence groups determined by the present method were analyzed with an analytical software, GENETYX-SV/RC Version 6.1 (Genetyx). For VH, clones of interest having no insertion, deletion, or mutation were selected. For VL, different from the P3U1-derived pseudo VL gene used in hybridomas, clones of interest having no insertion, deletion, or mutation were selected.

From the clones of interest, the respective plasmid DNAs were isolated by using a QIAprep Spin Miniprep Kit (QIAGEN), and then dissolved in sterile water (100 μL). Anti-F.IXa antibody chimeric H chain expression vector, anti-F.IXa antibody chimeric L chain expression vector, anti-F.X antibody chimeric H chain expression vector, and anti-F.X antibody chimeric L chain expression vector were named pcDNA4-g4D RaHn, pcDNA4-g4IXaLn, pIND-g4XHn, and pIND-g4XLn, respectively. Each plasmid solution was stored at 4° C. till use.

EXAMPLE 4

Expression of Chimera Bispecific Antibodies in Animal Cells 4-1. Preparation of DNA Solutions Expression of the antibody's right arm HL molecule expression vectors (pcDNA4-g4IXaHn and pcDNA4-g4IXaLn) is induced by tetracycline. In the absence of tetracycline, Tet repressor-encoding plasmid pcDNA6/TR (Invitrogen) is required to completely suppress their expressions.

Further, expression of the left arm antibody HL molecule expression vectors (pINE-g4XHn and pIND-g4XLn) was induced by an insect hormone ecdysone analogue (ponasterone A). This requires plasmid pVgRXR (Invitrogen) which encodes the ecdysone receptor and retinoid X receptor that react with ponasterone A and induce expression. Therefore, for the transfection of animal cells, a mixture of six types of plasmid DNAs in total was prepared. For 1 mL of cell culture, pcDNA4-g4IXaHn, pcDNA4-g4IXaLn, pIND-g4XHn and pIND-g4XLn (218.8 ng each), as well as pcDNA6/TR and pVgRXR (1312.5 ng each) were used.

4-2. Transfection of Animal Cells

Human fetal renal carcinoma cell-derived HEK293H strain (Invitrogen) was suspended in a DMEM culture medium (Invitrogen) containing 10% FCS (MOREGATE), and 1 mL of which was seeded at a cell density of $5 \times 10^5$ cells/mL in each well of a 12-well plate for adhesive cells (CORNING) and cultured in a $CO_2$ incubator (37° C., 5% $CO_2$). The plasmid DNA mixture prepared in 4-1 was added to a mixture of transfection reagents, Lipofectaine 2000 (Invitrogen) (7 µL) and Opti-MEM I medium (Invitrogen) (250 µL), and left to stand at room temperature for 20 minutes. The resulting mixture was added to the cells in each well and incubated for 4 to 5 hours in a $CO_2$ incubator (37° C., 5% $CO_2$).

4-3. Induction of Bispecific IgG Antibody Expression

Culture medium was removed by suction from the transfected cell culture described above, and then 1 mL of a CHO-S-SFM-II (Invitrogen) medium containing 1 µg/mL tetracycline (Wako Pure Chemical Industries) was added. The resulting mixture was incubated for one day in a $CO_2$ incubator (37° C., 5% $CO_2$) to induce primary expression of the antibody's right arm HL molecule. Subsequently, after removing the medium by suction, washing with 1 mL of CHO-S-SFM-II medium, and adding 1 mL of a CHO-S-SFM-II medium containing 5 µM ponasterone A (Invitrogen), the mixture was incubated in a $CO_2$ incubator (37° C., 5% $CO_2$) for 2 to 3 days, and secondary expression of the antibody's left arm HL molecule was induced so that the bispecific IgG antibody was secreted into the medium. The culture supernatant was recovered and centrifuged (about 2000 g, 5 min, room temperature) to remove the cells, and concentrated using Microcon® YM-50 (Millipore), if necessary. The sample was stored at 4° C. till use.

EXAMPLE 5

Quantification of Human IgG Concentration

Goat affinity purified antibody to human IgG Fc (Cappel) was adjusted to 1 µg/mL with a coating buffer, and immobilized to a Nunc-Immuno plate. After blocking with a diluent buffer (D.B.), a sample of the culture supernatant suitably diluted with D.B. was added. Further, as a standard for calculating the antibody concentration, human IgG4 (humanized anti-TF antibody, see WO 99/51743) diluted with D.B. in a two-fold dilution series up to 11 stages beginning at 1000 ng/mL was similarly added. After three washes, goat anti-human IgG alkaline phosphatase (Biosource International) was reacted. After five washes, the plate was color developed using the Sigma 104® phosphatase substrate (Sigma-Aldrich) as a substrate, and the absorbance at 405 nm was measured on an absorbance reader Model 3550 (Bio-Rad Laboratories) with a reference wavelength of 655 nm. Using the Microplate Manager III (Bio-Rad Laboratories) software, human IgG concentration in the culture supernatant was calculated from the standard curve.

EXAMPLE 6

F.VIIIa (Activated Coagulation Factor VIII)-mimetic Activity Assay

The F.VIIIa-mimetic activity of a bispecific antibody was assessed by the following enzymatic assay. The following reactions were all performed at room temperature. A mixture of 40 µL factor IX (3.75 µg/mL; Enzyme Research Laboratories) and 10 µL of the antibody solution was incubated in a 96-well plate for 1 hour. Then,10 µL factor XIa (10 ng/mL; Enzyme Research Laboratories), 20 µL factor X (50 µg/mL; Enzyme Research Laboratories), 5 µL phospholipid (400 µg/mL; see Examples 1-3), and 15 µL TBSB containing 5 mM $CaCl_2$ and 1 mM $MgCl_2$ (hereinafter abbreviated as TBSB-S) were added to initiate enzymatic reaction. After 30 minutes, the reaction was stopped by adding 10 µL of 0.5 M EDTA.

Figure 4:
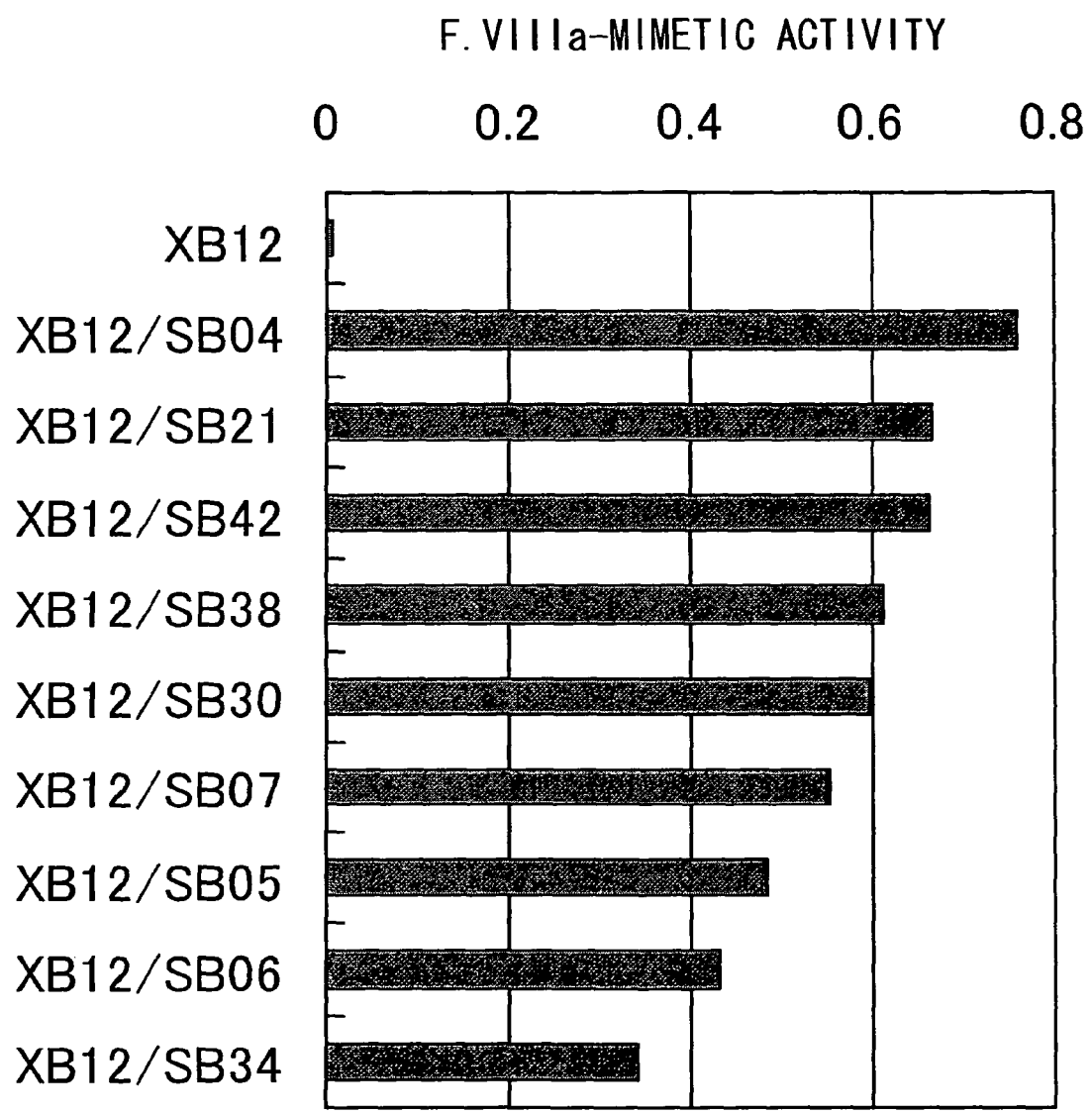
FIG. 4 depicts results of measuring the F.VIIIa-mimetic activity of an anti-F.IXa/anti-F.X bispecific antibody, generated from anti-F.IXa antibody XB12 and anti-F.X antibody SB04, SB21, SB42, SB38, SB30, SB07, SB05, SB06, or SB34. The concentration of the antibody solutions was 10 μg/mL (final concentration 1 μg/mL). The result is nine types of bispecific antibodies that showed an increase in the F.VIIIa-mimetic activity: XB12/SB04, XB12/SB21, XB12/SB42, XB12/SB38, XB12/SB30, XB12/SB07, XB12/SB05, XB12/SB06, and XB12/SB34, in the order of activity strength.
Figure 5:
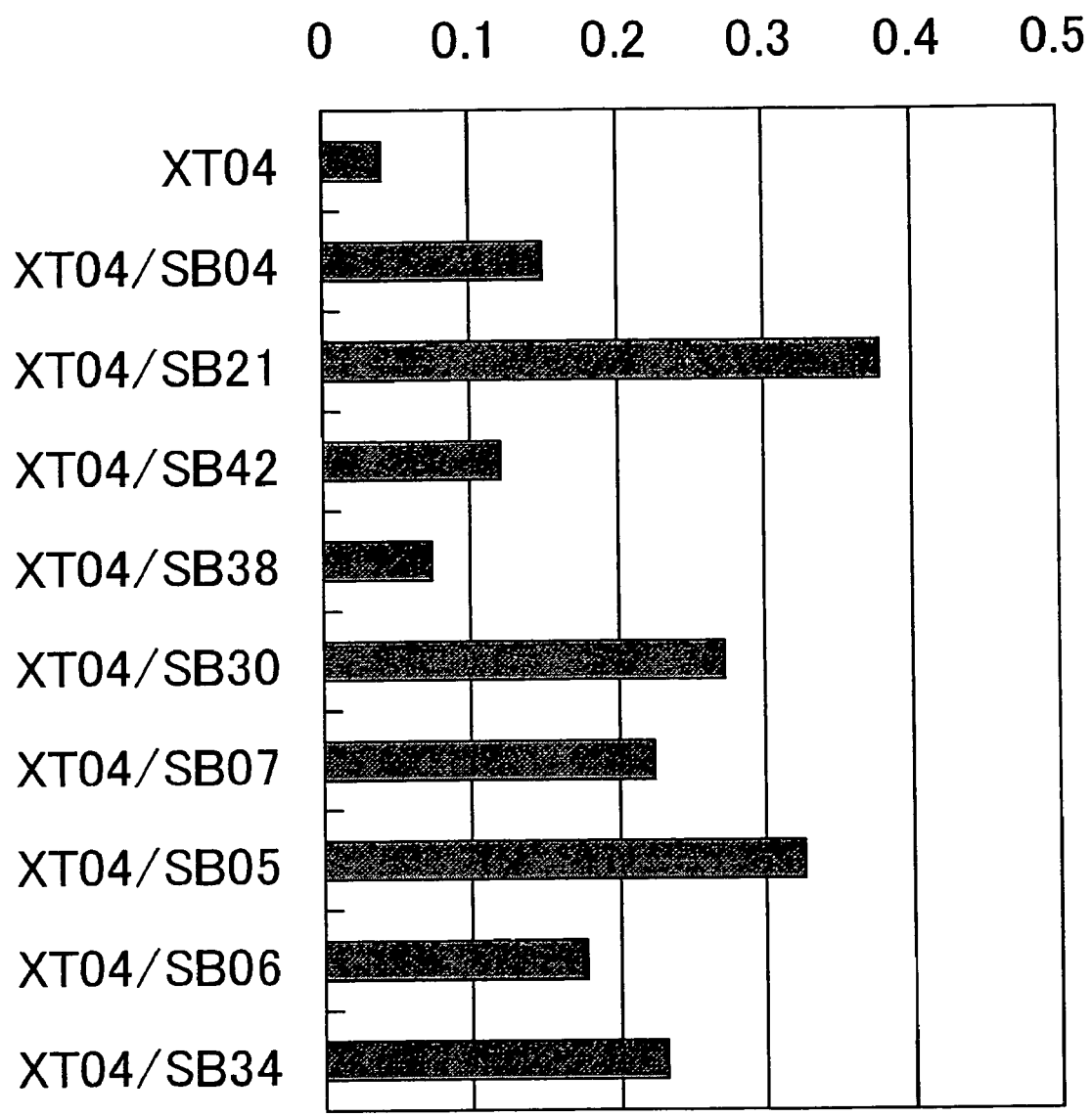
FIG. 5 depicts results of measuring the F.VIIIa-mimetic activity of an anti-F.IXa/anti-F.X bispecific antibody generated from anti-F.IXa antibody XT04 and anti-F.X antibody SB04, SB21, SB42, SB38, SB30, SB07, SB05, SB06, or SB34. The concentration of the antibody solutions was 10 μg/mL (final concentration 1 μg/mL). As a result, XT04/SB04, XT04/SB21, XT04/SB42, XT04/SB38, XT04/SB30, XT04/SB07, XT04/SB05, XT04/SB06, and XT04/SB34 showed an increase in the F.VIIIa-mimetic activity.

After adding a colorimetric substrate solution (50 µL) to each well, absorbance at 405 nm (reference wavelength 655 nm) at 0 and 30 minutes was measured with a Model 3550 Microplate Reader (Bio Rad Laboratories). The F.VIIIa-mimetic activity was presented as a value obtained by subtracting the value of absorbance change in 30 minutes without antibody addition from that with the antibody addition (see FIG. 4 and FIG. 5).

TBSB was used as a solvent for phospholipids, while TBSB-S was used as a solvent for factor XIa, factor IX, and factor X. The calorimetric substrate solution was a 1:1 mixture of "Tesutochiinu" colorimetric substrate S-2222 (Chromogenix) dissolved according to the attached instruction manual and a polybrene solution (0.6 mg/L hexadimethrine bromide (Sigma)).

Figure 6:
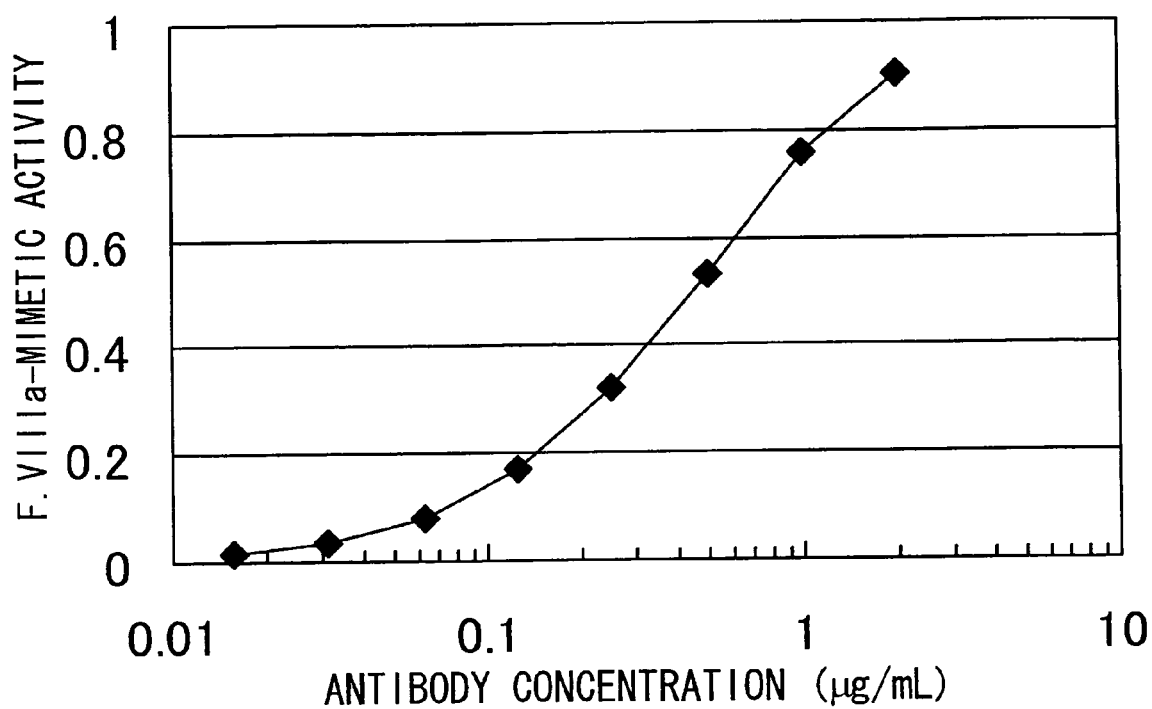
FIG. 6 depicts results of measuring the F.VIIIa-mimetic activity of various concentrations of XB12/SB04, which showed the highest activity in FIG. 4. As a result, XB12/SB04 showed a concentration-dependent increase of F.VIIIa-mimetic activity.

Further, the concentration dependency of XB12/SB04's F.VIIIa-mimetic activity, which was the highest among all, was measured (FIG. 6).

EXAMPLE 7

Plasma Coagulation Assay

Figure 7:
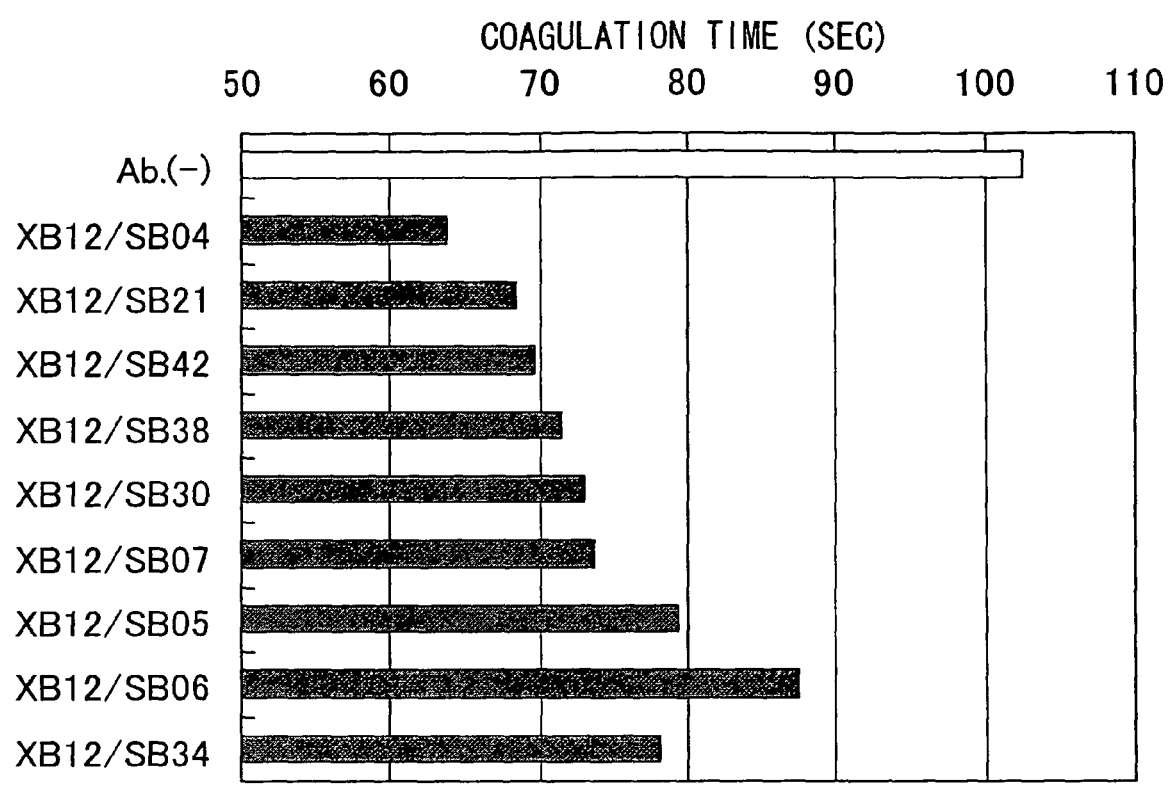
FIG. 7 depicts results of measuring the plasma coagulation time (APTT) in the presence of XB12/SB04, XB12/SB21, XB12/SB42, XB12/SB38, XB12/SB30, XB12/SB07, XB12/SB05, XB12/SB06, or XB12/SB34. The concentration of the antibody solutions mixed with F.VIII-deficient plasma was 1.7 μg/mL for XB12/SB06 and 10 μg/mL for the rest. As a result, XB12/SB04, XB12/SB21, XB12/SB42, XB12/SB38, XB12/SB30, XB12/SB07, XB12/SB05, XB12/SB06, and XB12/SB34 showed a coagulation time shortening effect compared with in the absence of the antibodies.
Figure 8:
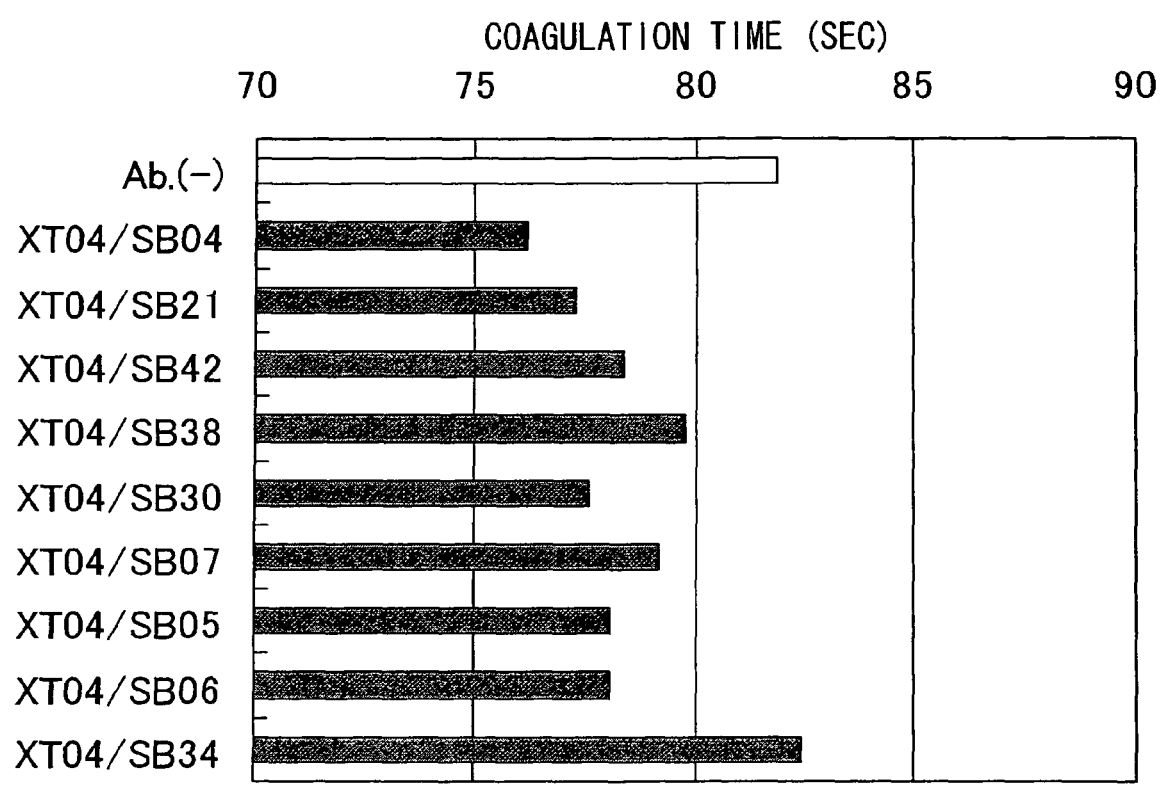
FIG. 8 depicts results of measuring the plasma coagulation time (APTT) in the presence of XT04/SB04, XT04/SB21, XT04/SB42, XT04/SB38, XT04/SB30, XT04/SB07, XT04/SB05, XT04/SB06, and XT04/SB34. The concentration of the antibody solutions mixed with F.VIII-deficient plasma was 5 μg/mL for XT04/SB06 and 10 μg/mL for the rest. As a result, XT04/SB04, XT04/SB21, XT04/SB42, XT04/SB38, XT04/SB30, XT04/SB07, XT04/SB05, and XT04/SB06 showed a coagulation time shortening effect compared with in the absence of the antibodies. XT04/SB34 showed no coagulation time shortening effect.

To elucidate whether a bispecific antibody corrects the coagulation ability of hemophilia A blood, effects of the bispecific antibody on activated partial thromboplastin time (APTT) were examined using F.VIII-deficient plasma. A mixed solution comprising an antibody solution at various concentrations (50 µL), F.VIII-deficient plasma (50 µL; Biomerieux), and APTT reagent (50 µL; Dade Behring) was warmed at 37° C. for 3 minutes. Coagulation reaction was initiated by adding 20 mM $CaCl_2$ (50 µL; Dade Behring) to the above-described mixture. The time required for coagulation was measured with CR-A (Amelung)-connected KC10A (Amelung) (FIG. 7 and FIG. 8).

Figure 9:
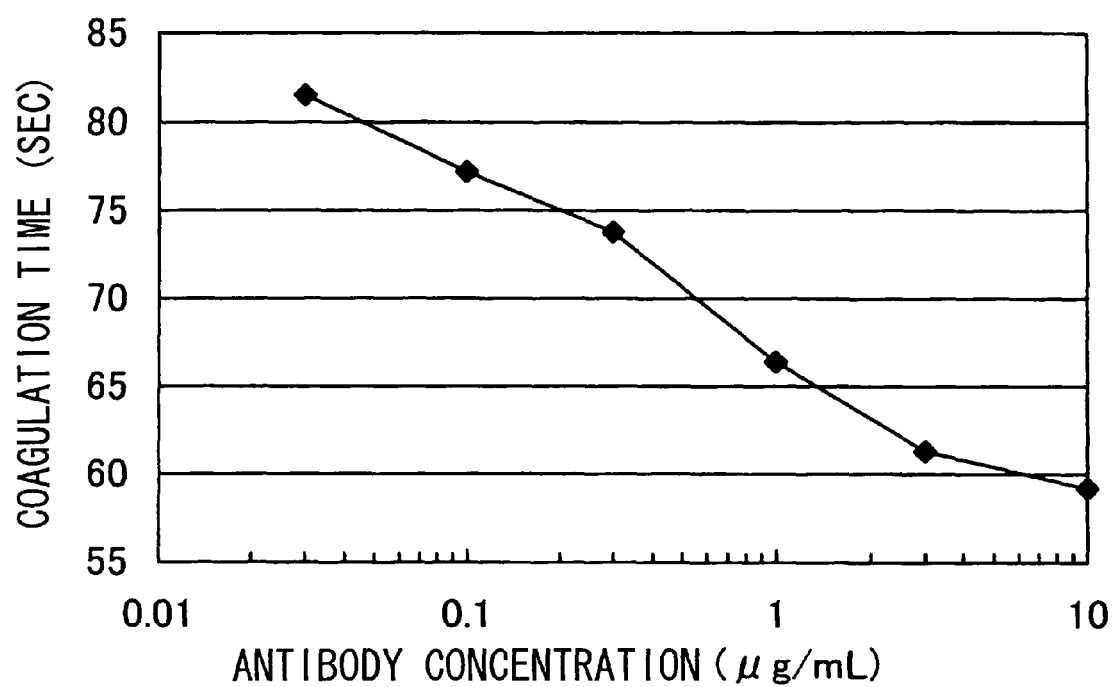
FIG. 9 depicts results of measuring the coagulation time with various concentrations of XB12/SB04, which showed the highest coagulation time (APTT) shortening effect in FIGS. 7 and 8. As a result, XB12/SB04 showed a concentration-dependent effect of shortening the coagulation time. The antibody concentration in the figure shows values of the antibody solution mixed with F.VIII-deficient plasma.

Further, XB12/SB04, which showed the highest coagulation time-shortening activity, was measured for its concentration dependency (FIG. 9).

EXAMPLE 8

Antibody Purification

The culture supernatant (10 mL) obtained by the method described in Example 4 was concentrated to 1 mL with Centricon® YM-50 (Millipore). To this concentrate, 10% BSA (10 µL), 1% Tween® 20 (10 µL), and rProtein A Sepharose™ Fast Flow (Amersham Biosciences) (100 µL) were added, and the solution was mixed by overturning at 4° C. overnight. The solution was transferred to an Ultrafree®-MC 0.22 µm filter cup (Millipore), and after washing with TBS containing 0.01% Tween® 20 (500 µL) thrice, the rProtein A Sepharosem resin was suspended in 100 µL of 10 mM HCl/ 0.01% Tween® 20 (pH 2.0) and left to stand for 3 minutes. Then, the antibody was eluted, and the eluate was immediately neutralized with the addition of 5 µL 1 M Tris-HCl, pH 8.0. Using the Microplate Manager III (Bio-Rad Laboratories) software, the human IgG concentration was calculated from the standard curve. The antibody concentration was quantified according to Example 5.

EXAMPLE 9

GST-AP Western Blotting of Anti-F.X Antibody

A recombinant *E. coli* expressing fusion protein of F.X activated peptide (AP) with glutathione S transferase (GST) was constructed. The cDNA covering the full-length translation region of human F.X was PCR amplified from the human liver Marathon-Ready cDNA (Clontech). This cDNA was then used as a template to amplify the region encoding AP region by PCR (Leytus et al., Biochemistry 1986; 25: 5098), which was subcloned into a pGEM-T vector (Promega) to obtain GST-AP-encoding pGEX-F10AP. *E. coli* transformed with this plasmid was cultured, and at OD=0.8, 1 mM IPTG was added to induce GST-AP expression. After centrifuging the culture solution (3,000×g, 30 min, 4° C.), the cells were collected and stored at −20° C. till use.

Figure 10:
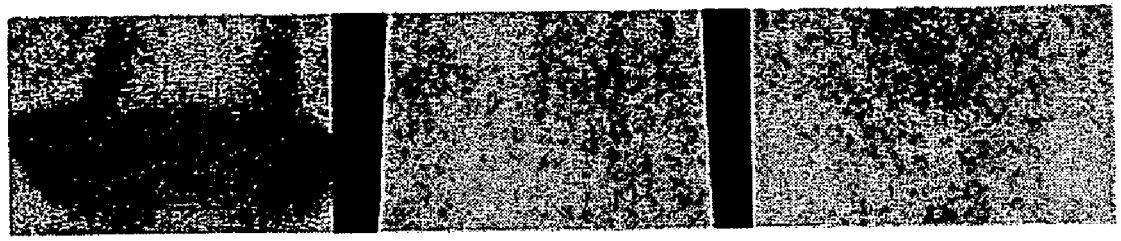
FIG. 10 depicts results of the GST-AP Western blotting of SB04 or SB06, where 1), 2) and 3) are results of reacting transcribed GST-AP with SB04, SB06, and a sample containing no antibody, respectively. The results show detection of only the binding reaction of SB04 with GST-AP.

After resuspending the cell pellet in 1/20 culture volume of PBS, 2.4 mL of SDS-PAGE sample buffer (IWAKI) was added for every 0.1 mL of the suspension, and the resulting mixture was boiled at 95° C. for 5 minutes. This reaction solution (10 µL) was added to each well of a 14% SDS-PAGE mini gel (Asahi Technoglass), and subjected to electrophoresis. The gel after electrophoresis was transferred onto an Immobilon-P™ Transfer Membrane (MILLIPORE) using a semi-dry blotter (BIO-RAD), and blocked with BT-PBS (PBS containing 2% BSA and 0.05% Tween® 20). After the blocking was completed, it was reacted for 1 hour with anti-F.X mouse antibody SB04 or SB06 purified in Example 1-4 and diluted with BT-PBS to 2 µg/mL. After washing with PBS containing 0.05% Tween® 20, the membrane was reacted for 1 hour with an alkaline phosphatase-labeled goat anti-mouse IgG (H+L) (Zymed Laboratories) diluted 2000-fold with BT-PBS. After washing with PBS containing 0.05% Tween® 20, the membrane was color-developed with a colorimetric substrate, BCIP/NBT Phosphatase Substrate (Kirkegaad & Perry Laboratories) (see FIG. 10).

EXAMPLE 10

Obtaining Bispecific Antibody from Immunized Mouse Spleen-derived scFv Library 10-1. Antigen and Immunization Three BALB/c mice (male, 6 weeks old when immunization was initiated (Japan Charles River)), 3 MRL/lpr mice (male, 6 weeks old when immunization was initiated (Japan Charles River)), and 3 C57BL/6N mice (male, 6 weeks old when immunization was initiated (Japan Charles River)) were immunized with antigen factor IXaβ (Enzyme Research Laboratories, Inc.) or factor X (Enzyme Research Laboratories, Inc.) as described below. As an initial immunization, the antigen (40 µg/head) emulsified with FCA (Freund's complete adjuvant H37 Ra; Difco laboratories)) was subcutaneously administered. Two weeks later, the antigen (40 µg/head) emulsified with FIA (Freund's incomplete adjuvant; Difco laboratories) was subcutaneously administered. Afterward, three booster immunizations were given at one week intervals, and 8 days after the final immunization, spleens were excised from the mice.

10-2. Construction of Phage Library

A portion of the spleens excised from the immunized mice prepared in Example 1-1 and 2-1, and the spleens excised from the immunized mice prepared in Example 10-1 were placed in Trizol Reagent (Invitrogen) (50 mg spleen/ml of the reagent), and homogenized using a glass homogenizer. Subsequently, total RNA was extracted according to the method described in the attached instruction manual. From the extract solution, polyA(+)RNA was extracted using a PolyATract System 1000 kit (Promega) according to the method described in the attached instruction manual. cDNA was synthesized by RT-PCR (SuperScript III First-Strand Synthesis System for RT-PCR, Invitrogen) and stored at −20° C. till use.

Figure 11:
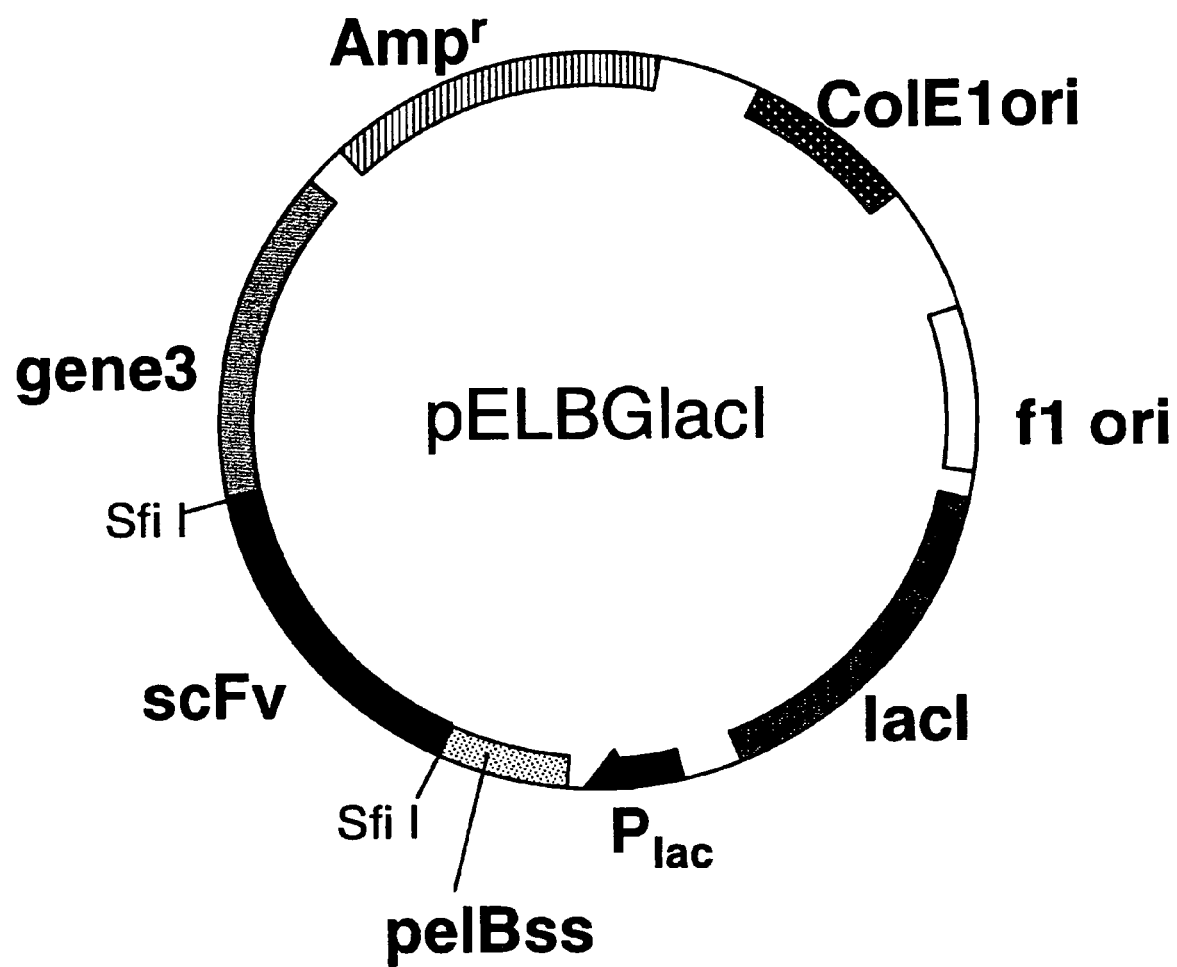
FIG. 11 depicts a pELBGlacI vector. ColE1ori: the replication origin region of ColE1 plasmid series; f1ori: replication origin region of f1 phage; lacI: coding region of lactose repressor protein; $P_{lac}$: lactose promoter; pelBss: signal sequence of *E. coli* PelB protein; scFv: single-strand antibody molecule coding region; gene III (gene3): f1 phage Gene III protein coding region; Amp$^r$: ampicillin-resistant gene; and Sfi I: restriction enzyme Sfi I cleavage site.

As primers for amplification of mouse antibody heavy chain variable region (VH) and light chain variable region (VL) cDNAs, HB primer mixture, HF primer mixture, LB primer mixture, and LF primer mixture used in Examples 3-2 and 3-3 were prepared. For VH amplification, a 50 µL reaction solution (2.5 µL cDNA solution, KOD plus buffer (TOYOBO), 0.2 mM dNTPs, 1.5 mM MgCl$_2$, 3.75 units DNA polymerase KOD plus (TOYOBO)) was prepared using 1 µL of 100 µM HB primer mixture and 100 µM HF primer mixture each. Further, for VL amplification, a 50 µL reaction solution of the same composition as described above was prepared using 1 µL of 100 µM LB primer mixture and 100 µM LF primer mixture each. PCR was performed using a thermal cycler GeneAmp PCR system 9700 (Parkin Elmer) by a 3-minutes heating at 98° C. followed by 32 cycles of reaction (98° C., 20 sec, 58° C., 20 sec, and 72° C., 30 sec in one cycle). After PCR, the reaction solution was subjected to 2% agarose gel electrophoresis. Amplified fragments of the size of interest (about 400 bp) were purified using the QIAquick Gel Extraction Kit (QIAGEN) by the method described in the attached instruction manual, and eluted with sterile water (50 µL). Next, for scFv fragment amplification, ten tubes of a 100 µL reaction solution (3 µL VH fragment solution, 3 µL VL fragment solution, KOD plus buffer (TOYOBO), 0.2 mM dNTPs, 1 mM MgCl$_2$, 5 units DNA polymerase KOD plus (TOYOBO)) were prepared. After the 1$^{st}$ PCR (3-min heating at 94° C. followed by 7 cycles of reaction (94° C., 1 min and 63° C., 4 min in one cycle)), 10 µM scfor primer and 10 µM scback primer (2.5 µL each) were added to each tube kept warm at 63° C., and then the 2$^{nd}$ PCR (a 35-sec heating at 94° C. followed by 30 cycles of reaction (94° C., 2 min and 63° C., 2 min in one cycle)) was performed. After PCR, the reaction solution was purified using the QIAquick PCR purification kit (QIAGEN), and the purified products were digested with restriction enzyme Sfi I (Takara Bio) at 50° C. overnight. After subjecting the digests to 2% agarose gel electrophoresis, amplified fragments of the size of interest (about 800 bp) were purified using the QIAquick Gel Extraction Kit (QIAGEN) by the method described in the attached instruction manual, and eluted with an appropriate amount of sterile water. For presenting scFv on phage gene III protein, pELB-GlacI (see FIG. 11) was used as a phagemid vector. After digesting the vector (10 µg) with restriction enzyme Sfi I (Takara Bio) at 50° C. overnight, cleavage fragments of the size of interest (about 5 kb) were purified using the QIAquick Gel Extraction Kit (QIAGEN) by the method described in the attached instruction manual, and eluted with an appropriate amount of sterile water. The purified PCR product and the purified vector fragment were subjected to a ligation reaction at 16° C. overnight, using Ligation High (TOYOBO) according to the method described in the attached instruction manual. Electrocompetent *E. coli* XL1 Blue cells (Stratagene) or electromax DH12s (Invitrogen) were transformed using the reaction solution, by an electroporation method according to the method described in the attached instruction manual. All of the ampicillin-resistant transformants thus obtained were collected and stored as the recombinant library at −20° C. until use.

The *E. coli* library ($2\times10^9$ cfu) was inoculated into 50 mL of 2×YTAG (2× TY containing 100 μg/mL ampicillin and 2% glucose), and cultured at 37° C. till OD 600 reached 0.4 to 0.5. $4\times10^{11}$ of helper phage VCS M13 (Stratagene) was added to the culture, which was left to stand at 37° C. for 15 minutes for cell infection. The infected cells were cultured at 30° C. for 10 hours, following addition of 450 mL of 2×YTAK (2× TY containing 100 μg/mL ampicillin and 25 μg/mL kanamycin) and 25 μL of 1 mol/L IPTG. The culture supernatant was collected by centrifugation, mixed with 100 mL of PEG-NaCl solution (10% polyethylene glycol 8000, 2.5 mol/L NaCl), and left to stand at 4° C. for 60 minutes. Phage was precipitated by centrifugation at 10,800× g for 30 minutes, and the precipitate was suspended in 40 mL of water, mixed with 8 mL of PEG-NaCl solution, and left to stand at 4° C. for 1 hour. Phage was precipitated by centrifugation at 10,800× g for 30 minutes, and suspended in 5 mL of PBS to obtain the phage library. The phage was stored at 4° C. till use.

10-3. Concentration of Bound Phage by Panning

Factor IXaβ or factor X was labeled with biotin using No-Weigh Premeasured NHS-$PEO_4$-Biotin Microtubes (Pierce). The biotin-labeled factor IXaβ or factor X (100 pmol) was added to the phage library solution prepared in 10-2 (600 μL), and contacted with the antigen for 60 minutes. Dynabeads M-280 Streptavidin (600 μL; DYNAL) washed with 5% M-PBS (PBS containing 5% w/v skim milk) was added for binding for 15 minutes. The bead-bound phage was washed several times with PBST (PBS containing 0.1% Tween-20; 1 mL) and then with PBS. The beads were suspended in 0.8 mL of 0.1 mol/L glycine/HCl (pH 2.2) for 5 minutes to elute the phage.

Alternatively, the phage library (80 μL/well×5) which had been incubated with 2.5% w/v skim milk for 15 minutes was added to factor IXaβ or factor X (10 μg/well×5) immobilized onto an immunoplate (MaxiSorp, Nunc), and was contacted with the antigen for 60 minutes. The antigen-bound phage was washed several times with PBST (PBS containing 0.1% Tween-20; 1 mL) and then with PBS. The bound phage was incubated with 0.8 mL of 0.1 mL glycine/HCl (pH 2.2) for 5 minutes to elute the phage.

The phage solution thus collected was neutralized by adding 2 mol/L Tris (45 μL), added to 10 mL of XL1-Blue cells in logarithmic growth phase (OD 600=0.4 to 0.5), and left to stand for 30 minutes at 37° C. for cell infection. The mixture was spread on a 2×YTAG plate and cultured at 30° C. Colonies were collected, inoculated into 2×YTAG, and cultured at 37° C. until OD 600=0.4 to 0.5. IPTG (1 mol/L; 5 μL) and helper phage VCS M13 ($10^{11}$ pfu) were added to the culture solution (10 mL), and the mixture was left to stand at 37° C. for 30 minutes. The cells were collected by centrifugation, resuspended in 2×YTAK (100 mL), and cultured at 30° C. for 10 hours. The culture supernatant was recovered by centrifugation, mixed with 10% PEG-5 mol/L NaCl solution (20 mL), and left to stand at 4° C. for 20 minutes. Phage was precipitated by centrifugation at 10,800×g for 30 minutes and suspended in PBS (2 mL), and provided for the subsequent panning.

10-4. Phage ELISA

The above-described single colony was inoculated into 2× YTAG (100 μL) and cultured at 30° C. overnight. After 5 μL of this culture was inoculated into 2× YTAG (500 μL) and cultured at 37° C. for 5 hours, helper phage ($2\times10^8$ pfu) was added, and the culture was then left to stand at 37° C. for 30 minutes. Further, after 30 minutes-cultivation with shaking at 37° C., 2× YTAK containing 0.5 mM IPTG (120 μL) was added. After an overnight culture at 30° C., the centrifuged supernatant was subjected to ELISA. For ELISA of clones obtained by panning biotin-labeled antigens, a StreptaWell 96 microtiter plate (Roche) coated with 1.0 μg/mL of biotin-labeled antigen was used. Further, for ELISA of clones obtained by panning native antigens, an immunoplate (MaxiSorp, Nunc) immobilized with 1.0 μg/mL of native antigen was used. After washing with PBST to remove the antigen, the reaction was blocked with 200 μL of 2% M-PBS or 2% BSA-PBS (PBS containing 2% w/v BSA) as a blocking buffer for 1 hour at room temperature. After removing the buffer, the culture supernatant was added to the plate, and left to stand for 60 minutes for phage binding. After washing, the bound phage was detected with an HRP-bound anti-M13 antibody (Amersham Pharmacia Biotech) and TMB substrate (Zymed). The reaction was stopped by adding 1 mol/L $H_2SO_4$, and A450 value was measured with a plate reader.

10-5. Sequence Determination and Clone Selection

Using the 2×YTAG culture medium of the ELISA-positive recombinant *E. coli* clone, nucleotide sequence of the scFv region was determined by PCR amplification with the primers PBG3-F1 (5'-CAGCTATGAAATACCTATTGCC-3'/SEQ ID NO: 1) and PBG3-R1 (5'-CTTTTCATAATCAAAATCAC-CGG-3'/SEQ ID NO: 2). A 15 μL PCR solution comprising 1 μL culture medium, 1.5 μL 10× KOD Dash buffer, 0.2 μL each of 10 pmol/L primers, and 0.3 μl KOD Dash polymerase (TOYOBO, 2.5 U/μL) was subjected to 30 cycles of amplification (96° C., 10 sec, 55° C., 10 sec, and 72° C., 30 sec) using the GeneAmp PCR system 9700 thermal cycler (Perkin Elmer). After PCR, 3 μL ExoSAP-IT (Amersham) was added to 5 μL of the reaction solution, and the mixture was kept warm at 37° C. for 15 minutes and subsequently at 80° C. for 15 minutes. The reaction of this sample was performed using the BigDye Terminator Cycle Sequencing kit (Applied Biosystems) with PBG3-F2 (5'-ATTGCCTACGGCAGCCGCT-3'/SEQ ID NO: 3) or PBG3-R2 (5'-AAATCACCGGAAC-CAGAGCC-3'/SEQ ID NO: 4) as primer, and the products were electrophoresed with an Applied Biosystems PRISM 3700 DNA Sequencer. As a result, clones which have different CDR3 amino acid sequences predicted from the nucleotide sequences were selected for 52 clones as anti-factor IXa and 33 clones as anti-factor X.

10-6. Construction of Bispecific IgG Antibody Expression Vector

To express scfv antibody as an IgG type, antibody variable regions (VH, VL) were cloned into inducible type expression vectors, by means similar to those shown in Examples 3-3, 3-4, and 3-5. Anti-F.IXa antibody variable regions (VH and VL) were individually incorporated into a tetracycline inducible type vector (pcDNA4-g4H and pcDNA4-g4L, respectively). Anti-F.X antibody variable regions (VH and VL) were individually incorporated into an ecdysone analogue inducible type vector (pIND-g4H and pcDNA4-g4L, respectively). From the clones of interest, the respective plasmid DNAs were isolated using the QIAprep Spin Mimiprep Kit (QIAGEN) and dissolved in sterile water (100 μL).

10-7. Expression of Chimera Bispecific Antibody in Animal Cells

Using the DNA solution prepared by means similar to that shown in Example 4-1, DNA was expressed in animal cells by means similar to those shown in Examples 4-2 and 4-3, and the culture supernatant was collected. The sample was stored at 4° C. till use.

EXAMPLE 11

Antibody Purification

To 10 mL of the culture supernnatant obtained by the method described in Example 10-7, 100 µL of rProtein A Sepharose™ Fast Flow (Amersham Biosciences) was added and mixed by overturning at 4° C. overnight. The solution was transferred to an Ultrafree®-MC 0.22 µm filter cup (Millipore), and after three washes with 500 µL of TBS containing 0.01% Tween® 20, rprotein A Sepharose T resin was suspended in 100 µL of 10 mM HCl/0.01% Tween® 20 (pH 2.0), and left to stand for 3 minutes. The antibody was then eluted and the eluate was immediately neutralized by adding 5 µL of 1 M Tris-HCl, pH 8.0. Using the Microplate Manager III (Bio-Rad Laboratories) software, the human IgG concentration in the culture supernnatant was calculated from the standard curve of human IgG4 (humanized anti-TF antibody, see WO 99/51743). The antibody concentration was quantitated according to Example 5.

EXAMPLE 12

F.VIIIa (Activated Coagulation Factor VIII)-mimetic Activity Assay

The F.VIIIa-rniimetic activity of a bispecific antibody was assessed by the following enzymatic assay. The following reactions were all performed at room temperature. A mixed solution of 10 µL factor IX (15 µg/mL; Enzyme Research Laboratories), 5 µL TBSB containing 100 mM $CaCl_2$ and 20 mM $MgCl_2$ and 50 µL of the culture supernatant obtained by the method described in Example 10-7 was incubated in a 96-well plate for 1 hour. Then, 10 µL factor XIa (10 ng/mL; Enzyme Research Laboratories), 20 µL factor X (50 µg/mL; Enzyme Research Laboratories), and 5 µL phospholipids (400 µg/mL) were added to initiate the enzymatic reaction. After 30 minutes, the reaction was stopped by adding 10 µL of 0.5 M EDTA.

After adding 50 µL of a calorimetric substrate solution to each well, the absorbance at 405 nm (reference wavelength 655 nm) was measured at 0 and 60 minutes with a Model 3550 Microplate Reader (Bio Rad Laboratories). F.VIIIa-mimetic activity was expressed as a value obtained by subtracting the value of absorbance change in the culture supernatant expressing no antibody from that of the culture supernatant expressing the antibody.(see FIG. 12).

TBSB was used as a solvent for phospholipid, factor XIa, factor IX, and factor X. The calorimetric substrate solution was a 1:1 mixture of "Tesutochimu" colorimetric substrate S-2222 (Chromogenix) dissolved according to the attached instruction manual and polybrene solution (0.6 mg/L hexadimethnine bromide; Sigma).

EXAMPLE 13

Plasma Coagulation Assay

Figure 14:
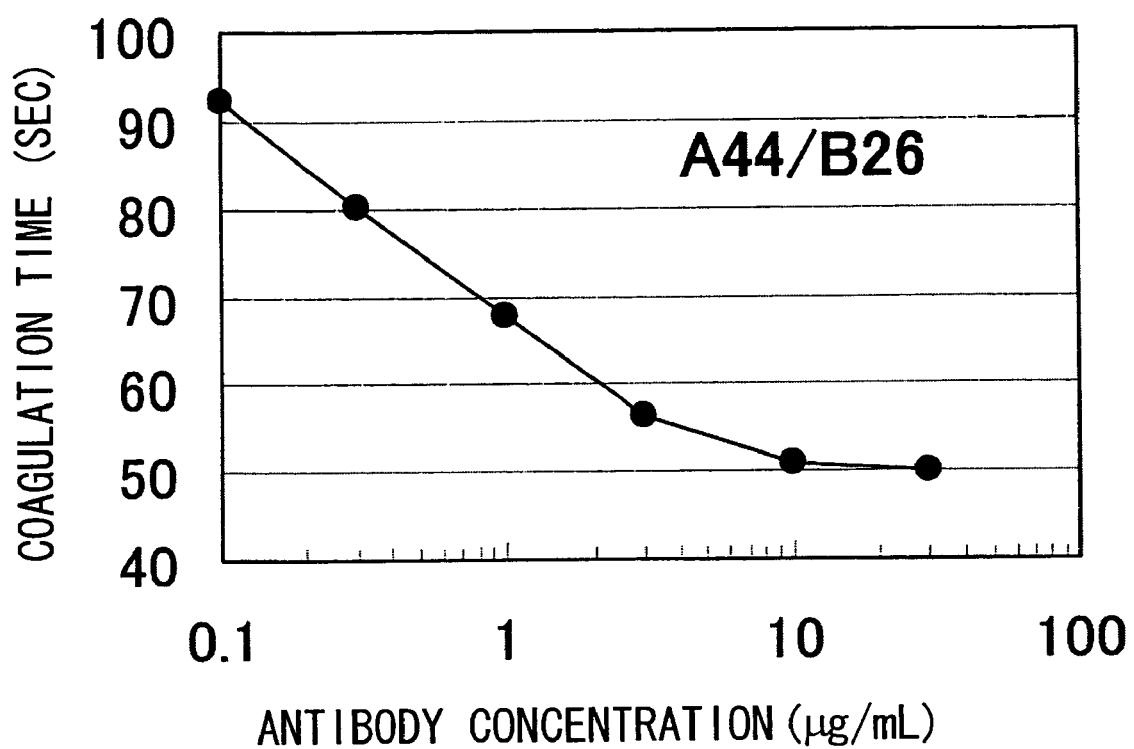
FIG. 14 depicts results of measuring the coagulation time at various concentrations of A44/B26, which had a high coagulation time (APTT) shortening effect in FIG. 13. The coagulation time was 113 seconds when the antibody was not added. As a result, A44/B26 showed a concentration-dependent effect of shortening the coagulation time. The antibody concentration in the figure shows values of the antibody solution mixed with F.VIII-deficient plasma.
Figure 15:
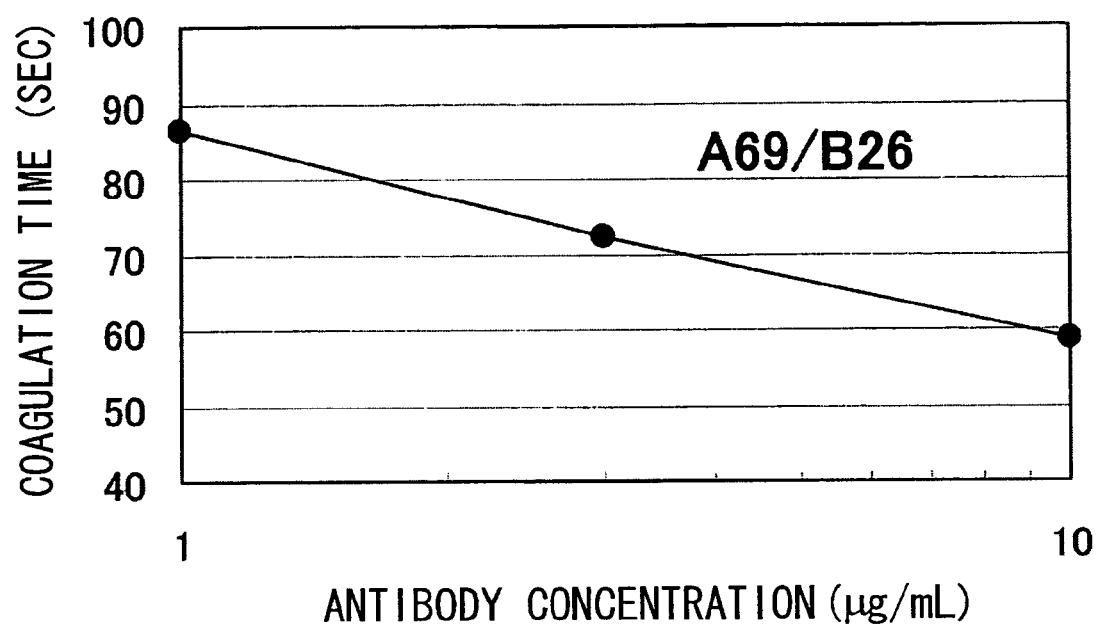
FIG. 15 depicts results of measuring the coagulation time at various concentrations of A69/B26, which had a high coagulation time (APTT) shortening effect in FIG. 13. The coagulation time was 109.6 seconds when the antibody was not added. As a result, A69/B26 showed a concentration-dependent effect of shortening the coagulation time. The antibody concentration in the figure shows values of the antibody solution mixed with F.VIII-deficient plasma.

To elucidate whether a bispecific antibody prepared according to the method of Example 11 recovers the coagulation capability of hemophilia A blood, effects of the antibody on activated partial thromboplastin time (APTT) using F.VIII-deficient plasma were assessed by a method similar to that shown in Example 7 (see FIG. 13). Further, A44/B26 and A69/B26, which are highly effective in shortening coagulation time, were measured for their concentration dependency (see FIGS. 14 and 15).

EXAMPLE 14

Evaluation of the Concomitant Use of a Bispecific Antibody and F.VIII

Figure 16:
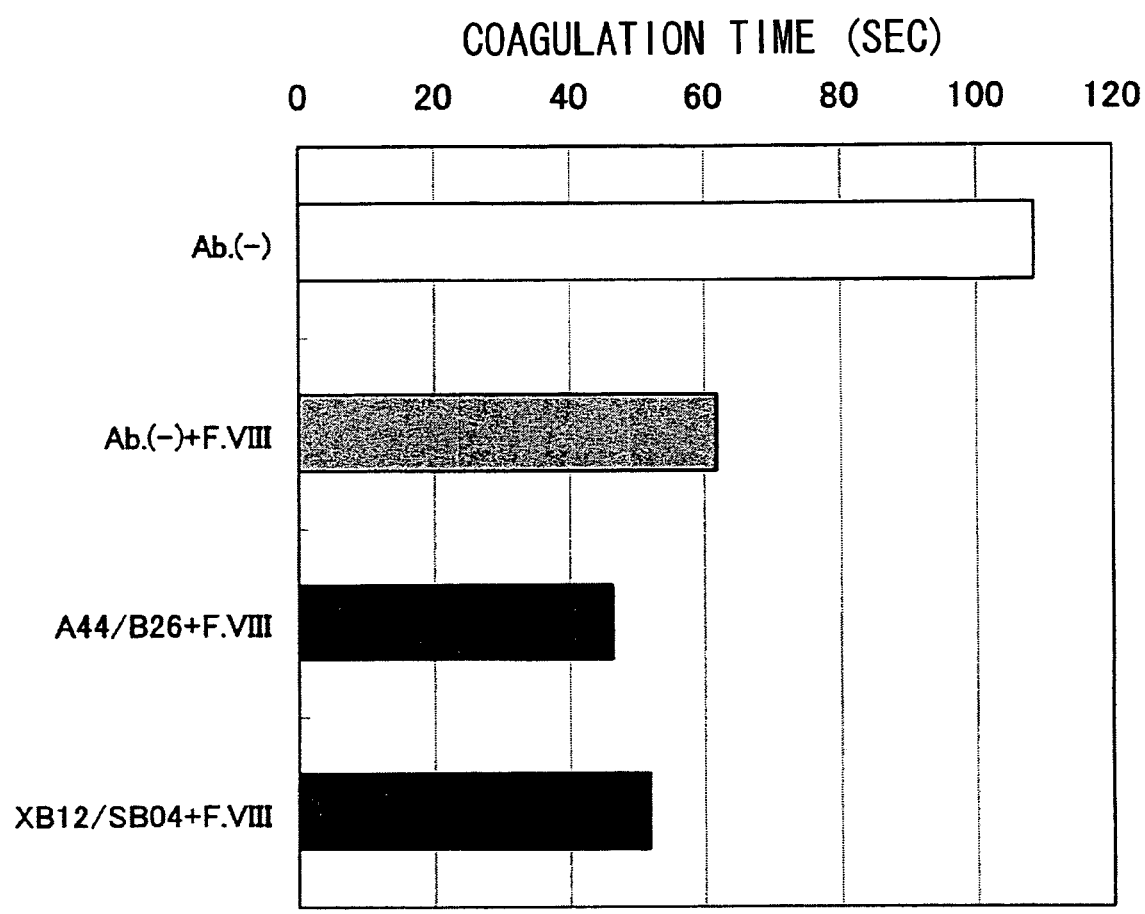
FIG. 16 depicts results of measuring the coagulation time (APTT) in the coexistence of A44/B26 or XB12/SB04 with F.VIII. As a result, when compared to F.VIII alone, a mixed solution of A44/B26 or XB 12/SB04 with F.VIII showed a coagulation time shortening effect.

Concomitant use of a bispecific antibody and F.VIII was evaluated under the following plasma coagulation assay conditions. A mixture of 40 µL antibody solution (25 µg/mL) and 50 µL F.VIII-deficient plasma (Biomerieux) was incubated at room temperature for 30 minutes. To this mixture, 10 µL of the recombinant blood coagulation factor VIII formulation Kogenate® FS (BAYER) and 50 µL APTT reagents (Dade Behring) were added, and warmed at 37° C. for 3 minutes. Coagulation reaction was initiated by adding 50 µL of 20 mM of $CaCl_2$ (Dade Behring). The time required for coagulation was measured using CR-A (Amelung)-connected KC10A (Amelung) (see FIG. 16).

EXAMPLE 15

Effects of Bispecific IgG Antibody in Inhibitor Plasma

Figure 17:
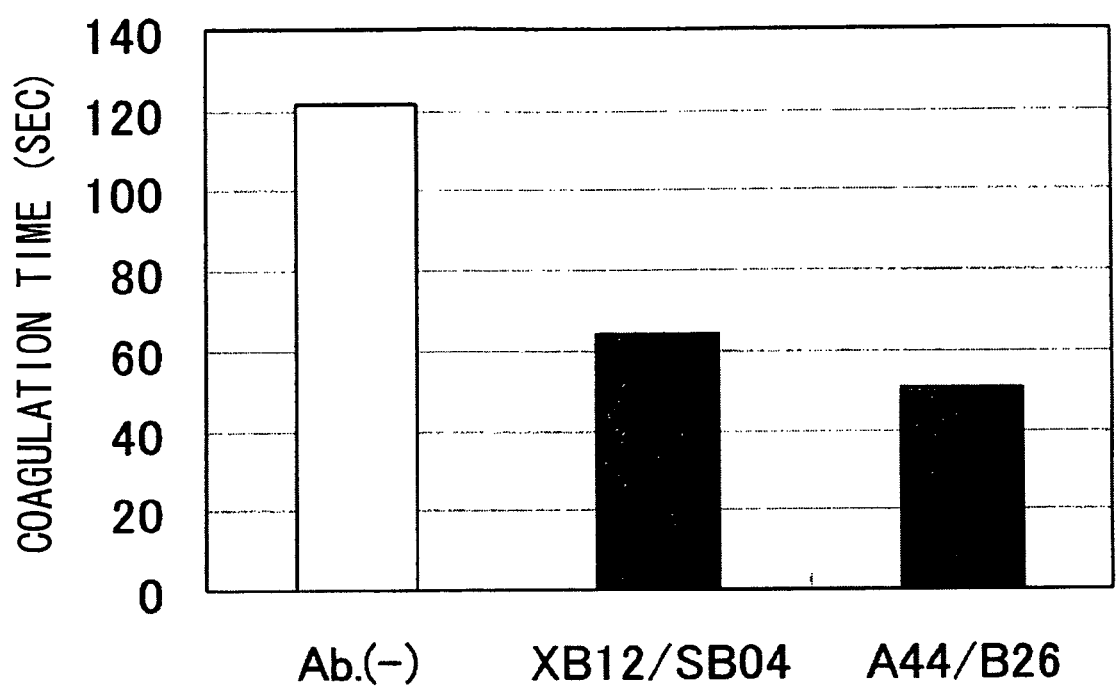
FIG. 17 depicts results of measuring the coagulation time (APTT) in inhibitor plasma under the presence of A44/B26 or XB12/SB04. As a result, A44/B26 or XB12/SB04 showed a coagulation time shortening effect compared with in the absence of the antibodies.

Effects of a bispecific IgG antibody in the inhibitor plasma were assessed under the following plasma coagulation assay conditions. A mixture of 50 µL F.VIII-deficient plasma (Biomerieux) and 10 µL anti-human F.VIII neutralizing antibody (100 µg/mL; Catalog Number: MAB3440, CHEMICON) was incubated at room temperature for 30 minutes. This plasma was used as inhibitor plasma. To this inhibitor plasma, 40 µL of the antibody solution (25 µg/mL) and 50 µL APTT reagent (Dade Behring) were added, and warmed at 37° C. for 3 minutes. Coagulation reaction was initiated by adding 50 µL of 20 mM $CaCl_2$ (Dade Behring) to the mixture. The time required for coagulation was measured using CR-A (Amelung)-connected KC10A (Amelung) (see FIG. 17).

EXAMPLE 16

Humanization of Bispecific Antibody

Among the bispecific antibodies obtained in Examples 1 to 7, XB12 (mouse anti-factor IXa antibody)/SB04 (mouse anti-factor X antibody), which was the most effective in shortening blood coagulation time, was subjected to humanization as follows.

16-1. Homology Search of Human Antibodies

The database was constructed based on amino acid sequence data of human antibodies obtained from Kabat Database (ftp://ftp.ebi.ac.uk/pub/databases/kabat/) and IMGT Database (http://imgt.cines.fr/) available publicly, and homology search was carried out separately for the mouse XB12-H chain variable region, mouse XB132-L chain variable region, mouse SB04-H chain variable region, and mouse SB04-L chain variable region. The results confirmed that they have high homologies to the human antibody sequences shown below, and it was thus decided that they would be used as the framework region (hereinafter abbreviated as FR) of humanized antibodies.

(1) XB12-H chain variable region: KABATID-020619 (Kabat Database) (Mariette et al., Arthritis Rheum. 1993; 36: 1315-1324)
(2) XB12-L chain variable region: EMBL Accession No. X61642 (IMGT Database) (Mark et al., J Mol Biol. 1991; 222: 581-597.)
(3) SB04-H chain variable region: KABATID-025255 (Kabat Database) (Demaison et al., Immunogetetics 1995; 42: 342-352)
(4) SB04-L chain variable region: EMBL Accession No. AB0641 11 (IMGT Database) (Unpublished data)

For preparation of humanized antibodies, complementarity determining regions (hereinafter abbreviated as CDR) of each mouse antibody were grafted into the FRs of human antibodies (1)-(4).

Also, the web site on the NCBI available publicly (http://www.ncbi.nhn.nih.gov/BLAST/) was used to search secretory signal sequences of human antibody that are highly homologous to human antibodies (1)-(4). The following secretory signal sequences obtained by the homology search were used.
(1) XB12-H chain variable region: GenBank Accession No. AF062120
(2) XB12-L chain variable region: GenBank Accession No. M74019
(3) SB04-H chain variable region: GenBank Accession No. BC019337
(4) SB04-L chain variable region: GenBank Accession No. AY204756

16-2. Construction of Humanized Antibody Gene Expression Vector

Twelve synthetic oligonucleotides of about 50 bases were prepared from a nucleotide sequence encoding the amino acid sequence from the secretory signal sequence to the antibody variable region, such that about 20 bases of their 3'-terminal hybridize with each other. Further, a primer hybridizing to the 5'-terminal of an antibody variable region gene and having the XhoI cleavage sequence, and a primer hybridizing to the 3'-terminal of an antibody variable region gene and having the SfiI cleavage sequence were prepared.

The synthetic oligonucleotides prepared (2.5 µM, 1 µL each) were mixed, and 1× TaKaRa Ex Taq Buffer, 0.4 mM dNTPs, and 0.5 units TaKaRa Ex Taq (all from Takara Shuzo) were added to make up a 48 µL reaction solution. After warming the mixture at 94° C. for 5 minutes, 2 cycles of reaction (94° C., 2 min, 55° C., 2 min, and 72° C., 2 min) were performed to assemble and elongate each of the synthetic oligo DNAs. Next, a primer hybridizing to the 5'-terminal and a primer hybridizing to the 3'-terminal of the antibody gene were added (10 µM, 1 µL each), and the antibody variable region genes were amplified by 35 cycles of reaction (94° C., 30 sec, 55° C., 30sec, and 72° C., 1 min) and a 5 minutes reaction at 75° C. After PCR, the reaction solution as a whole was subjected to 1% agarose gel electrophoresis. Amplified fragments of the expected size (about 400 bp) were purified with the QIAquick Gel Extraction Kit (QIAGEN) by the method described in the attached instruction manual, and eluted with sterile water (30 µL). Fragments were cloned using the pGEM-T Easy Vector System (Promega) by the method described in the attached instruction manual. Nucleotide sequences of the DNA fragments were determined using the BigDye.Terminator Cycle Sequencing Kit (Applied Biosystems) on ABI PRISM 3700 DNA Sequencer (Applied Biosystems) according to the method described in the attached instruction manual.

After digesting a plasmid confirmed to comprise the correct humanized antibody variable region gene sequence with XhoI and SfiI, the reaction solution was subjected to 1% agarose gel electrophoresis. DNA fragments of the expected size (about 400 bp) were purified using the QIAquick Gel Extraction Kit (QIAGEN) by the method described in the attached instruction manual, and eluted with sterile water (30 µL). Further, after digesting the tetracycline-inducible type expression plasmids (pcDNA4-g4H, pcDNA4-g4L) and the ecdysone analogue inducible type expression plasmids (pIND-g4H, pIND-g4L) prepared in Example 3-4 with XhoI and SfiI, fragments comprising the antibody constant region (about 5 kb) were purified using the QIAquick Gel Extraction Kit (QIAGEN) by the method described in the attached instruction manual, and eluted with sterile water (30 µL). The humanized XB12 antibody gene fragment (H chain variable region (hereinafter VH) or L chain variable region (hereinafter VL)) digested with XhoI and SfiI, and the tetracycline-inducible type expression plasmid (pcDNA4-g4H, pcDNA4-g4L) digested with XhoI and SfiI were subjected to a ligation reaction using the Rapid DNA Ligation Kit (Roche Diagnostics) by the method described in the attached instruction manual. In addition, the humanized SB04 antibody gene fragment digested with XhoI and SfiI (H chain variable region or L chain variable region), and the ecdysone analogue inducible type expression plasmid digested with XhoI and SfiI (pIND-g4H, pIND-g4L) were subjected to a ligation reaction using the Rapid DNA Ligation Kit (Roche Diagnostics) by the method described in the attached instruction manual. A portion of each of the reaction mixture was used to transform DH5α strain E. coli (TOYOBO).

16-3. Preparation of Humanized Bispecific Antibody

The genes were transfected and expressed in HEK293H by the methods described in Examples 4-2 and 4-3, using four types of humanized antibody expression vectors as well as pcDNA6/TR and pVgRXR. Further, antibody purification and quantification of antibody concentration were conducted by the methods shown in Examples 8 and 5.

Figure 18:
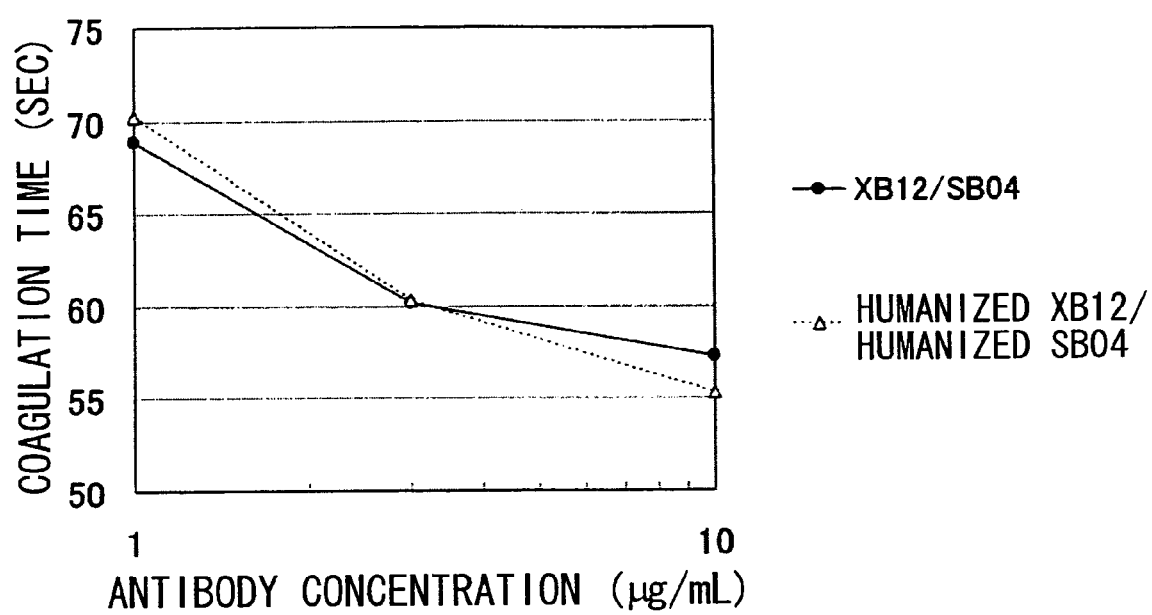
FIG. 18 depicts results of measuring the coagulation time at various concentrations of XB12/SB04 and humanized XB12/humanized SB04. The coagulation time was 111.3 seconds when no antibody was added. As a result of the measurement, humanized XB12/humanized SB04 showed a coagulation time shortening effect similar to that of XB12/SB04. The antibody concentration in the figure shows values of the antibody solutions mixed with F.VIII-deficient plasma.

16-4. Activity Assessment of Humanized Bispecific Antibody and Modification of Antibody Sequence To assess the plasma coagulation ability of the thus-prepared humanized bispecific antibodies and chimera bispecific antibody XB12/SB04, effects of the antibodies on APTT were examined using F.VIII-deficient plasma. Amino acids of the human antibody FR were modified to increase activities of humanized bispecific antibodies whose blood coagulation capability has been reduced. In addition, the cysteine residues in the CDR3 of XB12 antibody VH were modified to alanine in concern of the possible drop in its thermostability. Specifically, mutations were introduced into the humanized antibody expression vector using the QuikChange Site-Directed Mutagenesis Kit (Stratagene) by the method described in the attached instruction manual. By repeating amino acid modification of the FR sequence and assessment of blood coagulation ability, a humanized bispecific antibody (humanized XB12 antibody (VH:hXB12f-A, VL:hXBVL)/humanized SB04 antibody (VH:hSB04e, VL:hSBVL-F3f)) was obtained (FIG. 18).

INDUSTRIAL APPLICABILITY

The present invention provides bispecific antibodies that recognize both an enzyme and its substrate, and which functionally substitute for a cofactor which enhances the enzymatic activity.

The bispecific antibodies according to the present invention are thought to have high stability in blood and low antigenicity. Thus, it is greatly expected that they will become pharmaceuticals.

The invention claimed is:

1. A bispecific antibody that recognizes blood coagulation factor IX and/or activated blood coagulation factor IX and blood coagulation factor X, wherein said antibody comprises complementarity determining regions (CDRs) comprising
   (A) the amino acid sequences of anti-blood coagulation factor IX/IXa antibody H chain CDRs of the following (a1) or (a2) and L chain CDRs of the following (b1) or (b2); and
   (B) the amino acid sequences of anti-blood coagulation factor X antibody H chain CDRs of any one of the following (c1) to (c9) and L chain CDRs of the following (d1) or (d2):
   (a1) H chain CDR 1, 2, and 3 amino acid sequences described in SEQ ID NOs: 14, 15, and 16, respectively;
   (a2) H chain CDR 1, 2, and 3 amino acid sequences described in SEQ ID NOs: 18, 19, and 20, respectively;
   (b1) L chain CDR 1, 2, and 3 amino acid sequences described in SEQ ID NOs: 206, 207, and 208, respectively;
   (b2) L chain CDR 1, 2, and 3 amino acid sequences described in SEQ ID NOs: 214, 215, and 216, respectively;
   (c1) H chain CDR 1, 2, and 3 amino acid sequences described in SEQ ID NOs: 22, 23, and 24, respectively;
   (c2) H chain CDR 1, 2, and 3 amino acid sequences described in SEQ ID NOs: 26, 27, and 28, respectively;
   (c3) H chain CDR 1, 2, and 3 amino acid sequences described in SEQ ID NOs: 30, 31, and 32, respectively;
   (c4) H chain CDR 1, 2, and 3 amino acid sequences described in SEQ ID NOs: 34, 35, and 36, respectively;
   (c5) H chain CDR 1, 2, and 3 amino acid sequences described in SEQ ID NOs: 38, 39, and 40, respectively;
   (c6) H chain CDR 1, 2, and 3 amino acid sequences described in SEQ ID NOs: 42, 43, and 44, respectively;
   (c7) H chain CDR 1, 2, and 3 amino acid sequences described in SEQ ID NOs: 46, 47, and 48, respectively;
   (c8) H chain CDR 1, 2, and 3 amino acid sequences described in SEQ ID NOs: 50, 51, and 52, respectively;
   (c9) H chain CDR 1, 2, and 3 amino acid sequences described in SEQ ID NOs: 54, 55, and 56, respectively;
   (d1) L chain CDR 1, 2, and 3 amino acid sequences described in SEQ ID NOs: 210, 211, and 212, respectively;

(d2) L chain CDR 1, 2, and 3 amino acid sequences described in SEQ ID NOs: 218, 219, and 220, respectively,
wherein the antibody functionally substitutes for blood coagulation factor VIII and/or activated blood coagulation factor VIII.

2. A composition comprising the antibody according to claim 1 and a pharmaceutically acceptable carrier.

3. A composition comprising the antibody according to claim 1, wherein said composition is a pharmaceutical composition for treating bleeding, a disorder accompanied by bleeding, or a disorder caused by bleeding.

4. The composition according to claim 3, wherein the bleeding, disorder accompanied by bleeding, or disorder caused by bleeding is a disorder that arises and/or progresses as a result of an activity decrease or deficiency of blood coagulation factor VIII and/or activated blood coagulation factor VIII.

5. The composition according to claim 4, wherein the disorder that arises and/or progresses as a result of an activity decrease or deficiency of blood coagulation factor VIII and/or activated blood coagulation factor VIII is hemophilia A.

6. The composition according to claim 4, wherein the disorder that arises and/or progresses as a result of an activity decrease or deficiency of blood coagulation factor VIII and/or activated blood coagulation factor VIII is a disorder in which an inhibitor against blood coagulation factor VIII and/or activated blood coagulation factor VIII is generated.

7. The composition according to claim 4, wherein the disorder that arises and/or progresses as a result of an activity decrease or deficiency of blood coagulation factor VIII and/or activated blood coagulation factor VIII is acquired hemophilia.

8. The composition according to claim 4, wherein the disorder that arises and/or progresses as a result of an activity decrease of blood coagulation factor VIII and/or activated blood coagulation factor VIII is von Willebrand's disease.

9. A method for treating bleeding, a disorder accompanied by bleeding, or a disorder caused by bleeding, wherein said method comprises the step of administering the antibody according to claim 1.

10. A kit for treating bleeding, a disorder accompanied by bleeding, or a disorder caused by bleeding, wherein said kit comprises at least the antibody according to claim 1.

11. A method of treating bleeding, a disorder accompanied by bleeding, or a disorder caused by bleeding, wherein said method comprises the step of administering the antibody according to claim 1 in combination with blood coagulation factor VIII.

12. A kit for treating bleeding, a disorder accompanied by bleeding, or a disorder caused by bleeding, wherein said kit comprises at least the antibody according to claim 1 and blood coagulation factor VIII.

13. A method for treating bleeding, a disorder accompanied by bleeding, or a disorder caused by bleeding, wherein said method comprises the step of administering the composition according to claim 2.

14. A bispecific antibody that recognizes blood coagulation factor IX and/or activated blood coagulation factor IX and blood coagulation factor X, wherein the antibody
(A) binds the same epitope of blood coagulation factor IX/IXa as an antibody having the H chain CDRs of (a1) or (a2) below and the L chain CDRs of (b1 or (b2) below, and
(B) binds the same epitope of blood coagulation factor X as an antibody having the H chain CDRs of any one of (c1) to (c9) below and the L chain CDRs of (d1) or (d2) below:
(a1) H chain CDR 1, 2, and 3 amino acid sequences described in SEQ ID NOs: 14, 15, and 16, respectively;
(a2) H chain CDR 1, 2, and 3 amino acid sequences described in SEQ ID NOs: 18, 19, and 20, respectively;
(b1) L chain CDR 1, 2, and 3 amino acid sequences described in SEQ ID NOs: 206, 207, and 208, respectively;
(b2) L chain CDR 1, 2, and 3 amino acid sequences described in SEQ ID NOs: 214, 215, and 216, respectively;
(c1) H chain CDR 1, 2, and 3 amino acid sequences described in SEQ ID NOs: 22, 23, and 24, respectively;
(c2) H chain CDR 1, 2, and 3 amino acid sequences described in SEQ ID NOs: 26, 27, and 28, respectively;
(c3) H chain CDR 1, 2, and 3 amino acid sequences described in SEQ ID NOs: 30, 31, and 32, respectively;
(c4) H chain CDR 1, 2, and 3 amino acid sequences described in SEQ ID NOs: 34, 35, and 36, respectively;
(c5) H chain CDR 1, 2, and 3 amino acid sequences described in SEQ ID NOs: 38, 39, and 40, respectively;
(c6) H chain CDR 1, 2, and 3 amino acid sequences described in SEQ ID NOs: 42, 43, and 44, respectively;
(c7) H chain CDR 1, 2, and 3 amino acid sequences described in SEQ ID NOs: 46, 47, and 48, respectively;
(c8) H chain CDR 1, 2, and 3 amino acid sequences described in SEQ ID NOs: 50, 51, and 52, respectively;
(c9) H chain CDR 1, 2, and 3 amino acid sequences described in SEQ ID NOs: 54, 55, and 56, respectively;
(d1) L chain CDR 1, 2, and 3 amino acid sequences described in SEQ ID NOs: 210, 211, and 212, respectively;
(d2) L chain CDR 1, 2, and 3 amino acid sequences described in SEQ ID NOs: 218, 219, and 220, respectively,
wherein the antibody functionally substitutes for blood coagulation factor VIII and/or activated blood coagulation factor VIII.

15. A bispecific antibody that recognizes blood coagulation factor IX and/or activated blood coagulation factor IX and blood coagulation factor X, the antibody comprising:
(a) an anti-blood coagulation factor IX/IXa antibody variable region comprising the amino acid sequence of SEQ ID NO: 13, 17, 85, 205, or 213; and
(b) an anti-blood coagulation factor X antibody variable region comprising the amino acid sequence of SEQ ID NO: 21, 25, 29, 33, 37, 41, 45, 49, 53, 161, 209, or 217,
wherein the antibody functionally substitutes for blood coagulation factor VIII and/or activated blood coagulation factor VIII.

16. A bispecific antibody that recognizes blood coagulation factor IX and/or activated blood coagulation factor IX and blood coagulation factor X, the antibody comprising anti-blood coagulation factor IX/IXa H and L variable domains comprising a set of six CDR sequences selected from (a1) and (a2) below and anti-blood coagulation factor X H and L variable domains comprising a set of six CDR sequences selected from (b1) and (b2) below:
- (a1) H chain CDR 1, 2, and 3 amino acid sequences described in SEQ ID NOs: 14, 15, and 16, respectively, and L chain CDR 1, 2, and 3 amino acid sequences described in SEQ ID NOs: 214, 215, and 216, respectively;
- (a2) H chain CDR 1, 2, and 3 amino acid sequences described in SEQ ID NOs: 86, 87, and 88, respectively, and L chain CDR 1, 2, and 3 amino acid sequences described in SEQ ID NOs: 206, 207, and 208, respectively;
- (b1) H chain CDR 1, 2, and 3 amino acid sequences described in SEQ ID NOs: 22, 23, and 24, respectively, and L chain CDR 1, 2, and 3 amino acid sequences described in SEQ ID NOs: 218, 219, and 220, respectively;
- (b2) H chain CDR 1, 2, and 3 amino acid sequences described in SEQ ID NOs: 162, 163, and 164, respectively, and L chain CDR 1, 2, and 3 amino acid sequences described in SEQ ID NOs: 210, 211, and 212, respectively,
- wherein the antibody functionally substitutes for blood coagulation factor VIII and/or activated blood coagulation factor VIII.

17. A bispecific antibody that recognizes blood coagulation factor IX and/or activated blood coagulation factor IX and blood coagulation factor X, the antibody comprising
- (A) anti-blood coagulation factor IX/IXa antibody H and L variable domains comprising a set of six CDR sequences selected from (i) and (ii):
  - (i) H chain CDR 1, 2, and 3 amino acid sequences described in SEQ ID NOs: 14, 15, and 16, respectively, and L chain CDR 1, 2, and 3 amino acid sequences described in SEQ ID NOs: 214, 215, and 216, respectively;
  - (ii) H chain CDR 1, 2, and 3 amino acid sequences described in SEQ ID NOs: 86, 87, and 88, respectively, and L chain CDR 1, 2, and 3 amino acid sequences described in SEQ ID NOs: 206, 207, and 208, respectively; and
- (B) an anti-blood coagulation factor X antibody variable domain comprising the amino acid sequence of SEQ ID NO: 21, 25, 29, 33, 37, 41, 45, 49, 53, 161, 209, or 217, wherein the antibody functionally substitutes for blood coagulation factor VIII and/or activated blood coagulation factor VIII.

18. A bispecific antibody that recognizes blood coagulation factor IX and/or activated blood coagulation factor IX and blood coagulation factor X, the antibody comprising
- (A) an anti-blood coagulation factor IX/IXa antibody variable domains comprising the amino acid sequence of SEQ ID NO: 13, 17, 85, 205, or 213; and
- (B) anti-blood coagulation factor X antibody H and L variable domains comprising a set of six CDR sequences selected from (i) and (ii):
  - (i) H chain CDR 1, 2, and 3 amino acid sequences described in SEQ ID NOs: 22, 23, and 24, respectively, and L chain CDR 1, 2, and 3 amino acid sequences described in SEQ ID NOs: 218, 219, and 220, respectively;
  - (ii) H chain CDR 1, 2, and 3 amino acid sequences described in SEQ ID NOs: 162, 163, and 164, respectively, and L chain CDR 1, 2, and 3 amino acid sequences described in SEQ ID NOs: 210, 211, and 212, respectively,
- wherein the antibody functionally substitutes for blood coagulation factor VIII and/or activated blood coagulation factor VIII.

19. A bispecific antibody that recognizes blood coagulation factor IX and/or activated blood coagulation factor IX and blood coagulation factor X, the antibody comprising an anti-blood coagulation factor IX/IXa antibody variable domain comprising the amino acid sequence of SEQ ID NO: 13, 17, 85, 205, or 213, wherein the antibody functionally substitutes for blood coagulation factor VIII and/or activated blood coagulation factor VIII.

20. A bispecific antibody that recognizes blood coagulation factor IX and/or activated blood coagulation factor IX and blood coagulation factor X, the antibody comprising anti-blood coagulation factor IX/IXa antibody H and L variable domains comprising a set of six CDR sequences selected from (a) and (b):
- (a) H chain CDR 1, 2, and 3 amino acid sequences described in SEQ ID NOs: 14, 15, and 16, respectively, and L chain CDR 1, 2, and 3 amino acid sequences described in SEQ ID NOs: 214, 215, and 216, respectively;
- (b) H chain CDR 1, 2, and 3 amino acid sequences described in SEQ ID NOs: 86, 87, and 88, respectively, and L chain CDR 1, 2, and 3 amino acid sequences described in SEQ ID NOs: 206, 207, and 208, respectively,
- wherein the antibody functionally substitutes for blood coagulation factor VIII and/or activated blood coagulation factor VIII.

21. A bispecific antibody that recognizes blood coagulation factor IX and/or activated blood coagulation factor IX and blood coagulation factor X, the antibody comprising an anti-blood coagulation factor X antibody variable region comprising the amino acid sequence of SEQ ID NO: 21, 25, 29, 33, 37, 41, 45, 49, 53, 161, 209, or 217, wherein the antibody functionally substitutes for blood coagulation factor VIII and/or activated blood coagulation factor VIII.

22. A bispecific antibody that recognizes blood coagulation factor IX and/or activated blood coagulation factor IX and blood coagulation factor X, the antibody comprising anti-blood coagulation factor X antibody H and L variable domains comprising a set of six CDR sequences selected from (a) and (b):
- (a) H chain CDR 1, 2, and 3 amino acid sequences described in SEQ ID NOs: 22, 23, and 24, respectively, and L chain CDR 1, 2, and 3 amino acid sequences described in SEQ ID NOs: 218, 219, and 220, respectively;
- (b) H chain CDR 1, 2, and 3 amino acid sequences described in SEQ ID NOs: 162, 163, and 164, respectively, and L chain CDR 1, 2, and 3 amino acid sequences described in SEQ ID NOs: 210, 211, and 212, respectively,
- wherein the antibody functionally substitutes for blood coagulation factor VIII and/or activated blood coagulation factor VIII.

23. A method of promoting blood coagulation factor X activation by blood coagulation factor IXa, the method comprising contacting a blood coagulation factor X and a blood coagulation factor IXa with the antibody according to claim 1.

24. A method of promoting coagulation of blood or plasma, the method comprising contacting blood or plasma with the antibody according to claim 1.

25. The method of claim 24, wherein the blood or plasma is deficient in blood coagulation factor VIII or has a functional reduction in blood coagulation factor VIII activity.

26. A bispecific antibody that recognizes blood coagulation factor IX and/or activated blood coagulation factor IX and blood coagulation factor X, wherein the antibody
   (a) binds the same epitope of blood coagulation factor IX/IXa as an antibody having a variable region comprising the amino acid sequence of SEQ ID NO: 13, 17, 85, 205, or 213, and
   (b) binds the same epitope of blood coagulation factor X as an antibody having variable region comprising the amino acid sequence of SEQ ID NO: 21, 25, 29, 33, 37, 41, 45, 49, 53, 161, 209, or 217,
   wherein the antibody functionally substitutes for blood coagulation factor VIII and/or activated blood coagulation factor VIII.

27. A bispecific antibody that recognizes blood coagulation factor IX and/or activated blood coagulation factor IX and blood coagulation factor X, wherein the antibody
   (A) binds the same epitope of blood coagulation factor IX/IXa as an antibody having H and L variable domains comprising a set of six CDR sequences selected from (a1) and (a2) below, and
   (B) binds the same epitope of blood coagulation factor X as an antibody having H and L variable domains comprising a set of six CDR sequences selected from (b1) and (b2) below,
      (a1) H chain CDR 1, 2, and 3 amino acid sequences described in SEQ ID NOs: 14, 15, and 16, respectively, and L chain CDR 1, 2, and 3 amino acid sequences described in SEQ ID NOs: 214, 215, and 216, respectively;
      (a2) H chain CDR 1, 2, and 3 amino acid sequences described in SEQ ID NOs: 86, 87, and 88, respectively, and L chain CDR 1, 2, and 3 amino acid sequences described in SEQ ID NOs: 206, 207, and 208, respectively;
      (b1) H chain CDR 1, 2, and 3 amino acid sequences described in SEQ ID NOs: 22, 23, and 24, respectively, and L chain CDR 1, 2, and 3 amino acid sequences described in SEQ ID NOs: 218, 219, and 220, respectively;
      (b2) H chain CDR 1, 2, and 3 amino acid sequences described in SEQ ID NOs: 162, 163, and 164, respectively, and L chain CDR 1, 2, and 3 amino acid sequences described in SEQ ID NOs: 210, 211, and 212, respectively;
   wherein the antibody functionally substitutes for blood coagulation factor VIII and/or activated blood coagulation factor VIII.

28. A bispecific antibody that recognizes blood coagulation factor IX and/or activated blood coagulation factor IX and blood coagulation factor X, wherein the antibody
   (A) binds the same epitope of blood coagulation factor IX/IXa as an antibody having H and L variable domains comprising a set of six CDR sequences selected from (i) and (ii):
      (i) H chain CDR 1, 2, and 3 amino acid sequences described in SEQ ID NOs: 14, 15, and 16, respectively, and L chain CDR 1, 2, and 3 amino acid sequences described in SEQ ID NOs: 214, 215, and 216, respectively;
      (ii) H chain CDR 1, 2, and 3 amino acid sequences described in SEQ ID NOs: 86, 87, and 88, respectively, and L chain CDR 1, 2, and 3 amino acid sequences described in SEQ ID NOs: 206, 207, and 208, respectively; and (B) binds the same epitope of blood coagulation factor X as an antibody having variable domain comprising the amino acid sequence of SEQ ID NO: 21, 25, 29, 33, 37, 41, 45, 49, 53, 161, 209, or 217,
   wherein the antibody functionally substitutes for blood coagulation factor VIII and/or activated blood coagulation factor VIII.

29. A bispecific antibody that recognizes blood coagulation factor IX and/or activated blood coagulation factor IX and blood coagulation factor X, wherein the antibody
   (A) binds the same epitope of blood coagulation factor IX/IXa as an antibody having variable domains comprising the amino acid sequence of SEQ ID NO: 13, 17, 85, 205, or 213; and
   (B) binds the same epitope of blood coagulation factor X as an antibody having H and L variable domains comprising a set of six CDR sequences selected from (i) and (ii):
      (i) H chain CDR 1, 2, and 3 amino acid sequences described in SEQ ID NOs: 22, 23, and 24, respectively, and L chain CDR 1, 2, and 3 amino acid sequences described in SEQ ID NOs: 218, 219, and 220, respectively;
      (ii) H chain CDR 1, 2, and 3 amino acid sequences described in SEQ ID NOs: 162, 163, and 164, respectively, and L chain CDR 1, 2, and 3 amino acid sequences described in SEQ ID NOs: 210, 211, and 212, respectively,
   wherein the antibody functionally substitutes for blood coagulation factor VIII and/or activated blood coagulation factor VIII.

30. A bispecific antibody that recognizes blood coagulation factor IX and/or activated blood coagulation factor IX and blood coagulation factor X, wherein the antibody binds the same epitope of blood coagulation factor IX/IXa as an antibody having variable domain comprising the amino acid sequence of SEQ ID NO: 13, 17, 85, 205, or 213, wherein the antibody functionally substitutes for blood coagulation factor VIII and/or activated blood coagulation factor VIII.

31. A bispecific antibody that recognizes blood coagulation factor IX and/or activated blood coagulation factor IX and blood coagulation factor X, wherein the antibody binds the same epitope of blood coagulation factor IX/IXa as an antibody having H and L variable domains comprising a set of six CDR sequences selected from (a) and (b):
   (a) H chain CDR 1, 2, and 3 amino acid sequences described in SEQ ID NOs: 14, 15, and 16, respectively, and L chain CDR 1, 2, and 3 amino acid sequences described in SEQ ID NOs: 214, 215, and 216, respectively;
   (b) H chain CDR 1, 2, and 3 amino acid sequences described in SEQ ID NOs: 86, 87, and 88, respectively, and L chain CDR 1, 2, and 3 amino acid sequences described in SEQ ID NOs: 206, 207, and 208, respectively,
   wherein the antibody functionally substitutes for blood coagulation factor VIII and/or activated blood coagulation factor VIII.

32. A bispecific antibody that recognizes blood coagulation factor IX and/or activated blood coagulation factor IX and blood coagulation factor X, wherein the antibody binds the same epitope of blood coagulation factor X as an antibody having variable region comprising the amino acid sequence of SEQ ID NO: 21, 25, 29, 33, 37, 41, 45, 49, 53, 161, 209, or 217, wherein the antibody functionally substitutes for blood coagulation factor VIII and/or activated blood coagulation factor VIII.

33. A bispecific antibody that recognizes blood coagulation factor IX and/or activated blood coagulation factor IX and blood coagulation factor X, wherein the antibody
(A) binds the same epitope of blood coagulation factor X as an antibody having H and L variable domains comprising a set of six CDR sequences selected from (a) and (b):
(a) H chain CDR 1, 2, and 3 amino acid sequences described in SEQ ID NOs: 22, 23, and 24, respectively, and L chain CDR 1, 2, and 3 amino acid sequences described in SEQ ID NOs: 218, 219, and 220, respectively;
(b) H chain CDR 1, 2, and 3 amino acid sequences described in SEQ ID NOs: 162, 163, and 164, respectively, and L chain CDR 1, 2, and 3 amino acid sequences described in SEQ ID NOs: 210, 211, and 212, respectively,
wherein the antibody functionally substitutes for blood coagulation factor VIII and/or activated blood coagulation factor VIII.

* * * * *

SEQUENCE LISTING

<160> NUMBER OF SEQ ID NOS: 268

<210> SEQ ID NO 1
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 1
cagctatgaa atacctattg cc                                           22

<210> SEQ ID NO 2
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 2
cttttcataa tcaaaatcac cgg                                          23

<210> SEQ ID NO 3
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 3
attgcctacg gcagccgct                                               19

<210> SEQ ID NO 4
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 4
aaatcaccgg aaccagagcc                                              20

<210> SEQ ID NO 5
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 5
ttactcgcgg cccagccggc catg                                         24

<210> SEQ ID NO 6
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 6
ggaattcggc ccccgaggcc cactcacg                                     28

<210> SEQ ID NO 7
<211> LENGTH: 1215
<212> TYPE: DNA

<213> ORGANISM: Homo sapiens

<400> SEQUENCE: 7

```
ggcctcgggg gccagctttc tgggcaggc caggcctgac cttggctttg ggcagggag      60
ggggctaagg tgaggcaggt ggcgccagcc aggtgcacac ccaatgccca tgagcccaga   120
cactggacgc tgaacctcgc ggacagttaa gaacccaggg gcctctgcgc cctgggccca   180
gctctgtccc acaccgcggt cacatggcac cacctctctt gcagcttcca ccaagggccc   240
atccgtcttc ccctggcgc cctgctccag gagcacctcc gagagcacag ccgccctggg   300
ctgcctggtc aaggactact ccccgaacc ggtgacggtg tcgtggaact caggcgccct   360
gaccagcggc gtgcacacct tcccggctgt cctacagtcc tcaggactct actccctcag   420
cagcgtggtg accgtgccct ccagcagctt gggcacgaag acctacacct gcaacgtaga   480
tcacaagccc agcaacacca aggtggacaa gagagttgag tccaaatatg gtcccccatg   540
cccaccatgc ccagcacctg agttcctggg ggaccatca gtcttcctgt tccccccaaa   600
acccaaggac actctcatga tctcccggac ccctgaggtc acgtgcgtgg tggtggacgt   660
gagccaggaa gaccccgagg tccagttcaa ctggtacgtg gatggcgtgg aggtgcataa   720
tgccaagaca aagccgcggg aggagcagtt caacagcacg taccgtgtgg tcagcgtcct   780
caccgtcctg caccaggact ggctgaacgg caaggagtac aagtgcaagg tctccaacaa   840
aggcctcccg tcctccatcg agaaaaccat ctccaaagcc aaagggcagc ccgagagcc   900
acaggtgtgc accctgcccc catcccagga ggagatgacc aagaaccagg tcagcctgtg   960
gtgcctggtc aaaggcttct accccagcga catcgccgtg gagtgggaga gcaatgggca  1020
gccggagaac aactacaaga ccacgcctcc cgtgctggac tccgacggct ccttcttcct  1080
ctacagcagg ctaaccgtgg acaagagcag gtggcaggag gggaatgtct tctcatgctc  1140
cgtgatgcat gaggctctgc acaaccacta cacacagaag agcctctccc tgtctctggg  1200
taaatgagcg gccgc                                                  1215
```

<210> SEQ ID NO 8
<211> LENGTH: 684
<212> TYPE: DNA
<213> ORGANISM: Homo sapiens

<400> SEQUENCE: 8

```
ggcctcgggg gccgaattcc taaactctga ggggtcgga tgacgtggcc attctttgcc    60
taaagcattg agtttactgc aaggtcagaa aagcatgcaa agccctcaga atggctgcaa   120
agagctccaa caaaacaatt tagaacttta ttaaggaata gggggaagct aggaagaaac   180
tcaaaacatc aagattttaa atacgcttct tggtctcctt gctataatta tctgggataa   240
gcatgctgtt ttctgtctgt ccctaacatg ccctgtgatt atccgcaaac aacacaccca   300
agggcagaac tttgttactt aaacaccatc ctgtttgctt cttcctcag gaactgtggc    360
tgcaccatct gtcttcatct tcccgccatc tgatgagcag ttgaaatctg gaactgcctc   420
tgttgtgtgc ctgctgaata acttctatcc cagagaggcc aaagtacagt ggaaggtgga   480
taacgccctc caatcgggta actcccagga gagtgtcaca gagcaggaca gcaaggacag   540
cacctacagc ctcagcagca ccctgacgct gagcaaagca gactacgaga aacacaaagt   600
ctacgcctgc gaagtcaccc atcagggcct gagctcgccc gtcacaaaga gcttcaacag   660
gggagagtgt tagagggcgg ccgc                                         684
```

<210> SEQ ID NO 9

<211> LENGTH: 1215
<212> TYPE: DNA
<213> ORGANISM: Homo sapiens

<400> SEQUENCE: 9

```
ggcctcgggg gcctcccagg ctctgggcag gcacaggcta ggtgcccta acccaggccc      60
tgcacacaaa ggggcaggtg ctgggctcag acctgccaag agccatatcc gggaggaccc     120
tgcccctgac ctaagcccac cccaaaggcc aaactctcca ctccctcagc tcggacacct    180
tctctcctcc cagattccag taactcccaa tcttctctct gcagcttcca ccaagggccc    240
atccgtcttc cccctggcgc cctgctccag gagcacctcc gagagcacag ccgccctggg    300
ctgcctggtc aaggactact ccccgaacc ggtgacggtg tcgtggaact caggcgccct    360
gaccagcggc gtgcacacct tcccggctgt cctacagtcc tcaggactct actccctcag    420
cagcgtggtg accgtgccct ccagcagctt gggcacgaag acctacacct gcaacgtaga    480
tcacaagccc agcaacacca aggtggacaa gagagttgag tccaaatatg gtcccccatg    540
cccaccatgc ccagcacctg agttcctggg gggaccatca gtcttcctgt tccccccaaa    600
acccaaggac actctcatga tctcccggac ccctgaggtc acgtgcgtgg tggtggacgt    660
gagccaggaa gaccccgagg tccagttcaa ctggtacgtg gatggcgtgg aggtgcataa    720
tgccaagaca aagccgcggg aggagcagtt caacagcacg taccgtgtgg tcagcgtcct    780
caccgtcctg caccaggact ggctgaacgg caaggagtac aagtgcaagg tctccaacaa    840
aggcctcccg tcctccatcg agaaaaccat ctccaaagcc aaagggcagc ccgagagcc    900
acaggtgtac accctgcccc catcccagtg cgagatgacc aagaaccagg tcagcctgtc    960
ctgcgcggtc aaaggcttct atcccagcga catcgccgtg gagtgggaga gcaatgggca   1020
gccggagaac aactacaaga ccacgcctcc cgtgctggac tccgacggct ccttcttcct   1080
cgtgagcagg ctaaccgtgg acaagagcag gtggcaggag gggaatgtct tctcatgctc   1140
cgtgatgcat gaggctctgc acaaccacta cacacagaag agcctctccc tgtctctggg   1200
taaatgagcg gccgc                                                    1215
```

<210> SEQ ID NO 10
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 10

```
cgcaaatggg cggtaggcgt g                                               21
```

<210> SEQ ID NO 11
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 11

```
tagaaggcac agtcgagg                                                   18
```

<210> SEQ ID NO 12
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 12
ctctgaatac tttcaacaag ttac                                              24

<210> SEQ ID NO 13
<211> LENGTH: 116
<212> TYPE: PRT
<213> ORGANISM: Mus musculus

<400> SEQUENCE: 13

Met Glu Val Gln Leu Gln Gln Ser Gly Pro Gly Leu Val Lys Pro Thr
1               5                   10                  15

Gln Ser Leu Ser Leu Thr Cys Ser Val Thr Gly Tyr Ser Ile Thr Ser
            20                  25                  30

Gly Tyr Tyr Trp Thr Trp Ile Arg Gln Phe Pro Gly Asn Asn Leu Glu
        35                  40                  45

Trp Ile Gly Tyr Ile Ser Phe Asp Gly Thr Asn Asp Tyr Asn Pro Ser
    50                  55                  60

Leu Lys Asn Arg Ile Ser Ile Thr Arg Asp Thr Ser Glu Asn Gln Phe
65                  70                  75                  80

Phe Leu Lys Leu Asn Ser Val Thr Thr Glu Asp Thr Ala Thr Tyr Tyr
                85                  90                  95

Cys Ala Arg Gly Pro Pro Cys Thr Tyr Trp Gly Gln Gly Thr Leu Val
            100                 105                 110

Thr Val Ser Ala
        115

<210> SEQ ID NO 14
<211> LENGTH: 6
<212> TYPE: PRT
<213> ORGANISM: Mus musculus

<400> SEQUENCE: 14

Ser Gly Tyr Tyr Trp Thr
1               5

<210> SEQ ID NO 15
<211> LENGTH: 16
<212> TYPE: PRT
<213> ORGANISM: Mus musculus

<400> SEQUENCE: 15

Tyr Ile Ser Phe Asp Gly Thr Asn Asp Tyr Asn Pro Ser Leu Lys Asn
1               5                   10                  15

<210> SEQ ID NO 16
<211> LENGTH: 6
<212> TYPE: PRT
<213> ORGANISM: Mus musculus

<400> SEQUENCE: 16

Gly Pro Pro Cys Thr Tyr
1               5

<210> SEQ ID NO 17
<211> LENGTH: 120
<212> TYPE: PRT
<213> ORGANISM: Mus musculus

<400> SEQUENCE: 17

Met Gln Val Gln Leu Gln Gln Ser Gly Ala Glu Leu Val Arg Pro Gly
1               5                   10                  15

```
Ala Ser Val Lys Leu Ser Cys Thr Ala Ser Gly Phe Asn Ile Lys Asp
            20                  25                  30

Asp Tyr Val His Trp Val Lys Gln Arg Pro Glu Gln Gly Leu Glu Trp
                35                  40                  45

Ile Gly Arg Ile Asp Pro Ala Asp Gly Lys Thr Lys Tyr Ala Pro Lys
    50                  55                  60

Phe Gln Asp Lys Ala Thr Met Thr Ser Asp Thr Ser Ser Asn Thr Ala
 65                  70                  75                  80

Tyr Leu Gln Leu Ser Ser Leu Thr Ser Glu Asp Thr Ala Val Tyr Tyr
                85                  90                  95

Cys Val Arg Trp Arg Ile Tyr Tyr Gly Leu Met Asp Tyr Trp Gly Gln
                100                 105                 110

Gly Thr Ser Val Thr Val Ser Ser
            115                 120
```

<210> SEQ ID NO 18
<211> LENGTH: 5
<212> TYPE: PRT
<213> ORGANISM: Mus musculus

<400> SEQUENCE: 18

```
Asp Asp Tyr Val His
 1               5
```

<210> SEQ ID NO 19
<211> LENGTH: 17
<212> TYPE: PRT
<213> ORGANISM: Mus musculus

<400> SEQUENCE: 19

```
Arg Ile Asp Pro Ala Asp Gly Lys Thr Lys Tyr Ala Pro Lys Phe Gln
 1               5                  10                  15

Asp
```

<210> SEQ ID NO 20
<211> LENGTH: 10
<212> TYPE: PRT
<213> ORGANISM: Mus musculus

<400> SEQUENCE: 20

```
Trp Arg Ile Tyr Tyr Gly Leu Met Asp Tyr
 1               5                  10
```

<210> SEQ ID NO 21
<211> LENGTH: 123
<212> TYPE: PRT
<213> ORGANISM: Mus musculus

<400> SEQUENCE: 21

```
Met Gln Val Gln Leu Gln Gln Ser Gly Pro Glu Leu Val Lys Pro Gly
 1               5                  10                  15

Ala Ser Val Lys Met Ser Cys Lys Ala Ser Gly Tyr Thr Phe Thr His
            20                  25                  30

Phe Val Leu His Trp Val Lys Gln Asn Pro Gly Gln Gly Leu Glu Trp
                35                  40                  45

Ile Gly Tyr Ile Ile Pro Tyr Asn Asp Gly Thr Lys Tyr Asn Glu Lys
    50                  55                  60

Phe Lys Gly Lys Ala Thr Leu Thr Ser Asp Lys Ser Ser Ser Thr Ala
 65                  70                  75                  80

Tyr Met Glu Leu Ser Ser Leu Thr Ser Glu Asp Ser Ala Val Tyr Tyr
```

```
                    85                  90                  95
Cys Ala Arg Gly Asn Arg Tyr Asp Val Gly Ser Tyr Ala Met Asp Tyr
            100                 105                 110

Trp Gly Gln Gly Thr Ser Val Thr Val Ser Ser
        115                 120
```

<210> SEQ ID NO 22
<211> LENGTH: 5
<212> TYPE: PRT
<213> ORGANISM: Mus musculus

<400> SEQUENCE: 22

```
His Phe Val Leu His
1               5
```

<210> SEQ ID NO 23
<211> LENGTH: 17
<212> TYPE: PRT
<213> ORGANISM: Mus musculus

<400> SEQUENCE: 23

```
Tyr Ile Ile Pro Tyr Asn Asp Gly Thr Lys Tyr Asn Glu Lys Phe Lys
1               5                   10                  15

Gly
```

<210> SEQ ID NO 24
<211> LENGTH: 13
<212> TYPE: PRT
<213> ORGANISM: Mus musculus

<400> SEQUENCE: 24

```
Gly Asn Arg Tyr Asp Val Gly Ser Tyr Ala Met Asp Tyr
1               5                   10
```

<210> SEQ ID NO 25
<211> LENGTH: 117
<212> TYPE: PRT
<213> ORGANISM: Mus musculus

<400> SEQUENCE: 25

```
Met Gln Val Gln Leu Gln Gln Ser Gly Ala Glu Leu Val Lys Pro Gly
1               5                   10                  15

Ala Ser Val Lys Leu Ser Cys Thr Val Ser Gly Phe Asn Ile Gln Asp
            20                  25                  30

Asn Tyr Met His Trp Val Lys Gln Arg Pro Glu Gln Gly Leu Glu Trp
        35                  40                  45

Ile Gly Arg Ile Asp Pro Ala Asn Gly Asn Thr Arg Tyr Asp Pro Lys
    50                  55                  60

Phe Gln Gly Lys Ala Thr Ile Thr Ala Asp Ile Ser Ser Asn Thr Thr
65                  70                  75                  80

Cys Leu Gln Leu Ser Ser Leu Thr Ser Glu Asp Thr Ala Val Tyr Tyr
                85                  90                  95

Cys Ala Ser Pro Tyr Tyr Pro Leu Gly Cys Trp Gly Gln Gly Thr Leu
            100                 105                 110

Val Thr Val Ser Ala
        115
```

<210> SEQ ID NO 26
<211> LENGTH: 5
<212> TYPE: PRT
<213> ORGANISM: Mus musculus

```
<400> SEQUENCE: 26

Asp Asn Tyr Met His
1               5

<210> SEQ ID NO 27
<211> LENGTH: 17
<212> TYPE: PRT
<213> ORGANISM: Mus musculus

<400> SEQUENCE: 27

Arg Ile Asp Pro Ala Asn Gly Asn Thr Arg Tyr Asp Pro Lys Phe Gln
1               5                   10                  15

Gly

<210> SEQ ID NO 28
<211> LENGTH: 7
<212> TYPE: PRT
<213> ORGANISM: Mus musculus

<400> SEQUENCE: 28

Pro Tyr Tyr Pro Leu Gly Cys
1               5

<210> SEQ ID NO 29
<211> LENGTH: 116
<212> TYPE: PRT
<213> ORGANISM: Mus musculus

<400> SEQUENCE: 29

Met Gln Val Gln Leu Gln Gln Ser Gly Pro Glu Leu Val Lys Pro Gly
1               5                   10                  15

Ala Ser Val Lys Ile Ser Cys Lys Thr Ser Gly Tyr Thr Phe Thr Glu
            20                  25                  30

Asn Thr Ile Tyr Trp Val Lys Gln Ser His Gly Lys Ser Leu Glu Trp
        35                  40                  45

Ile Gly Ser Ile Thr Thr Tyr Asn Gln Lys Phe Lys Asp Lys Ala Thr
    50                  55                  60

Leu Thr Ile Asp Lys Ser Ser Ser Ser Ala Tyr Met Glu Leu Arg Ser
65                  70                  75                  80

Leu Thr Ser Glu Glu Ser Ala Val Tyr Tyr Cys Ala Arg Ser Gly Gly
                85                  90                  95

Arg Gly Lys Pro Tyr Tyr Phe Asp Ser Trp Gly Gln Gly Thr Thr Leu
            100                 105                 110

Thr Val Ser Ser
        115

<210> SEQ ID NO 30
<211> LENGTH: 5
<212> TYPE: PRT
<213> ORGANISM: Mus musculus

<400> SEQUENCE: 30

Glu Asn Thr Ile Tyr
1               5

<210> SEQ ID NO 31
<211> LENGTH: 11
<212> TYPE: PRT
<213> ORGANISM: Mus musculus

<400> SEQUENCE: 31
```

```
Ser Ile Thr Thr Tyr Asn Gln Lys Phe Lys Asp
1               5                   10
```

<210> SEQ ID NO 32
<211> LENGTH: 12
<212> TYPE: PRT
<213> ORGANISM: Mus musculus

<400> SEQUENCE: 32

```
Ser Gly Gly Arg Gly Lys Pro Tyr Tyr Phe Asp Ser
1               5                   10
```

<210> SEQ ID NO 33
<211> LENGTH: 117
<212> TYPE: PRT
<213> ORGANISM: Mus musculus

<400> SEQUENCE: 33

```
Met Gln Val Gln Leu Gln Gln Ser Gly Ser Glu Leu Val Lys Pro Gly
1               5                   10                  15

Ala Ser Val Lys Leu Ser Cys Thr Ala Ser Gly Phe Asn Ile Lys Asp
            20                  25                  30

Asn Tyr Met His Trp Ile Lys Gln Arg Pro Glu Gln Gly Leu Glu Trp
        35                  40                  45

Ile Gly Arg Ile Asp Pro Gly Asn Gly Asn Ser Arg Tyr Asp Pro Lys
    50                  55                  60

Phe Gln Gly Lys Ala Thr Ile Thr Ala Asp Thr Ser Ser Asn Thr Ala
65                  70                  75                  80

Tyr Leu Gln Leu Ser Ser Leu Thr Ser Glu Asp Thr Ala Val Tyr Tyr
                85                  90                  95

Cys Ala Ser Pro Tyr Tyr Pro Leu Gly Tyr Trp Gly Gln Gly Thr Leu
            100                 105                 110

Val Thr Val Ser Ala
        115
```

<210> SEQ ID NO 34
<211> LENGTH: 5
<212> TYPE: PRT
<213> ORGANISM: Mus musculus

<400> SEQUENCE: 34

```
Asp Asn Tyr Met His
1               5
```

<210> SEQ ID NO 35
<211> LENGTH: 17
<212> TYPE: PRT
<213> ORGANISM: Mus musculus

<400> SEQUENCE: 35

```
Arg Ile Asp Pro Gly Asn Gly Asn Ser Arg Tyr Asp Pro Lys Phe Gln
1               5                   10                  15

Gly
```

<210> SEQ ID NO 36
<211> LENGTH: 7
<212> TYPE: PRT
<213> ORGANISM: Mus musculus

<400> SEQUENCE: 36

```
Pro Tyr Tyr Pro Leu Gly Tyr
```

<210> SEQ ID NO 37
<211> LENGTH: 114
<212> TYPE: PRT
<213> ORGANISM: Mus musculus

<400> SEQUENCE: 37

Met Gln Val Gln Leu Gln Gln Ser Gly Ala Glu Leu Val Arg Pro Gly
1               5                   10                  15

Ala Ser Val Lys Leu Ser Cys Thr Val Ser Gly Phe Asn Ile Lys Asp
            20                  25                  30

Asp Tyr Ile His Trp Val Lys Gln Arg Pro Glu Gln Gly Leu Glu Trp
        35                  40                  45

Ile Gly Arg Ile Asp Pro Thr Asn Gly Asn Pro Ala Tyr Ala Pro Lys
    50                  55                  60

Phe Gln Asp Lys Ala Thr Ile Thr Ala Asp Thr Ser Ser Ile Thr Ala
65                  70                  75                  80

Tyr Leu Gln Leu Asn Ser Leu Thr Ser Glu Asp Thr Ala Val Tyr Tyr
                85                  90                  95

Cys Thr Gly Ser Phe Ala Tyr Trp Gly Gln Gly Thr Leu Val Thr Val
            100                 105                 110

Ser Ala

<210> SEQ ID NO 38
<211> LENGTH: 5
<212> TYPE: PRT
<213> ORGANISM: Mus musculus

<400> SEQUENCE: 38

Asp Asp Tyr Ile His
1               5

<210> SEQ ID NO 39
<211> LENGTH: 17
<212> TYPE: PRT
<213> ORGANISM: Mus musculus

<400> SEQUENCE: 39

Arg Ile Asp Pro Thr Asn Gly Asn Pro Ala Tyr Ala Pro Lys Phe Gln
1               5                   10                  15

Asp

<210> SEQ ID NO 40
<211> LENGTH: 4
<212> TYPE: PRT
<213> ORGANISM: Mus musculus

<400> SEQUENCE: 40

Ser Phe Ala Tyr
1

<210> SEQ ID NO 41
<211> LENGTH: 114
<212> TYPE: PRT
<213> ORGANISM: Mus musculus

<400> SEQUENCE: 41

Met Gln Val Gln Leu Gln Gln Ser Gly Ala Glu Leu Val Arg Pro Gly
1               5                   10                  15

Ala Ser Val Lys Leu Ser Cys Thr Ala Ser Gly Phe Asn Ile Lys Asp

-continued

```
                    20                  25                  30
Asp Tyr Val His Trp Val Lys Gln Arg Pro Glu Gln Gly Leu Glu Trp
            35                  40                  45

Ile Gly Arg Ile His Pro Ala Asn Gly Asn Pro Gln Tyr Ala Pro Lys
        50                  55                  60

Phe Gln Asp Lys Ala Thr Ile Ile Gly Thr Ala Ser Asn Thr Thr
65                  70                  75                  80

Tyr Leu Gln Leu Ser Ser Leu Thr Ser Glu Asp Thr Ala Val Tyr Tyr
                85                  90                  95

Cys Ala Gly Pro Phe Ala Tyr Trp Gly Gln Gly Thr Leu Val Thr Val
            100                 105                 110

Ser Ala

<210> SEQ ID NO 42
<211> LENGTH: 5
<212> TYPE: PRT
<213> ORGANISM: Mus musculus

<400> SEQUENCE: 42

Asp Asp Tyr Val His
1               5

<210> SEQ ID NO 43
<211> LENGTH: 17
<212> TYPE: PRT
<213> ORGANISM: Mus musculus

<400> SEQUENCE: 43

Arg Ile His Pro Ala Asn Gly Asn Pro Gln Tyr Ala Pro Lys Phe Gln
1               5                   10                  15

Asp

<210> SEQ ID NO 44
<211> LENGTH: 4
<212> TYPE: PRT
<213> ORGANISM: Mus musculus

<400> SEQUENCE: 44

Pro Phe Ala Tyr
1

<210> SEQ ID NO 45
<211> LENGTH: 116
<212> TYPE: PRT
<213> ORGANISM: Mus musculus

<400> SEQUENCE: 45

Met Glu Val Gln Leu Gln Glu Ser Gly Pro Gly Leu Val Lys Pro Ser
1               5                   10                  15

Gln Ser Leu Ser Leu Thr Cys Ser Val Thr Gly Tyr Ser Ile Thr Ser
            20                  25                  30

Asn Tyr Tyr Trp Asn Trp Ile Arg Gln Phe Pro Gly Asn Lys Leu Glu
        35                  40                  45

Trp Met Gly Tyr Ile Asn Tyr Asp Gly Ser Asn Asn Tyr Asn Pro Ser
    50                  55                  60

Leu Lys Asn Arg Ile Ser Ile Ser Arg Asp Thr Ser Lys Asn Gln Phe
65                  70                  75                  80

Phe Leu Lys Leu Asn Ser Val Thr Thr Glu Asp Thr Ala Thr Tyr Tyr
                85                  90                  95
```

```
Cys Ala Arg Gly Gly Ala Phe Thr Tyr Trp Gly Gln Gly Thr Leu Val
                100                 105                 110
Thr Val Ser Ala
        115

<210> SEQ ID NO 46
<211> LENGTH: 6
<212> TYPE: PRT
<213> ORGANISM: Mus musculus

<400> SEQUENCE: 46

Ser Asn Tyr Tyr Trp Asn
1               5

<210> SEQ ID NO 47
<211> LENGTH: 16
<212> TYPE: PRT
<213> ORGANISM: Mus musculus

<400> SEQUENCE: 47

Tyr Ile Asn Tyr Asp Gly Ser Asn Asn Tyr Asn Pro Ser Leu Lys Asn
1               5                   10                  15

<210> SEQ ID NO 48
<211> LENGTH: 6
<212> TYPE: PRT
<213> ORGANISM: Mus musculus

<400> SEQUENCE: 48

Gly Gly Ala Phe Thr Tyr
1               5

<210> SEQ ID NO 49
<211> LENGTH: 114
<212> TYPE: PRT
<213> ORGANISM: Mus musculus

<400> SEQUENCE: 49

Met Gln Val Gln Leu Gln Gln Ser Gly Pro Glu Leu Val Lys Pro Gly
1               5                   10                  15

Ala Ser Val Lys Ile Ser Cys Lys Ala Ser Gly Tyr Thr Ile Thr Asp
                20                  25                  30

Asn Lys Met Asp Trp Val Lys Gln Ser His Gly Lys Ser Leu Glu Trp
            35                  40                  45

Ile Gly Tyr Ile Ser Pro Asn Asn Gly Asp Ile Gly Tyr Asn Arg Lys
        50                  55                  60

Phe Arg Asn Lys Ala Thr Leu Thr Val Asp Lys Ser Ser Ser Thr Ala
65                  70                  75                  80

Tyr Met Glu Leu His Ser Leu Thr Ser Glu Asp Ser Ala Val Tyr Tyr
                85                  90                  95

Cys Ala Arg His Arg Ala Tyr Trp Gly Gln Gly Thr Leu Val Thr Val
                100                 105                 110

Ser Ala

<210> SEQ ID NO 50
<211> LENGTH: 5
<212> TYPE: PRT
<213> ORGANISM: Mus musculus

<400> SEQUENCE: 50

Asp Asn Lys Met Asp
1               5
```

```
<210> SEQ ID NO 51
<211> LENGTH: 17
<212> TYPE: PRT
<213> ORGANISM: Mus musculus

<400> SEQUENCE: 51

Tyr Ile Ser Pro Asn Gly Asp Ile Gly Tyr Asn Arg Lys Phe Arg
1               5                   10                  15

Asn

<210> SEQ ID NO 52
<211> LENGTH: 4
<212> TYPE: PRT
<213> ORGANISM: Mus musculus

<400> SEQUENCE: 52

His Arg Ala Tyr
1

<210> SEQ ID NO 53
<211> LENGTH: 121
<212> TYPE: PRT
<213> ORGANISM: Mus musculus

<400> SEQUENCE: 53

Met Asp Val Gln Leu Val Glu Ser Gly Gly Gly Leu Val Lys Pro Gly
1               5                   10                  15

Gly Ser Leu Lys Leu Ser Cys Ala Ala Ser Gly Phe Thr Phe Ser Thr
            20                  25                  30

Tyr Ala Met Ser Trp Val Arg Gln Thr Pro Glu Lys Arg Leu Glu Trp
        35                  40                  45

Val Ala Tyr Ile Ser Asn Gly Gly Ala Asn Thr Tyr Tyr Pro Asp Ser
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Arg Ser Glu Asp Thr Ala Leu Tyr Tyr
                85                  90                  95

Cys Ala Arg Gly Gly Tyr Arg Tyr Pro Tyr Ala Met Asp Tyr Trp Gly
            100                 105                 110

Gln Gly Thr Ser Val Thr Val Ser Ser
        115                 120

<210> SEQ ID NO 54
<211> LENGTH: 5
<212> TYPE: PRT
<213> ORGANISM: Mus musculus

<400> SEQUENCE: 54

Thr Tyr Ala Met Ser
1               5

<210> SEQ ID NO 55
<211> LENGTH: 17
<212> TYPE: PRT
<213> ORGANISM: Mus musculus

<400> SEQUENCE: 55

Tyr Ile Ser Asn Gly Gly Ala Asn Thr Tyr Tyr Pro Asp Ser Val Lys
1               5                   10                  15

Gly
```

```
<210> SEQ ID NO 56
<211> LENGTH: 11
<212> TYPE: PRT
<213> ORGANISM: Mus musculus

<400> SEQUENCE: 56

Gly Gly Tyr Arg Tyr Pro Tyr Ala Met Asp Tyr
1               5                   10

<210> SEQ ID NO 57
<211> LENGTH: 121
<212> TYPE: PRT
<213> ORGANISM: Mus musculus

<400> SEQUENCE: 57

Met Gln Val Gln Leu Gln Gln Ser Gly Ala Glu Leu Val Arg Pro Gly
1               5                   10                  15

Ala Ser Val Lys Leu Ser Cys Lys Ala Ser Gly Tyr Thr Phe Thr Ser
            20                  25                  30

Tyr Trp Met His Trp Val Gln Gln Arg Pro Gly Arg Gly Leu Glu Trp
        35                  40                  45

Ile Gly Arg Ile His Pro Ser Asp Ser Glu Ala Arg Tyr Asn Gln Lys
    50                  55                  60

Phe Lys Ser Lys Ala Thr Leu Thr Val Asp Lys Ser Ser Ser Thr Ala
65                  70                  75                  80

Tyr Ile Gln Leu Ser Ser Leu Thr Ser Glu Asp Ser Ala Val Tyr Tyr
                85                  90                  95

Cys Ala Arg Arg Gly Glu Tyr Pro Ser Tyr Thr Met Asp Tyr Trp Gly
            100                 105                 110

Gln Gly Thr Thr Leu Thr Val Ser Ser
        115                 120

<210> SEQ ID NO 58
<211> LENGTH: 5
<212> TYPE: PRT
<213> ORGANISM: Mus musculus

<400> SEQUENCE: 58

Ser Tyr Trp Met His
1               5

<210> SEQ ID NO 59
<211> LENGTH: 17
<212> TYPE: PRT
<213> ORGANISM: Mus musculus

<400> SEQUENCE: 59

Arg Ile His Pro Ser Asp Ser Glu Ala Arg Tyr Asn Gln Lys Phe Lys
1               5                   10                  15

Ser

<210> SEQ ID NO 60
<211> LENGTH: 11
<212> TYPE: PRT
<213> ORGANISM: Mus musculus

<400> SEQUENCE: 60

Arg Gly Glu Tyr Pro Ser Tyr Thr Met Asp Tyr
1               5                   10
```

```
<210> SEQ ID NO 61
<211> LENGTH: 119
<212> TYPE: PRT
<213> ORGANISM: Mus musculus

<400> SEQUENCE: 61

Met Gln Val Gln Leu Gln Gln Ser Gly Thr Val Leu Ala Arg Pro Gly
1               5                   10                  15

Ala Ser Val Lys Met Ser Cys Lys Ala Ser Gly Tyr Thr Phe Thr Ser
            20                  25                  30

Tyr Trp Met His Trp Val Lys Gln Arg Pro Gly Gln Gly Leu Glu Trp
        35                  40                  45

Ile Gly Thr Phe Tyr Pro Gly Asn Ser Asp Ser Asn Tyr Asn Gln Lys
50                  55                  60

Phe Lys Gly Lys Ala Lys Leu Thr Ala Val Thr Ser Ser Ser Thr Ala
65                  70                  75                  80

Tyr Met Glu Leu Ser Ser Leu Thr Asn Glu Asp Ser Ala Val Tyr Tyr
                85                  90                  95

Cys Thr Gly Tyr Tyr Gly Asn Tyr Cys Phe Gly Tyr Trp Gly Gln Gly
            100                 105                 110

Thr Leu Val Thr Val Ser Ala
        115

<210> SEQ ID NO 62
<211> LENGTH: 5
<212> TYPE: PRT
<213> ORGANISM: Mus musculus

<400> SEQUENCE: 62

Ser Tyr Trp Met His
1               5

<210> SEQ ID NO 63
<211> LENGTH: 17
<212> TYPE: PRT
<213> ORGANISM: Mus musculus

<400> SEQUENCE: 63

Thr Phe Tyr Pro Gly Asn Ser Asp Ser Asn Tyr Asn Gln Lys Phe Lys
1               5                   10                  15

Gly

<210> SEQ ID NO 64
<211> LENGTH: 9
<212> TYPE: PRT
<213> ORGANISM: Mus musculus

<400> SEQUENCE: 64

Tyr Tyr Gly Asn Tyr Cys Phe Gly Tyr
1               5

<210> SEQ ID NO 65
<211> LENGTH: 117
<212> TYPE: PRT
<213> ORGANISM: Mus musculus

<400> SEQUENCE: 65

Met Gln Val Gln Leu Gln Gln Ser Gly Ala Glu Leu Val Lys Pro Gly
1               5                   10                  15

Ala Ser Val Lys Leu Ser Cys Ser Ala Ser Gly Phe Asn Ile Lys Asp
            20                  25                  30
```

```
Ser Leu Ile His Trp Val Lys Gln Arg Pro Glu Gln Gly Leu Glu Trp
        35                  40                  45

Ile Gly Trp Ile Asp Pro Glu Asp Gly Arg Thr Lys Tyr Ala Pro Arg
 50                  55                  60

Phe Gln Asp Lys Ala Thr Ile Thr Ala Asp Thr Ser Ser Asn Thr Ala
 65                  70                  75                  80

Tyr Leu Gln Leu Ser Gly Leu Thr Ser Glu Asp Thr Ala Ile Tyr Tyr
                 85                  90                  95

Cys Val Arg Trp Val Tyr Tyr Phe Asp Tyr Trp Gly Gln Gly Thr Thr
            100                 105                 110

Leu Thr Val Ser Ser
        115

<210> SEQ ID NO 66
<211> LENGTH: 5
<212> TYPE: PRT
<213> ORGANISM: Mus musculus

<400> SEQUENCE: 66

Asp Ser Leu Ile His
1               5

<210> SEQ ID NO 67
<211> LENGTH: 17
<212> TYPE: PRT
<213> ORGANISM: Mus musculus

<400> SEQUENCE: 67

Trp Ile Asp Pro Glu Asp Gly Arg Thr Lys Tyr Ala Pro Arg Phe Gln
1               5                  10                  15

Asp

<210> SEQ ID NO 68
<211> LENGTH: 7
<212> TYPE: PRT
<213> ORGANISM: Mus musculus

<400> SEQUENCE: 68

Trp Val Tyr Tyr Phe Asp Tyr
1               5

<210> SEQ ID NO 69
<211> LENGTH: 123
<212> TYPE: PRT
<213> ORGANISM: Mus musculus

<400> SEQUENCE: 69

Met Gln Val Gln Leu Gln Gln Ser Gly Ala Glu Leu Ala Lys Pro Gly
1               5                  10                  15

Ala Ser Val Lys Met Ser Cys Lys Ala Ser Gly Tyr Thr Phe Thr Asp
             20                  25                  30

Tyr Trp Met His Trp Val Lys Gln Arg Pro Gly Gln Gly Leu Glu Trp
         35                  40                  45

Ile Gly Glu Ile Asp Ile Ser Asp Gly Ser Thr Thr Tyr Asn Gln Lys
 50                  55                  60

Phe Lys Gly Lys Ala Thr Leu Thr Val Asp Glu Ser Ser Asn Thr Ala
 65                  70                  75                  80

Tyr Met Gln Leu Ser Ser Leu Thr Ser Glu Asp Ser Ala Val Tyr Tyr
                 85                  90                  95

Cys Ala Arg Gly Glu Asp Tyr Asp Gly Ser His Asp Ala Met Asp Tyr
```

Trp Gly Gln Gly Thr Ser Val Thr Val Ser Ser
        115                 120

<210> SEQ ID NO 70
<211> LENGTH: 5
<212> TYPE: PRT
<213> ORGANISM: Mus musculus

<400> SEQUENCE: 70

Asp Tyr Trp Met His
1               5

<210> SEQ ID NO 71
<211> LENGTH: 17
<212> TYPE: PRT
<213> ORGANISM: Mus musculus

<400> SEQUENCE: 71

Glu Ile Asp Ile Ser Asp Gly Ser Thr Thr Tyr Asn Gln Lys Phe Lys
1               5                   10                  15

Gly

<210> SEQ ID NO 72
<211> LENGTH: 13
<212> TYPE: PRT
<213> ORGANISM: Mus musculus

<400> SEQUENCE: 72

Gly Glu Asp Tyr Asp Gly Ser His Asp Ala Met Asp Tyr
1               5                   10

<210> SEQ ID NO 73
<211> LENGTH: 123
<212> TYPE: PRT
<213> ORGANISM: Mus musculus

<400> SEQUENCE: 73

Met Gln Val Gln Leu Gln Gln Ser Gly Ala Glu Leu Val Met Pro Gly
1               5                   10                  15

Ala Ser Val Lys Met Ser Cys Lys Ala Ser Gly Tyr Thr Phe Thr Asp
            20                  25                  30

Tyr Trp Met His Trp Val Lys Gln Arg Pro Gly Gln Gly Leu Glu Trp
        35                  40                  45

Ile Gly Glu Ile Asp Ile Ser Asp Ser Ser Thr Thr Tyr Asn Gln Lys
    50                  55                  60

Phe Lys Gly Lys Ala Thr Leu Thr Val Asp Glu Ser Ser Asn Thr Ala
65                  70                  75                  80

Tyr Met Gln Leu Ser Ser Leu Thr Ser Glu Asp Ser Ala Val Tyr Tyr
                85                  90                  95

Cys Val Arg Gly Glu Asp Tyr Asp Gly Arg Tyr Asn Val Met Asp Tyr
            100                 105                 110

Trp Gly Gln Gly Thr Ser Val Thr Val Ser Ser
        115                 120

<210> SEQ ID NO 74
<211> LENGTH: 5
<212> TYPE: PRT
<213> ORGANISM: Mus musculus

<400> SEQUENCE: 74

Asp Tyr Trp Met His
1               5

<210> SEQ ID NO 75
<211> LENGTH: 17
<212> TYPE: PRT
<213> ORGANISM: Mus musculus

<400> SEQUENCE: 75

Glu Ile Asp Ile Ser Asp Ser Ser Thr Thr Tyr Asn Gln Lys Phe Lys
1               5                   10                  15

Gly

<210> SEQ ID NO 76
<211> LENGTH: 13
<212> TYPE: PRT
<213> ORGANISM: Mus musculus

<400> SEQUENCE: 76

Gly Glu Asp Tyr Asp Gly Arg Tyr Asn Val Met Asp Tyr
1               5                   10

<210> SEQ ID NO 77
<211> LENGTH: 123
<212> TYPE: PRT
<213> ORGANISM: Mus musculus

<400> SEQUENCE: 77

Met Gln Val Gln Leu Gln Gln Pro Gly Gly Glu Leu Val Met Pro Gly
1               5                   10                  15

Ala Ser Val Lys Met Ser Cys Lys Ala Ser Gly Tyr Thr Phe Thr Asp
                20                  25                  30

Tyr Trp Met His Trp Val Arg Gln Arg Pro Gly Gln Gly Leu Glu Trp
            35                  40                  45

Ile Gly Glu Ile Asp Ile Ser Asp Gly His Thr Thr Tyr Asn Gln Glu
        50                  55                  60

Phe Lys Gly Lys Ala Thr Leu Thr Val Asp Glu Ser Ser Ser Thr Ala
65                  70                  75                  80

Tyr Met Gln Leu Asn Ser Leu Thr Ser Glu Asp Ser Ala Val Tyr Tyr
                85                  90                  95

Cys Ala Arg Gly Glu Asp Tyr Asp Gly Ser Asn Asp Val Met Asp Tyr
            100                 105                 110

Trp Gly Gln Gly Thr Ser Val Thr Val Ser Ser
        115                 120

<210> SEQ ID NO 78
<211> LENGTH: 5
<212> TYPE: PRT
<213> ORGANISM: Mus musculus

<400> SEQUENCE: 78

Asp Tyr Trp Met His
1               5

<210> SEQ ID NO 79
<211> LENGTH: 17
<212> TYPE: PRT
<213> ORGANISM: Mus musculus

<400> SEQUENCE: 79

Glu Ile Asp Ile Ser Asp Gly His Thr Thr Tyr Asn Gln Glu Phe Lys
1               5                   10                  15

Gly

<210> SEQ ID NO 80
<211> LENGTH: 13
<212> TYPE: PRT
<213> ORGANISM: Mus musculus

<400> SEQUENCE: 80

Gly Glu Asp Tyr Asp Gly Ser Asn Asp Val Met Asp Tyr
1               5                   10

<210> SEQ ID NO 81
<211> LENGTH: 123
<212> TYPE: PRT
<213> ORGANISM: Mus musculus

<400> SEQUENCE: 81

Met Gln Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Thr Asp
            20                  25                  30

Tyr Trp Met His Trp Val Lys Gln Arg Pro Gly Gln Gly Leu Glu Trp
        35                  40                  45

Ile Gly Glu Ile Asp Ile Ser Asp Ser His Thr Thr Tyr Asn Gln Lys
    50                  55                  60

Phe Lys Gly Lys Ala Thr Leu Thr Val Asp Glu Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Val Arg Gly Glu Asp Tyr Asp Gly Ser His Asp Val Met Asp Tyr
            100                 105                 110

Trp Gly Gln Gly Thr Ser Val Thr Val Ser Ser
        115                 120

<210> SEQ ID NO 82
<211> LENGTH: 5
<212> TYPE: PRT
<213> ORGANISM: Mus musculus

<400> SEQUENCE: 82

Asp Tyr Trp Met His
1               5

<210> SEQ ID NO 83
<211> LENGTH: 17
<212> TYPE: PRT
<213> ORGANISM: Mus musculus

<400> SEQUENCE: 83

Glu Ile Asp Ile Ser Asp Ser His Thr Thr Tyr Asn Gln Lys Phe Lys
1               5                   10                  15

Gly

<210> SEQ ID NO 84
<211> LENGTH: 13
<212> TYPE: PRT
<213> ORGANISM: Mus musculus

<400> SEQUENCE: 84

Gly Glu Asp Tyr Asp Gly Ser His Asp Val Met Asp Tyr
1               5                   10

<210> SEQ ID NO 85
<211> LENGTH: 119
<212> TYPE: PRT
<213> ORGANISM: Mus musculus

<400> SEQUENCE: 85

Met Gln Val Gln Leu Gln Gln Ser Gly Ala Glu Leu Ala Lys Pro Gly
1               5                   10                  15

Ala Ser Val Lys Leu Ser Cys Lys Ala Ser Gly Tyr Thr Phe Thr Ser
            20                  25                  30

Ser Trp Met His Trp Ile Lys Gln Arg Pro Gly Gln Gly Leu Glu Trp
        35                  40                  45

Leu Gly Tyr Ile Asn Pro Ser Ser Gly Tyr Thr Lys Tyr Asn Arg Lys
    50                  55                  60

Phe Arg Asp Lys Ala Thr Leu Thr Ala Asp Lys Ser Ser Ser Thr Ala
65                  70                  75                  80

Tyr Met Gln Leu Thr Ser Leu Thr Tyr Glu Asp Ser Ala Val Tyr Tyr
                85                  90                  95

Cys Ala Arg Gly Gly Asn Gly Tyr Tyr Phe Asp Tyr Trp Gly Gln Gly
            100                 105                 110

Thr Thr Leu Thr Val Ser Ser
        115

<210> SEQ ID NO 86
<211> LENGTH: 5
<212> TYPE: PRT
<213> ORGANISM: Mus musculus

<400> SEQUENCE: 86

Ser Ser Trp Met His
1               5

<210> SEQ ID NO 87
<211> LENGTH: 17
<212> TYPE: PRT
<213> ORGANISM: Mus musculus

<400> SEQUENCE: 87

Tyr Ile Asn Pro Ser Ser Gly Tyr Thr Lys Tyr Asn Arg Lys Phe Arg
1               5                   10                  15

Asp

<210> SEQ ID NO 88
<211> LENGTH: 9
<212> TYPE: PRT
<213> ORGANISM: Mus musculus

<400> SEQUENCE: 88

Gly Gly Asn Gly Tyr Tyr Phe Asp Tyr
1               5

<210> SEQ ID NO 89
<211> LENGTH: 119
<212> TYPE: PRT
<213> ORGANISM: Mus musculus

<400> SEQUENCE: 89

Met Gln Val Gln Leu Gln Gln Ser Gly Ala Glu Leu Ala Lys Pro Gly
1               5                   10                  15

Ala Ser Val Lys Leu Ser Cys Lys Ala Ser Gly Tyr Thr Phe Thr Thr

-continued

```
                    20                  25                  30
Tyr Trp Met His Trp Val Lys Gln Arg Pro Gly Gln Gly Leu Glu Trp
                35                  40                  45
Ile Gly Tyr Ile Asn Pro Ser Ser Gly Tyr Thr Lys Tyr Asn Gln Lys
            50                  55                  60
Phe Lys Val Lys Ala Thr Leu Thr Ala Asp Lys Ser Ser Ser Thr Ala
65                  70                  75                  80
Tyr Met Gln Leu Ser Ser Leu Thr Asp Glu Asp Ser Ala Val Tyr Tyr
                85                  90                  95
Cys Ala Asn Gly Asn Leu Gly Tyr Phe Phe Asp Tyr Trp Gly Gln Gly
            100                 105                 110
Thr Thr Leu Thr Val Ser Ser
            115

<210> SEQ ID NO 90
<211> LENGTH: 5
<212> TYPE: PRT
<213> ORGANISM: Mus musculus

<400> SEQUENCE: 90

Thr Tyr Trp Met His
1               5

<210> SEQ ID NO 91
<211> LENGTH: 17
<212> TYPE: PRT
<213> ORGANISM: Mus musculus

<400> SEQUENCE: 91

Tyr Ile Asn Pro Ser Ser Gly Tyr Thr Lys Tyr Asn Gln Lys Phe Lys
1               5                   10                  15
Val

<210> SEQ ID NO 92
<211> LENGTH: 9
<212> TYPE: PRT
<213> ORGANISM: Mus musculus

<400> SEQUENCE: 92

Gly Asn Leu Gly Tyr Phe Phe Asp Tyr
1               5

<210> SEQ ID NO 93
<211> LENGTH: 119
<212> TYPE: PRT
<213> ORGANISM: Mus musculus

<400> SEQUENCE: 93

Met Glu Val Gln Leu Gln Gln Ser Gly Ala Glu Leu Val Lys Pro Gly
1               5                   10                  15
Ala Ser Val Lys Leu Ser Cys Thr Ala Ser Gly Phe Asn Ile Lys Asp
                20                  25                  30
Tyr Tyr Met His Trp Ile Lys Gln Arg Pro Gly Gln Gly Leu Glu Trp
                35                  40                  45
Leu Gly Tyr Ile Asn Pro Ser Ser Gly Tyr Thr Lys Tyr Asn Arg Lys
            50                  55                  60
Phe Arg Asp Lys Ala Thr Leu Thr Ala Asp Lys Ser Ser Ser Thr Ala
65                  70                  75                  80
Tyr Met Gln Leu Thr Ser Leu Thr Tyr Glu Asp Ser Ala Val Tyr Tyr
                85                  90                  95
```

Cys Ala Arg Gly Gly Asn Gly Tyr Tyr Leu Asp Tyr Trp Gly Gln Gly
            100                 105                 110

Thr Thr Leu Thr Val Ser Ser
            115

<210> SEQ ID NO 94
<211> LENGTH: 5
<212> TYPE: PRT
<213> ORGANISM: Mus musculus

<400> SEQUENCE: 94

Asp Tyr Tyr Met His
1               5

<210> SEQ ID NO 95
<211> LENGTH: 17
<212> TYPE: PRT
<213> ORGANISM: Mus musculus

<400> SEQUENCE: 95

Tyr Ile Asn Pro Ser Ser Gly Tyr Thr Lys Tyr Asn Arg Lys Phe Arg
1               5                   10                  15

Asp

<210> SEQ ID NO 96
<211> LENGTH: 9
<212> TYPE: PRT
<213> ORGANISM: Mus musculus

<400> SEQUENCE: 96

Gly Gly Asn Gly Tyr Tyr Leu Asp Tyr
1               5

<210> SEQ ID NO 97
<211> LENGTH: 118
<212> TYPE: PRT
<213> ORGANISM: Mus musculus

<400> SEQUENCE: 97

Met Glu Val Gln Leu Gln Gln Ser Gly Ala Glu Leu Met Lys Pro Gly
1               5                   10                  15

Ala Ser Val Lys Ile Ser Cys Lys Ala Thr Gly Tyr Thr Leu Ser Asn
            20                  25                  30

Asn Trp Ile Gln Trp Val Lys Gln Arg Pro Gly His Gly Leu Glu Trp
        35                  40                  45

Ile Gly Glu Ile Leu Pro Gly Ser Asp Thr Ile Asn Tyr Asn Glu Lys
    50                  55                  60

Phe Lys Gly Lys Ala Thr Phe Thr Ala Asp Ala Ser Ser Asn Thr Ala
65                  70                  75                  80

Tyr Met Arg Leu Ser Ser Leu Thr Ser Glu Asp Ser Ala Val Tyr Phe
                85                  90                  95

Cys Ala Arg Glu Gly Ala Ser Trp Phe Ala Tyr Trp Gly Gln Gly Thr
            100                 105                 110

Leu Val Thr Val Ser Ala
            115

<210> SEQ ID NO 98
<211> LENGTH: 5
<212> TYPE: PRT
<213> ORGANISM: Mus musculus

<400> SEQUENCE: 98

Asn Asn Trp Ile Gln
1               5

<210> SEQ ID NO 99
<211> LENGTH: 17
<212> TYPE: PRT
<213> ORGANISM: Mus musculus

<400> SEQUENCE: 99

Glu Ile Leu Pro Gly Ser Asp Thr Ile Asn Tyr Asn Glu Lys Phe Lys
1               5                   10                  15

Gly

<210> SEQ ID NO 100
<211> LENGTH: 8
<212> TYPE: PRT
<213> ORGANISM: Mus musculus

<400> SEQUENCE: 100

Glu Gly Ala Ser Trp Phe Ala Tyr
1               5

<210> SEQ ID NO 101
<211> LENGTH: 118
<212> TYPE: PRT
<213> ORGANISM: Mus musculus

<400> SEQUENCE: 101

Met Gln Val Gln Leu Gln Gln Ser Gly Ala Glu Leu Met Lys Pro Gly
1               5                   10                  15

Ala Ser Val Lys Ile Ser Cys Lys Ala Thr Gly Tyr Ser Ile Ser Asn
                20                  25                  30

His Trp Ile Gln Trp Val Lys Gln Arg Pro Gly His Gly Leu Glu Trp
            35                  40                  45

Ile Gly Glu Ile Leu Thr Gly Ser Asp Thr Ile Asn Tyr Asn Glu Lys
        50                  55                  60

Leu Lys Gly Lys Ala Thr Phe Thr Ala Asp Thr Ser Ser Asn Thr Ala
65                  70                  75                  80

Tyr Met Gln Leu Arg Ser Leu Thr Ser Glu Asp Ser Ala Val Tyr Tyr
                85                  90                  95

Cys Ala Arg Glu Gly Ser Ser Trp Phe Ala His Trp Gly Gln Gly Thr
                100                 105                 110

Leu Val Thr Val Ser Ala
            115

<210> SEQ ID NO 102
<211> LENGTH: 5
<212> TYPE: PRT
<213> ORGANISM: Mus musculus

<400> SEQUENCE: 102

Asn His Trp Ile Gln
1               5

<210> SEQ ID NO 103
<211> LENGTH: 17
<212> TYPE: PRT
<213> ORGANISM: Mus musculus

<400> SEQUENCE: 103

```
Glu Ile Leu Thr Gly Ser Asp Thr Ile Asn Tyr Asn Glu Lys Leu Lys
1               5                   10                  15
Gly

<210> SEQ ID NO 104
<211> LENGTH: 8
<212> TYPE: PRT
<213> ORGANISM: Mus musculus

<400> SEQUENCE: 104

Glu Gly Ser Ser Trp Phe Ala His
1               5

<210> SEQ ID NO 105
<211> LENGTH: 118
<212> TYPE: PRT
<213> ORGANISM: Mus musculus

<400> SEQUENCE: 105

Met Gln Val Gln Leu Lys Glu Ser Gly Ala Glu Leu Val Arg Ser Gly
1               5                   10                  15

Ala Ser Val Lys Leu Ser Cys Thr Ala Ser Gly Phe Asn Ile Lys Asp
                20                  25                  30

Tyr Tyr Met His Trp Val Lys Gln Arg Pro Glu Gln Gly Leu Glu Trp
            35                  40                  45

Ile Gly Trp Ser Asp Pro Glu Asn Gly Asn Thr Ile Tyr Asp Pro Lys
        50                  55                  60

Phe Gln Gly Lys Ala Ser Ile Thr Ala Asp Thr Ser Ser Asn Ile Ala
65                  70                  75                  80

Tyr Leu Gln Leu Ser Ser Leu Thr Ser Glu Asp Thr Ala Val Tyr Tyr
                85                  90                  95

Cys Ala Arg Gly Gly Arg Arg Ala Met Asp Tyr Trp Gly Gln Gly Thr
            100                 105                 110

Ser Val Thr Val Ser Ser
            115

<210> SEQ ID NO 106
<211> LENGTH: 5
<212> TYPE: PRT
<213> ORGANISM: Mus musculus

<400> SEQUENCE: 106

Asp Tyr Tyr Met His
1               5

<210> SEQ ID NO 107
<211> LENGTH: 17
<212> TYPE: PRT
<213> ORGANISM: Mus musculus

<400> SEQUENCE: 107

Trp Ser Asp Pro Glu Asn Gly Asn Thr Ile Tyr Asp Pro Lys Phe Gln
1               5                   10                  15
Gly

<210> SEQ ID NO 108
<211> LENGTH: 8
<212> TYPE: PRT
<213> ORGANISM: Mus musculus

<400> SEQUENCE: 108
```

Gly Gly Arg Arg Ala Met Asp Tyr
1               5

<210> SEQ ID NO 109
<211> LENGTH: 119
<212> TYPE: PRT
<213> ORGANISM: Mus musculus

<400> SEQUENCE: 109

Met Glu Val Met Leu Val Glu Ser Gly Pro Gly Leu Val Lys Pro Ser
1               5                   10                  15

Gln Ser Leu Ser Leu Thr Cys Ser Val Thr Gly Tyr Ser Ile Thr Ser
            20                  25                  30

Gly Tyr Tyr Trp Asn Trp Ile Arg Gln Phe Pro Gly Asn Lys Leu Glu
        35                  40                  45

Trp Met Gly Tyr Ile Ser Tyr Asp Gly Thr Asn Lys Tyr Asn Pro Ser
    50                  55                  60

Leu Lys Asn Arg Ile Ser Ile Thr Arg Asp Thr Ser Lys Asn Gln Phe
65                  70                  75                  80

Phe Leu Lys Leu Asn Ser Val Thr Thr Glu Asp Thr Ala Thr Tyr Tyr
                85                  90                  95

Cys Ala Arg Gly Gly Ser Gly His Ala Met Asp Tyr Trp Gly Gln Gly
            100                 105                 110

Thr Ser Val Thr Val Ser Ser
        115

<210> SEQ ID NO 110
<211> LENGTH: 6
<212> TYPE: PRT
<213> ORGANISM: Mus musculus

<400> SEQUENCE: 110

Ser Gly Tyr Tyr Trp Asn
1               5

<210> SEQ ID NO 111
<211> LENGTH: 16
<212> TYPE: PRT
<213> ORGANISM: Mus musculus

<400> SEQUENCE: 111

Tyr Ile Ser Tyr Asp Gly Thr Asn Lys Tyr Asn Pro Ser Leu Lys Asn
1               5                   10                  15

<210> SEQ ID NO 112
<211> LENGTH: 9
<212> TYPE: PRT
<213> ORGANISM: Mus musculus

<400> SEQUENCE: 112

Gly Gly Ser Gly His Ala Met Asp Tyr
1               5

<210> SEQ ID NO 113
<211> LENGTH: 123
<212> TYPE: PRT
<213> ORGANISM: Mus musculus

<400> SEQUENCE: 113

Met Gln Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Thr Asn

```
                     20                  25                  30
Tyr Leu Met His Trp Val Lys Gln Lys Pro Gly Gln Gly Leu Glu Trp
            35                  40                  45
Ile Gly Phe Ile Ile Pro Tyr Asn Asp Gly Thr Lys Tyr Asn Glu Lys
        50                  55                  60
Phe Lys Gly Lys Ala Thr Val Thr Ser Asp Lys Ser Ser Ser Thr Ala
 65                  70                  75                  80
Tyr Met Glu Leu Ser Ser Leu Thr Ser Glu Asp Ser Ala Val Tyr Tyr
                85                  90                  95
Cys Ala Arg Gly Asn Arg Tyr Asp Val Gly Tyr Tyr Ala Met Asp Tyr
            100                 105                 110
Trp Gly Gln Gly Thr Ser Val Thr Val Ser Ser
        115                 120

<210> SEQ ID NO 114
<211> LENGTH: 5
<212> TYPE: PRT
<213> ORGANISM: Mus musculus

<400> SEQUENCE: 114

Asn Tyr Leu Met His
 1               5

<210> SEQ ID NO 115
<211> LENGTH: 17
<212> TYPE: PRT
<213> ORGANISM: Mus musculus

<400> SEQUENCE: 115

Phe Ile Ile Pro Tyr Asn Asp Gly Thr Lys Tyr Asn Glu Lys Phe Lys
 1               5                  10                  15
Gly

<210> SEQ ID NO 116
<211> LENGTH: 13
<212> TYPE: PRT
<213> ORGANISM: Mus musculus

<400> SEQUENCE: 116

Gly Asn Arg Tyr Asp Val Gly Tyr Tyr Ala Met Asp Tyr
 1               5                  10

<210> SEQ ID NO 117
<211> LENGTH: 128
<212> TYPE: PRT
<213> ORGANISM: Mus musculus

<400> SEQUENCE: 117

Met Glu Val Lys Leu Val Glu Ser Gly Gly Gly Ser Val Lys Pro Gly
 1               5                  10                  15
Gly Ser Leu Lys Leu Ser Cys Ala Ala Ser Gly Phe Thr Phe Ser Ser
            20                  25                  30
Asn Ala Met Ser Trp Val Arg Gln Thr Pro Glu Arg Ser Leu Glu Trp
        35                  40                  45
Val Ala Thr Ile Ser Ser Ala Gly Arg Ser Thr Tyr Tyr Pro Asp Ser
    50                  55                  60
Val Lys Gly Arg Phe Ile Ile Ser Arg Asp Asn Leu Lys Asn Ile Leu
 65                  70                  75                  80
Tyr Leu Gln Met Ser Ser Leu Arg Ser Ala Asp Thr Ala Met Tyr Tyr
                85                  90                  95
```

Cys Ala Arg His Glu Ala Ser Ile Met Ile Thr Thr Gly Arg Ile Trp
            100                 105                 110

Ala Trp Phe Gly Asn Trp Gly Gln Gly Thr Leu Val Thr Val Ser Ala
        115                 120                 125

<210> SEQ ID NO 118
<211> LENGTH: 5
<212> TYPE: PRT
<213> ORGANISM: Mus musculus

<400> SEQUENCE: 118

Ser Asn Ala Met Ser
1               5

<210> SEQ ID NO 119
<211> LENGTH: 17
<212> TYPE: PRT
<213> ORGANISM: Mus musculus

<400> SEQUENCE: 119

Thr Ile Ser Ser Ala Gly Arg Ser Thr Tyr Tyr Pro Asp Ser Val Lys
1               5                   10                  15

Gly

<210> SEQ ID NO 120
<211> LENGTH: 18
<212> TYPE: PRT
<213> ORGANISM: Mus musculus

<400> SEQUENCE: 120

His Glu Ala Ser Ile Met Ile Thr Thr Gly Arg Ile Trp Ala Trp Phe
1               5                   10                  15

Gly Asn

<210> SEQ ID NO 121
<211> LENGTH: 124
<212> TYPE: PRT
<213> ORGANISM: Mus musculus

<400> SEQUENCE: 121

Met Asp Val Gln Leu Val Glu Ser Gly Gly Leu Val Lys Pro Gly
1               5                   10                  15

Gly Ser Leu Lys Leu Ser Cys Val Ala Ser Gly Phe Thr Phe Arg Arg
            20                  25                  30

Tyr Ala Met Ser Trp Val Arg Gln Thr Pro Glu Lys Arg Leu Glu Trp
        35                  40                  45

Val Ala Thr Ile Ser Ser Gly Gly Ser Tyr Asn Tyr His Pro Asp Ser
    50                  55                  60

Val Lys Asp Arg Leu Thr Ile Ser Arg Asp Asp Ala Lys Asn Thr Leu
65                  70                  75                  80

Tyr Leu Gln Met Ser Ser Leu Arg Ser Glu Asp Thr Ala Met Tyr Tyr
                85                  90                  95

Cys Val Arg His Val Leu Leu Thr Thr Ile Gly Tyr Tyr Ala Ile Asp
            100                 105                 110

Tyr Trp Gly Gln Gly Thr Ser Val Thr Val Ser Ser
        115                 120

<210> SEQ ID NO 122
<211> LENGTH: 5
<212> TYPE: PRT

<213> ORGANISM: Mus musculus

<400> SEQUENCE: 122

Arg Tyr Ala Met Ser
1               5

<210> SEQ ID NO 123
<211> LENGTH: 17
<212> TYPE: PRT
<213> ORGANISM: Mus musculus

<400> SEQUENCE: 123

Thr Ile Ser Ser Gly Gly Ser Tyr Asn Tyr His Pro Asp Ser Val Lys
1               5                   10                  15

Asp

<210> SEQ ID NO 124
<211> LENGTH: 14
<212> TYPE: PRT
<213> ORGANISM: Mus musculus

<400> SEQUENCE: 124

His Val Leu Leu Thr Thr Ile Gly Tyr Tyr Ala Ile Asp Tyr
1               5                   10

<210> SEQ ID NO 125
<211> LENGTH: 124
<212> TYPE: PRT
<213> ORGANISM: Mus musculus

<400> SEQUENCE: 125

Met Glu Val Gln Leu Gln Gln Ser Gly Gly Val Leu Val Lys Pro Gly
1               5                   10                  15

Arg Ser Leu Lys Leu Ser Cys Ala Ala Ser Gly Phe Thr Phe Ser Arg
            20                  25                  30

Tyr Thr Met Ser Trp Val Arg Gln Thr Pro Glu Lys Arg Leu Glu Trp
        35                  40                  45

Val Ala Thr Ile Ser Gly Gly Ser Tyr Thr Tyr Tyr Pro Asp Ser
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Arg Ser Glu Asp Thr Ala Met Tyr Tyr
                85                  90                  95

Cys Ala Arg His Val Leu Gln Thr Met Ile Gly Tyr Tyr Ala Val Asp
            100                 105                 110

Tyr Trp Gly Gln Gly Thr Ser Val Thr Val Ser Ser
        115                 120

<210> SEQ ID NO 126
<211> LENGTH: 5
<212> TYPE: PRT
<213> ORGANISM: Mus musculus

<400> SEQUENCE: 126

Arg Tyr Thr Met Ser
1               5

<210> SEQ ID NO 127
<211> LENGTH: 17
<212> TYPE: PRT
<213> ORGANISM: Mus musculus

```
<400> SEQUENCE: 127

Thr Ile Ser Gly Gly Ser Tyr Thr Tyr Tyr Pro Asp Ser Val Lys
1               5                   10                  15

Gly

<210> SEQ ID NO 128
<211> LENGTH: 14
<212> TYPE: PRT
<213> ORGANISM: Mus musculus

<400> SEQUENCE: 128

His Val Leu Gln Thr Met Ile Gly Tyr Tyr Ala Val Asp Tyr
1               5                   10

<210> SEQ ID NO 129
<211> LENGTH: 124
<212> TYPE: PRT
<213> ORGANISM: Mus musculus

<400> SEQUENCE: 129

Met Glu Val Lys Leu Val Glu Ser Gly Gly Gly Leu Val Lys Pro Gly
1               5                   10                  15

Arg Ser Leu Lys Val Ser Cys Ala Ala Ser Gly Phe Thr Phe Ser Arg
            20                  25                  30

Tyr Thr Met Ser Trp Val Arg Gln Thr Pro Glu Lys Arg Leu Glu Trp
        35                  40                  45

Val Ala Thr Ile Ser Gly Gly Gly Tyr Thr Tyr Tyr Pro Asp Ser
    50                  55                  60

Val Lys Gly Arg Phe Thr Ile Ser Arg Glu Asn Ala Lys Asn Thr Leu
65                  70                  75                  80

Tyr Leu Gln Met Ser Ser Leu Arg Ser Glu Asp Thr Ala Val Tyr Tyr
                85                  90                  95

Cys Val Arg His Val Leu Gln Thr Thr Ile Gly Tyr Tyr Ala Val Asp
            100                 105                 110

Tyr Trp Gly Gln Gly Thr Ser Val Thr Val Ser Ser
        115                 120

<210> SEQ ID NO 130
<211> LENGTH: 5
<212> TYPE: PRT
<213> ORGANISM: Mus musculus

<400> SEQUENCE: 130

Arg Tyr Thr Met Ser
1               5

<210> SEQ ID NO 131
<211> LENGTH: 17
<212> TYPE: PRT
<213> ORGANISM: Mus musculus

<400> SEQUENCE: 131

Thr Ile Ser Gly Gly Gly Tyr Thr Tyr Tyr Pro Asp Ser Val Lys
1               5                   10                  15

Gly

<210> SEQ ID NO 132
<211> LENGTH: 14
<212> TYPE: PRT
<213> ORGANISM: Mus musculus
```

```
<400> SEQUENCE: 132

His Val Leu Gln Thr Thr Ile Gly Tyr Tyr Ala Val Asp Tyr
1               5                   10

<210> SEQ ID NO 133
<211> LENGTH: 124
<212> TYPE: PRT
<213> ORGANISM: Mus musculus

<400> SEQUENCE: 133

Met Glu Val Lys Leu Val Glu Ser Gly Gly Gly Leu Val Lys Ala Gly
1               5                   10                  15

Gly Ser Leu Lys Leu Ser Cys Ala Ala Ser Gly Phe Thr Phe Ser Arg
            20                  25                  30

Tyr Ala Met Ser Trp Val Arg Gln Thr Pro Glu Lys Arg Leu Glu Trp
        35                  40                  45

Val Ala Thr Ile Ser Ser Gly Gly Arg Tyr Thr Tyr Tyr Pro Asp Ser
    50                  55                  60

Val Lys Gly Arg Phe Thr Ile Ser Arg Asp Asp Ala Gln Asn Thr Leu
65                  70                  75                  80

Tyr Leu Gln Met Ser Ser Leu Arg Ser Glu Asp Thr Ala Met Tyr Tyr
                85                  90                  95

Cys Ala Arg His Leu Leu Gln Thr Met Ile Gly Tyr Tyr Ala Met Asp
            100                 105                 110

Tyr Trp Gly Gln Gly Thr Ser Val Thr Val Ser Ser
        115                 120

<210> SEQ ID NO 134
<211> LENGTH: 5
<212> TYPE: PRT
<213> ORGANISM: Mus musculus

<400> SEQUENCE: 134

Arg Tyr Ala Met Ser
1               5

<210> SEQ ID NO 135
<211> LENGTH: 17
<212> TYPE: PRT
<213> ORGANISM: Mus musculus

<400> SEQUENCE: 135

Thr Ile Ser Ser Gly Gly Arg Tyr Thr Tyr Tyr Pro Asp Ser Val Lys
1               5                   10                  15

Gly

<210> SEQ ID NO 136
<211> LENGTH: 14
<212> TYPE: PRT
<213> ORGANISM: Mus musculus

<400> SEQUENCE: 136

His Leu Leu Gln Thr Met Ile Gly Tyr Tyr Ala Met Asp Tyr
1               5                   10

<210> SEQ ID NO 137
<211> LENGTH: 120
<212> TYPE: PRT
<213> ORGANISM: Mus musculus

<400> SEQUENCE: 137
```

Met Gln Val Gln Leu Gln Gln Ser Gly Pro Glu Leu Val Lys Pro Gly
1               5                   10                  15

Ala Ser Val Lys Ile Ser Cys Lys Ala Ser Gly Tyr Thr Phe Thr Asp
            20                  25                  30

His Asn Met Asp Trp Val Lys Gln Ser His Gly Lys Ser Leu Glu Trp
        35                  40                  45

Ile Gly Asp Ile Asn Pro Asn Phe Asp Thr Thr Ile Tyr Asn Gln Lys
50                  55                  60

Phe Arg Gly Lys Ala Thr Leu Thr Val Asp Lys Ser Ser Arg Thr Ala
65                  70                  75                  80

Tyr Met Glu Leu Arg Ser Leu Thr Ser Glu Asp Thr Ala Val Tyr Tyr
                85                  90                  95

Cys Ala Arg Arg Gly Tyr Tyr Arg Phe Asp Leu Asp Tyr Trp Gly Gln
            100                 105                 110

Gly Thr Thr Leu Thr Val Ser Ser
            115                 120

<210> SEQ ID NO 138
<211> LENGTH: 5
<212> TYPE: PRT
<213> ORGANISM: Mus musculus

<400> SEQUENCE: 138

Asp His Asn Met Asp
1               5

<210> SEQ ID NO 139
<211> LENGTH: 17
<212> TYPE: PRT
<213> ORGANISM: Mus musculus

<400> SEQUENCE: 139

Asp Ile Asn Pro Asn Phe Asp Thr Thr Ile Tyr Asn Gln Lys Phe Arg
1               5                   10                  15

Gly

<210> SEQ ID NO 140
<211> LENGTH: 10
<212> TYPE: PRT
<213> ORGANISM: Mus musculus

<400> SEQUENCE: 140

Arg Gly Tyr Tyr Arg Phe Asp Leu Asp Tyr
1               5                   10

<210> SEQ ID NO 141
<211> LENGTH: 120
<212> TYPE: PRT
<213> ORGANISM: Mus musculus

<400> SEQUENCE: 141

Met Gln Val Gln Leu Gln Gln Phe Gly Ala Glu Leu Val Lys Pro Gly
1               5                   10                  15

Ala Ser Val Lys Met Ser Cys Lys Ala Ser Gly Phe Thr Phe Thr Asp
            20                  25                  30

Asn Asn Met Asp Trp Val Lys Gln Ser His Gly Lys Ser Leu Glu Trp
        35                  40                  45

Ile Gly Asp Ile Asn Pro Asn Tyr Asp Ser Thr Ala Tyr Asn Gln Lys
50                  55                  60

Phe Lys Gly Arg Ala Thr Leu Thr Val Asp Lys Ser Ser Ser Thr Ala

```
                65                  70                  75                  80
Tyr Met Glu Leu Arg Ser Leu Thr Ser Glu Asp Thr Ala Val Tyr Tyr
                    85                  90                  95
Cys Ala Arg Arg Lys Arg Arg Gly Tyr Tyr Phe Asp Tyr Trp Gly Gln
                100                 105                 110
Gly Thr Thr Leu Thr Val Ser Ser
            115                 120

<210> SEQ ID NO 142
<211> LENGTH: 5
<212> TYPE: PRT
<213> ORGANISM: Mus musculus

<400> SEQUENCE: 142

Asp Asn Asn Met Asp
1               5

<210> SEQ ID NO 143
<211> LENGTH: 17
<212> TYPE: PRT
<213> ORGANISM: Mus musculus

<400> SEQUENCE: 143

Asp Ile Asn Pro Asn Tyr Asp Ser Thr Ala Tyr Asn Gln Lys Phe Lys
1               5                   10                  15

Gly

<210> SEQ ID NO 144
<211> LENGTH: 11
<212> TYPE: PRT
<213> ORGANISM: Mus musculus

<400> SEQUENCE: 144

Arg Arg Lys Arg Arg Gly Tyr Tyr Phe Asp Tyr
1               5                   10

<210> SEQ ID NO 145
<211> LENGTH: 120
<212> TYPE: PRT
<213> ORGANISM: Mus musculus

<400> SEQUENCE: 145

Met Glu Val Gln Leu Gln Gln Ser Gly Ala Glu Leu Val Arg Pro Gly
1               5                   10                  15
Ala Ser Val Lys Ile Ser Cys Lys Ala Ser Gly Tyr Thr Phe Thr Asp
                20                  25                  30
Asn Asn Met Asp Trp Val Lys Gln Ser His Gly Lys Ser Leu Glu Trp
            35                  40                  45
Ile Gly Asp Val Asn Pro Asn Tyr Asp Ser Thr Met Tyr Asn Gln Lys
        50                  55                  60
Phe Lys Gly Lys Ala Thr Leu Thr Val Asp Lys Ser Ser Ser Thr Ala
65                  70                  75                  80
Tyr Met Glu Leu Arg Ser Leu Thr Ser Glu Asp Thr Ala Val Tyr Tyr
                    85                  90                  95
Cys Ala Arg Arg Ile Arg Arg Gly Tyr Ser Phe Asp Tyr Trp Gly Gln
                100                 105                 110
Gly Thr Thr Leu Thr Val Ser Ser
            115                 120

<210> SEQ ID NO 146
```

```
<211> LENGTH: 5
<212> TYPE: PRT
<213> ORGANISM: Mus musculus

<400> SEQUENCE: 146

Asp Asn Asn Met Asp
1               5

<210> SEQ ID NO 147
<211> LENGTH: 17
<212> TYPE: PRT
<213> ORGANISM: Mus musculus

<400> SEQUENCE: 147

Asp Val Asn Pro Asn Tyr Asp Ser Thr Met Tyr Asn Gln Lys Phe Lys
1               5                   10                  15

Gly

<210> SEQ ID NO 148
<211> LENGTH: 10
<212> TYPE: PRT
<213> ORGANISM: Mus musculus

<400> SEQUENCE: 148

Arg Ile Arg Arg Gly Tyr Ser Phe Asp Tyr
1               5                   10

<210> SEQ ID NO 149
<211> LENGTH: 120
<212> TYPE: PRT
<213> ORGANISM: Mus musculus

<400> SEQUENCE: 149

Met Glu Val Gln Leu Gln Gln Ser Gly Ala Glu Leu Val Lys Pro Gly
1               5                   10                  15

Ala Ser Val Lys Ile Ser Cys Lys Thr Ser Gly Tyr Thr Phe Thr Asp
                20                  25                  30

Asn Asn Met Asp Trp Val Lys Gln Ser His Gly Lys Ser Leu Glu Trp
            35                  40                  45

Ile Gly Asp Ile Asn Pro Asn Tyr Asp Ser Thr Ile Tyr Asn Gln Lys
        50                  55                  60

Phe Lys Gly Lys Ala Thr Leu Thr Val Asp Lys Ser Ser Asn Thr Ala
65                  70                  75                  80

Tyr Met Glu Leu Arg Ser Leu Thr Ser Glu Asp Thr Ala Val Tyr Tyr
                85                  90                  95

Cys Ala Arg Arg Ile Tyr Tyr Gly Tyr Ala Leu Asp Tyr Trp Gly Gln
            100                 105                 110

Gly Thr Ser Val Thr Val Ser Ser
        115                 120

<210> SEQ ID NO 150
<211> LENGTH: 5
<212> TYPE: PRT
<213> ORGANISM: Mus musculus

<400> SEQUENCE: 150

Asp Asn Asn Met Asp
1               5

<210> SEQ ID NO 151
<211> LENGTH: 17
<212> TYPE: PRT
```

<213> ORGANISM: Mus musculus

<400> SEQUENCE: 151

Asp Ile Asn Pro Asn Tyr Asp Ser Thr Ile Tyr Asn Gln Lys Phe Lys
1               5                   10                  15
Gly

<210> SEQ ID NO 152
<211> LENGTH: 10
<212> TYPE: PRT
<213> ORGANISM: Mus musculus

<400> SEQUENCE: 152

Arg Ile Tyr Tyr Gly Tyr Ala Leu Asp Tyr
1               5                   10

<210> SEQ ID NO 153
<211> LENGTH: 120
<212> TYPE: PRT
<213> ORGANISM: Mus musculus

<400> SEQUENCE: 153

Met Glu Val Gln Leu Gln Gln Ser Gly Ala Glu Leu Val Lys Pro Gly
1               5                   10                  15

Ala Ser Val Lys Ile Ser Cys Lys Ala Ser Gly Tyr Thr Phe Thr Asp
                20                  25                  30

His Asn Met Asp Trp Val Lys Gln Ser His Gly Lys Asn Leu Glu Trp
            35                  40                  45

Ile Gly Asp Ile Asn Pro Asn Tyr Asp Ser Val Ile Ser Asp Gln Lys
        50                  55                  60

Phe Lys Gly Lys Ala Thr Leu Thr Val Asp Lys Ser Ser Ser Thr Ala
65                  70                  75                  80

Tyr Met Glu Leu Arg Ser Leu Thr Ser Glu Asp Thr Ala Val Tyr Tyr
                85                  90                  95

Cys Ala Arg Arg Leu Arg Gly Gly Phe Ala Met Asp Tyr Trp Gly Gln
            100                 105                 110

Gly Thr Ser Val Thr Val Ser Ser
        115                 120

<210> SEQ ID NO 154
<211> LENGTH: 5
<212> TYPE: PRT
<213> ORGANISM: Mus musculus

<400> SEQUENCE: 154

Asp His Asn Met Asp
1               5

<210> SEQ ID NO 155
<211> LENGTH: 17
<212> TYPE: PRT
<213> ORGANISM: Mus musculus

<400> SEQUENCE: 155

Asp Ile Asn Pro Asn Tyr Asp Ser Val Ile Ser Asp Gln Lys Phe Lys
1               5                   10                  15
Gly

<210> SEQ ID NO 156
<211> LENGTH: 10
<212> TYPE: PRT

```
<213> ORGANISM: Mus musculus

<400> SEQUENCE: 156

Arg Leu Arg Gly Gly Phe Ala Met Asp Tyr
1               5                   10

<210> SEQ ID NO 157
<211> LENGTH: 120
<212> TYPE: PRT
<213> ORGANISM: Mus musculus

<400> SEQUENCE: 157

Met Gln Val Gln Leu Gln Gln Ser Gly Thr Val Leu Ala Arg Pro Gly
1               5                   10                  15

Ala Ser Val Lys Ile Ser Cys Lys Thr Ser Gly Tyr Thr Phe Thr Asp
            20                  25                  30

Tyr Asn Met Asp Trp Val Lys Gln Ser His Gly Lys Ser Leu Glu Trp
        35                  40                  45

Ile Gly Asp Ile Asn Pro Asn Tyr Asp Ser Thr Ile Tyr Lys Gln Asn
    50                  55                  60

Phe Lys Gly Arg Ala Thr Leu Thr Val Asp Arg Ser Ser Ser Thr Ala
65                  70                  75                  80

Tyr Met Glu Leu Arg Ser Leu Thr Ser Glu Asp Thr Ala Val Tyr Tyr
                85                  90                  95

Cys Ala Arg Arg Met Arg Arg Gly Tyr Ala Met Asp Tyr Trp Gly Gln
            100                 105                 110

Gly Thr Ser Val Thr Val Ser Ser
        115                 120

<210> SEQ ID NO 158
<211> LENGTH: 5
<212> TYPE: PRT
<213> ORGANISM: Mus musculus

<400> SEQUENCE: 158

Asp Tyr Asn Met Asp
1               5

<210> SEQ ID NO 159
<211> LENGTH: 17
<212> TYPE: PRT
<213> ORGANISM: Mus musculus

<400> SEQUENCE: 159

Asp Ile Asn Pro Asn Tyr Asp Ser Thr Ile Tyr Lys Gln Asn Phe Lys
1               5                   10                  15

Gly

<210> SEQ ID NO 160
<211> LENGTH: 10
<212> TYPE: PRT
<213> ORGANISM: Mus musculus

<400> SEQUENCE: 160

Arg Met Arg Arg Gly Tyr Ala Met Asp Tyr
1               5                   10

<210> SEQ ID NO 161
<211> LENGTH: 120
<212> TYPE: PRT
<213> ORGANISM: Mus musculus
```

<400> SEQUENCE: 161

Met Gln Val Gln Leu Gln Gln Ser Gly Pro Glu Leu Val Lys Pro Gly
1               5                   10                  15

Ala Ser Val Lys Ile Ser Cys Lys Ala Ser Gly Tyr Thr Phe Thr Asp
            20                  25                  30

Asn Asn Met Asp Trp Val Lys Gln Ser His Gly Lys Gly Leu Glu Trp
        35                  40                  45

Ile Gly Asp Ile Asn Thr Lys Ser Gly Gly Ser Ile Tyr Asn Gln Lys
    50                  55                  60

Phe Lys Gly Lys Ala Thr Leu Thr Ile Asp Lys Ser Ser Ser Thr Ala
65                  70                  75                  80

Tyr Met Glu Leu Arg Ser Leu Thr Ser Glu Asp Thr Ala Val Tyr Tyr
                85                  90                  95

Cys Ala Arg Arg Arg Ser Tyr Gly Tyr Tyr Phe Asp Tyr Trp Gly Gln
            100                 105                 110

Gly Thr Thr Leu Thr Val Ser Ser
            115                 120

<210> SEQ ID NO 162
<211> LENGTH: 5
<212> TYPE: PRT
<213> ORGANISM: Mus musculus

<400> SEQUENCE: 162

Asp Asn Asn Met Asp
1               5

<210> SEQ ID NO 163
<211> LENGTH: 17
<212> TYPE: PRT
<213> ORGANISM: Mus musculus

<400> SEQUENCE: 163

Asp Ile Asn Thr Lys Ser Gly Gly Ser Ile Tyr Asn Gln Lys Phe Lys
1               5                   10                  15

Gly

<210> SEQ ID NO 164
<211> LENGTH: 10
<212> TYPE: PRT
<213> ORGANISM: Mus musculus

<400> SEQUENCE: 164

Arg Arg Ser Tyr Gly Tyr Tyr Phe Asp Tyr
1               5                   10

<210> SEQ ID NO 165
<211> LENGTH: 120
<212> TYPE: PRT
<213> ORGANISM: Mus musculus

<400> SEQUENCE: 165

Met Gln Val Gln Leu Lys Gln Ser Gly Ala Glu Leu Val Thr Pro Gly
1               5                   10                  15

Thr Ser Val Lys Ile Ser Cys Lys Ala Ser Gly Tyr Thr Phe Thr Asp
            20                  25                  30

Asn Asn Met Asp Trp Val Lys Gln Ser His Gly Lys Ser Leu Glu Trp
        35                  40                  45

Ile Gly Asp Ile Asn Pro Asn Tyr Asp Ser Thr Ala Tyr Asn Gln Lys
    50                  55                  60

```
Phe Lys Gly Lys Ala Thr Leu Thr Val Asp Lys Ser Ser Ser Thr Ala
 65                  70                  75                  80

Tyr Met Glu Leu Arg Ser Leu Thr Ser Glu Asp Thr Ala Val Tyr Tyr
                 85                  90                  95

Cys Ala Arg Arg Val Arg Arg Gly Tyr His Phe Asp Tyr Trp Gly Gln
            100                 105                 110

Gly Thr Thr Leu Thr Val Ser Ser
            115                 120

<210> SEQ ID NO 166
<211> LENGTH: 5
<212> TYPE: PRT
<213> ORGANISM: Mus musculus

<400> SEQUENCE: 166

Asp Asn Asn Met Asp
1               5

<210> SEQ ID NO 167
<211> LENGTH: 17
<212> TYPE: PRT
<213> ORGANISM: Mus musculus

<400> SEQUENCE: 167

Asp Ile Asn Pro Asn Tyr Asp Ser Thr Ala Tyr Asn Gln Lys Phe Lys
1               5                  10                  15

Gly

<210> SEQ ID NO 168
<211> LENGTH: 10
<212> TYPE: PRT
<213> ORGANISM: Mus musculus

<400> SEQUENCE: 168

Arg Val Arg Arg Gly Tyr His Phe Asp Tyr
1               5                  10

<210> SEQ ID NO 169
<211> LENGTH: 122
<212> TYPE: PRT
<213> ORGANISM: Mus musculus

<400> SEQUENCE: 169

Met Glu Val Gln Leu Gln Gln Ser Arg Pro Glu Leu Val Lys Pro Gly
1               5                  10                  15

Ala Ser Val Lys Ile Ser Cys Lys Thr Ser Gly Tyr Thr Phe Thr Glu
            20                  25                  30

Asn Ala Leu Tyr Trp Val Lys Gln Ser His Gly Lys Ser Leu Glu Trp
        35                  40                  45

Ile Gly Ile Ile Asn Pro Asn Ser Gly Gly Thr Asn Tyr Asn Gln Lys
    50                  55                  60

Phe Lys Asp Lys Ala Thr Leu Thr Val Asp Lys Ser Ser Ser Thr Ala
 65                  70                  75                  80

Tyr Met Glu Leu Arg Ser Leu Thr Ser Glu Asp Ser Ala Val Tyr Tyr
                 85                  90                  95

Cys Ala Arg Ser Gly Gly Arg Gly Gln Pro Tyr Tyr Phe Asp Tyr Trp
            100                 105                 110

Gly Gln Gly Thr Thr Leu Thr Val Ser Ser
            115                 120
```

```
<210> SEQ ID NO 170
<211> LENGTH: 5
<212> TYPE: PRT
<213> ORGANISM: Mus musculus

<400> SEQUENCE: 170

Glu Asn Ala Leu Tyr
1               5

<210> SEQ ID NO 171
<211> LENGTH: 17
<212> TYPE: PRT
<213> ORGANISM: Mus musculus

<400> SEQUENCE: 171

Ile Ile Asn Pro Asn Ser Gly Gly Thr Asn Tyr Asn Gln Lys Phe Lys
1               5                   10                  15

Asp

<210> SEQ ID NO 172
<211> LENGTH: 12
<212> TYPE: PRT
<213> ORGANISM: Mus musculus

<400> SEQUENCE: 172

Ser Gly Gly Arg Gly Gln Pro Tyr Tyr Phe Asp Tyr
1               5                   10

<210> SEQ ID NO 173
<211> LENGTH: 118
<212> TYPE: PRT
<213> ORGANISM: Mus musculus

<400> SEQUENCE: 173

Met Gln Val Gln Leu Gln Gln Ser Gly Ala Glu Leu Ala Arg Pro Gly
1               5                   10                  15

Ala Ser Val Lys Leu Ser Cys Lys Ala Ser Gly Tyr Thr Phe Thr Ser
                20                  25                  30

Tyr Trp Met Gln Trp Val Lys Gln Arg Pro Gly Gln Gly Leu Glu Trp
            35                  40                  45

Ile Gly Ala Ile Tyr Pro Gly Asp Gly Asp Thr Arg Tyr Thr Gln Lys
        50                  55                  60

Phe Lys Gly Lys Ala Thr Leu Thr Ala Asp Lys Ser Ser Ser Thr Ala
65                  70                  75                  80

Tyr Met His Leu Ser Ser Leu Ala Ser Glu Asp Ser Ala Val Tyr Tyr
                85                  90                  95

Cys Ala Arg Asp Gly Tyr Asp Leu Phe Ala Tyr Trp Gly Gln Gly Thr
            100                 105                 110

Leu Val Thr Val Ser Ala
        115

<210> SEQ ID NO 174
<211> LENGTH: 5
<212> TYPE: PRT
<213> ORGANISM: Mus musculus

<400> SEQUENCE: 174

Ser Tyr Trp Met Gln
1               5

<210> SEQ ID NO 175
```

```
<211> LENGTH: 17
<212> TYPE: PRT
<213> ORGANISM: Mus musculus

<400> SEQUENCE: 175

Ala Ile Tyr Pro Gly Asp Gly Asp Thr Arg Tyr Thr Gln Lys Phe Lys
1               5                   10                  15

Gly

<210> SEQ ID NO 176
<211> LENGTH: 8
<212> TYPE: PRT
<213> ORGANISM: Mus musculus

<400> SEQUENCE: 176

Asp Gly Tyr Asp Leu Phe Ala Tyr
1               5

<210> SEQ ID NO 177
<211> LENGTH: 118
<212> TYPE: PRT
<213> ORGANISM: Mus musculus

<400> SEQUENCE: 177

Met Glu Val Gln Leu Gln Gln Ser Gly Ala Glu Leu Ala Arg Pro Gly
1               5                   10                  15

Ala Ser Val Lys Leu Ser Cys Lys Ala Ser Gly Tyr Thr Phe Thr Asn
                20                  25                  30

Tyr Trp Met Gln Trp Val Lys Gln Arg Pro Gly Gln Gly Leu Glu Trp
            35                  40                  45

Ile Gly Ala Ile Tyr Pro Gly Asp Gly Asp Ile Arg Ile Thr Gln Lys
        50                  55                  60

Phe Arg Gly Lys Ala Thr Leu Thr Ala Asp Lys Ser Ser Ser Thr Ala
65                  70                  75                  80

Tyr Met Gln Leu Ser Ser Leu Ala Ser Glu Asp Ser Ala Val Tyr Tyr
                85                  90                  95

Cys Ala Arg Asp Gly Tyr Asp Leu Phe Ala Tyr Trp Gly Gln Gly Thr
            100                 105                 110

Leu Val Thr Val Ser Ala
        115

<210> SEQ ID NO 178
<211> LENGTH: 5
<212> TYPE: PRT
<213> ORGANISM: Mus musculus

<400> SEQUENCE: 178

Asn Tyr Trp Met Gln
1               5

<210> SEQ ID NO 179
<211> LENGTH: 17
<212> TYPE: PRT
<213> ORGANISM: Mus musculus

<400> SEQUENCE: 179

Ala Ile Tyr Pro Gly Asp Gly Asp Ile Arg Ile Thr Gln Lys Phe Arg
1               5                   10                  15

Gly

<210> SEQ ID NO 180
```

```
<211> LENGTH: 8
<212> TYPE: PRT
<213> ORGANISM: Mus musculus

<400> SEQUENCE: 180

Asp Gly Tyr Asp Leu Phe Ala Tyr
1               5

<210> SEQ ID NO 181
<211> LENGTH: 117
<212> TYPE: PRT
<213> ORGANISM: Mus musculus

<400> SEQUENCE: 181

Met Asp Val Gln Leu Val Glu Ser Gly Pro Gly Leu Val Lys Pro Ser
1               5                   10                  15

Gln Ser Leu Ser Leu Thr Cys Ser Val Thr Gly Tyr Ser Ile Thr Ser
            20                  25                  30

Gly Tyr Tyr Leu Asn Trp Ile Arg Gln Phe Pro Gly His Lys Leu Glu
        35                  40                  45

Trp Met Gly Tyr Ile Ser Tyr Asp Gly Asn Asn Arg Tyr Asn Pro Ser
    50                  55                  60

Leu Lys Asn Arg Ile Ser Ile Thr Arg Asp Thr Ser Lys Asn Gln Phe
65                  70                  75                  80

Phe Leu Lys Leu Asn Ser Val Thr Thr Glu Asp Thr Ala Thr Tyr Tyr
                85                  90                  95

Cys Ala Ser Phe Phe Tyr Gly Lys His Asp Trp Gly Gln Gly Thr Thr
            100                 105                 110

Leu Thr Val Ser Ser
        115

<210> SEQ ID NO 182
<211> LENGTH: 6
<212> TYPE: PRT
<213> ORGANISM: Mus musculus

<400> SEQUENCE: 182

Ser Gly Tyr Tyr Leu Asn
1               5

<210> SEQ ID NO 183
<211> LENGTH: 16
<212> TYPE: PRT
<213> ORGANISM: Mus musculus

<400> SEQUENCE: 183

Tyr Ile Ser Tyr Asp Gly Asn Asn Arg Tyr Asn Pro Ser Leu Lys Asn
1               5                   10                  15

<210> SEQ ID NO 184
<211> LENGTH: 7
<212> TYPE: PRT
<213> ORGANISM: Mus musculus

<400> SEQUENCE: 184

Phe Phe Tyr Gly Lys His Asp
1               5

<210> SEQ ID NO 185
<211> LENGTH: 115
<212> TYPE: PRT
<213> ORGANISM: Mus musculus
```

-continued

<400> SEQUENCE: 185

Met Glu Val Gln Leu Gln Gln Ser Gly Pro Glu Leu Val Lys Pro Gly
1               5                   10                  15

Ala Ser Val Lys Ile Ser Cys Lys Ala Ser Gly Tyr Ala Phe Ser Arg
            20                  25                  30

Ser Trp Met Asn Trp Val Lys Gln Arg Pro Gly Gln Gly Leu Glu Trp
        35                  40                  45

Ile Gly Trp Ile Tyr Pro Gly Asp Gly Ser Thr Lys Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Gly Gly Leu Asp Tyr Trp Gly Gln Gly Thr Thr Leu Thr
            100                 105                 110

Val Ser Ser
        115

<210> SEQ ID NO 186
<211> LENGTH: 5
<212> TYPE: PRT
<213> ORGANISM: Mus musculus

<400> SEQUENCE: 186

Arg Ser Trp Met Asn
1               5

<210> SEQ ID NO 187
<211> LENGTH: 17
<212> TYPE: PRT
<213> ORGANISM: Mus musculus

<400> SEQUENCE: 187

Trp Ile Tyr Pro Gly Asp Gly Ser Thr Lys Tyr Asn Glu Lys Phe Lys
1               5                   10                  15

Gly

<210> SEQ ID NO 188
<211> LENGTH: 5
<212> TYPE: PRT
<213> ORGANISM: Mus musculus

<400> SEQUENCE: 188

Gly Gly Leu Asp Tyr
1               5

<210> SEQ ID NO 189
<211> LENGTH: 119
<212> TYPE: PRT
<213> ORGANISM: Mus musculus

<400> SEQUENCE: 189

Met Gln Val Gln Leu Gln Gln Ser Gly Ala Glu Leu Val Arg Pro Gly
1               5                   10                  15

Ser Ser Val Lys Ile Ser Cys Lys Ala Ser Gly Tyr Ala Phe Ser Arg
            20                  25                  30

Tyr Trp Met Asn Trp Val Lys Gln Arg Pro Gly Gln Gly Leu Glu Trp
        35                  40                  45

Ile Gly Gln Ile Tyr Pro Gly Asp Gly Asp Thr Asn Tyr Asn Gly Lys
    50                  55                  60

```
Phe Lys Gly Lys Ala Thr Leu Thr Ala Asp Lys Ser Ser Ser Thr Ala
 65                  70                  75                  80

Tyr Met Gln Leu Ser Ser Leu Ala Ser Glu Asp Ser Ala Val Tyr Phe
                 85                  90                  95

Cys Ala Arg Gly Arg Gly Tyr Ser Ala Met Asp Tyr Trp Gly Gln Gly
            100                 105                 110

Thr Ser Val Thr Val Ser Ser
            115
```

<210> SEQ ID NO 190
<211> LENGTH: 5
<212> TYPE: PRT
<213> ORGANISM: Mus musculus

<400> SEQUENCE: 190

```
Arg Tyr Trp Met Asn
1               5
```

<210> SEQ ID NO 191
<211> LENGTH: 17
<212> TYPE: PRT
<213> ORGANISM: Mus musculus

<400> SEQUENCE: 191

```
Gln Ile Tyr Pro Gly Asp Gly Asp Thr Asn Tyr Asn Gly Lys Phe Lys
1               5                   10                  15

Gly
```

<210> SEQ ID NO 192
<211> LENGTH: 9
<212> TYPE: PRT
<213> ORGANISM: Mus musculus

<400> SEQUENCE: 192

```
Gly Arg Gly Tyr Ser Ala Met Asp Tyr
1               5
```

<210> SEQ ID NO 193
<211> LENGTH: 120
<212> TYPE: PRT
<213> ORGANISM: Mus musculus

<400> SEQUENCE: 193

```
Met Gln Val Gln Leu Gln Gln Ser Gly Pro Glu Leu Val Lys Pro Gly
1               5                   10                  15

Ala Ser Val Lys Ile Pro Cys Lys Ala Ser Gly Tyr Thr Phe Thr Asp
            20                  25                  30

Tyr Asn Met Asp Trp Val Lys Gln Ser His Gly Lys Ser Leu Glu Trp
        35                  40                  45

Ile Gly Asp Ile Asp Pro Asn Asn Gly Gly Ala Leu Tyr Asn Gln Lys
    50                  55                  60

Phe Lys Gly Lys Ala Thr Leu Thr Val Asp Lys Ser Ser Ser Thr Ala
 65                 70                  75                  80

Tyr Met Glu Leu Arg Ser Leu Thr Ser Glu Asp Thr Ala Val Tyr Tyr
                85                  90                  95

Cys Ala Arg Arg Pro Val Tyr Tyr Ala Met Asp Tyr Trp Gly Gln
            100                 105                 110

Gly Thr Ser Val Thr Val Ser Ser
            115                 120
```

```
<210> SEQ ID NO 194
<211> LENGTH: 5
<212> TYPE: PRT
<213> ORGANISM: Mus musculus

<400> SEQUENCE: 194

Asp Tyr Asn Met Asp
1               5

<210> SEQ ID NO 195
<211> LENGTH: 17
<212> TYPE: PRT
<213> ORGANISM: Mus musculus

<400> SEQUENCE: 195

Asp Ile Asp Pro Asn Asn Gly Gly Ala Leu Tyr Asn Gln Lys Phe Lys
1               5                   10                  15

Gly

<210> SEQ ID NO 196
<211> LENGTH: 10
<212> TYPE: PRT
<213> ORGANISM: Mus musculus

<400> SEQUENCE: 196

Arg Pro Val Tyr Tyr Tyr Ala Met Asp Tyr
1               5                   10

<210> SEQ ID NO 197
<211> LENGTH: 120
<212> TYPE: PRT
<213> ORGANISM: Mus musculus

<400> SEQUENCE: 197

Met His Val Gln Leu Gln Gln Ser Gly Pro Glu Leu Val Lys Pro Gly
1               5                   10                  15

Ala Ser Val Lys Ile Pro Cys Lys Ala Ser Gly Tyr Thr Phe Thr Asp
                20                  25                  30

Asn Asn Met Asp Trp Val Lys Gln Ser His Gly Lys Ser Leu Glu Trp
            35                  40                  45

Ile Gly Asp Ile Asn Pro Asn Asn Gly Gly Thr Ile Tyr Asn Gln Lys
        50                  55                  60

Phe Lys Gly Lys Ala Thr Leu Thr Val Asp Lys Ser Ser Ser Thr Ala
65                  70                  75                  80

Tyr Met Glu Leu Arg Ser Leu Thr Ser Glu Asp Thr Ala Val Tyr Tyr
                85                  90                  95

Cys Ala Arg Arg Gly Tyr Tyr Gly Arg Thr Phe Asp Tyr Trp Gly Gln
            100                 105                 110

Gly Thr Thr Leu Thr Val Ser Ser
        115                 120

<210> SEQ ID NO 198
<211> LENGTH: 5
<212> TYPE: PRT
<213> ORGANISM: Mus musculus

<400> SEQUENCE: 198

Asp Asn Asn Met Asp
1               5

<210> SEQ ID NO 199
```

<211> LENGTH: 17
<212> TYPE: PRT
<213> ORGANISM: Mus musculus

<400> SEQUENCE: 199

Asp Ile Asn Pro Asn Asn Gly Gly Thr Ile Tyr Asn Gln Lys Phe Lys
1               5                   10                  15

Gly

<210> SEQ ID NO 200
<211> LENGTH: 10
<212> TYPE: PRT
<213> ORGANISM: Mus musculus

<400> SEQUENCE: 200

Arg Gly Tyr Tyr Gly Arg Thr Phe Asp Tyr
1               5                   10

<210> SEQ ID NO 201
<211> LENGTH: 117
<212> TYPE: PRT
<213> ORGANISM: Mus musculus

<400> SEQUENCE: 201

Met Gln Val Gln Leu Gln Gln Ser Gly Ala Glu Leu Val Arg Pro Gly
1               5                   10                  15

Ala Ser Val Lys Leu Ser Cys Thr Ala Ser Gly Phe Asn Ile Lys Asp
            20                  25                  30

Asp Tyr Met His Trp Val Asn Gln Arg Pro Glu Gln Gly Leu Glu Trp
        35                  40                  45

Ile Gly Trp Ile Asp Pro Glu Asn Gly Asp Thr Glu Tyr Ala Ser Lys
    50                  55                  60

Phe Gln Gly Lys Ala Thr Ile Thr Ala Asp Thr Ser Ser Asn Thr Ala
65                  70                  75                  80

Tyr Leu Gln Leu Ser Ser Leu Thr Ser Glu Asp Thr Ala Val Tyr Tyr
                85                  90                  95

Cys Thr Tyr Gly Ile Tyr Val Arg Gly Tyr Trp Gly Gln Gly Thr Thr
            100                 105                 110

Leu Thr Val Ser Ser
        115

<210> SEQ ID NO 202
<211> LENGTH: 5
<212> TYPE: PRT
<213> ORGANISM: Mus musculus

<400> SEQUENCE: 202

Asp Asp Tyr Met His
1               5

<210> SEQ ID NO 203
<211> LENGTH: 17
<212> TYPE: PRT
<213> ORGANISM: Mus musculus

<400> SEQUENCE: 203

Trp Ile Asp Pro Glu Asn Gly Asp Thr Glu Tyr Ala Ser Lys Phe Gln
1               5                   10                  15

Gly

<210> SEQ ID NO 204

```
<211> LENGTH: 7
<212> TYPE: PRT
<213> ORGANISM: Mus musculus

<400> SEQUENCE: 204

Gly Ile Tyr Val Arg Gly Tyr
1               5

<210> SEQ ID NO 205
<211> LENGTH: 107
<212> TYPE: PRT
<213> ORGANISM: Mus musculus

<400> SEQUENCE: 205

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Arg Tyr Gly Thr Asp Phe Thr Leu Thr Ile Ser Asn Val Gln Ser
65                  70                  75                  80

Glu Asp Leu Ala Asp Tyr Leu Cys Gln Gln Tyr Ser Asn Tyr Ile Thr
                85                  90                  95

Phe Gly Gly Gly Thr Lys Leu Glu Leu Lys Arg
            100                 105

<210> SEQ ID NO 206
<211> LENGTH: 11
<212> TYPE: PRT
<213> ORGANISM: Mus musculus

<400> SEQUENCE: 206

Lys Ala Ser Gln Asp Val Gly Thr Ala Val Ala
1               5                   10

<210> SEQ ID NO 207
<211> LENGTH: 7
<212> TYPE: PRT
<213> ORGANISM: Mus musculus

<400> SEQUENCE: 207

Trp Ala Ser Thr Arg His Thr
1               5

<210> SEQ ID NO 208
<211> LENGTH: 8
<212> TYPE: PRT
<213> ORGANISM: Mus musculus

<400> SEQUENCE: 208

Gln Gln Tyr Ser Asn Tyr Ile Thr
1               5

<210> SEQ ID NO 209
<211> LENGTH: 108
<212> TYPE: PRT
<213> ORGANISM: Mus musculus

<400> SEQUENCE: 209

Asp Ile Val Leu Thr Gln Ser Gln Lys Phe Met Ser Thr Ser Val Gly
```

```
                1               5                   10                  15
Asp Arg Val Ser Ile Thr Cys Lys Ala Ser Gln Asn Val Gly Thr Ala
                        20                  25                  30

Val Ala Trp Tyr Gln Gln Lys Pro Gly Gln Ser Pro Lys Ala Leu Ile
                35                  40                  45

Tyr Ser Ala Ser Tyr Arg Tyr Ser Gly Val Pro Asp Arg Phe Thr Gly
            50                  55                  60

Ser Gly Ser Gly Thr Asp Phe Thr Leu Thr Ile Ser Asn Val Gln Ser
65                      70                  75                  80

Glu Asp Leu Ala Glu Tyr Phe Cys Gln Gln Tyr Asn Ser Tyr Pro Leu
                        85                  90                  95

Thr Phe Gly Ala Gly Thr Lys Leu Glu Ile Lys Arg
                100                 105

<210> SEQ ID NO 210
<211> LENGTH: 11
<212> TYPE: PRT
<213> ORGANISM: Mus musculus

<400> SEQUENCE: 210

Lys Ala Ser Gln Asn Val Gly Thr Ala Val Ala
1               5                   10

<210> SEQ ID NO 211
<211> LENGTH: 7
<212> TYPE: PRT
<213> ORGANISM: Mus musculus

<400> SEQUENCE: 211

Ser Ala Ser Tyr Arg Tyr Ser
1               5

<210> SEQ ID NO 212
<211> LENGTH: 9
<212> TYPE: PRT
<213> ORGANISM: Mus musculus

<400> SEQUENCE: 212

Gln Gln Tyr Asn Ser Tyr Pro Leu Thr
1               5

<210> SEQ ID NO 213
<211> LENGTH: 107
<212> TYPE: PRT
<213> ORGANISM: Mus musculus

<400> SEQUENCE: 213

Asp Ile Val Leu Thr Gln Ser Pro Ala Ile Met Ser Ala Ser Leu Gly
1               5                   10                  15

Glu Lys Val Thr Met Ser Cys Arg Ala Thr Ser Ser Val Asn Tyr Ile
                        20                  25                  30

Tyr Trp Tyr Gln Gln Lys Ser Asp Ala Ser Pro Lys Leu Trp Ile Phe
                35                  40                  45

Tyr Thr Ser Asn Leu Ala Pro Gly Val Pro Pro Arg Phe Ser Gly Ser
            50                  55                  60

Gly Ser Gly Asn Ser Tyr Ser Leu Thr Ile Ser Ser Met Glu Ala Glu
65                      70                  75                  80

Asp Ala Ala Thr Tyr Tyr Cys Gln Gln Phe Ser Ser Ser Pro Trp Thr
                        85                  90                  95

Phe Gly Gly Gly Thr Lys Leu Glu Ile Lys Arg
```

-continued

<210> SEQ ID NO 214
<211> LENGTH: 10
<212> TYPE: PRT
<213> ORGANISM: Mus musculus

<400> SEQUENCE: 214

Arg Ala Thr Ser Ser Val Asn Tyr Ile Tyr
1               5                   10

<210> SEQ ID NO 215
<211> LENGTH: 6
<212> TYPE: PRT
<213> ORGANISM: Mus musculus

<400> SEQUENCE: 215

Thr Ser Asn Leu Ala Pro
1               5

<210> SEQ ID NO 216
<211> LENGTH: 9
<212> TYPE: PRT
<213> ORGANISM: Mus musculus

<400> SEQUENCE: 216

Gln Gln Phe Ser Ser Ser Pro Trp Thr
1               5

<210> SEQ ID NO 217
<211> LENGTH: 114
<212> TYPE: PRT
<213> ORGANISM: Mus musculus

<400> SEQUENCE: 217

Asp Ile Val Met Thr Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Leu Cys Gln Gln
                85                  90                  95

Tyr Tyr Arg Phe Pro Tyr Thr Phe Gly Gly Gly Thr Lys Leu Glu Ile
            100                 105                 110

Lys Arg

<210> SEQ ID NO 218
<211> LENGTH: 17
<212> TYPE: PRT
<213> ORGANISM: Mus musculus

<400> SEQUENCE: 218

Lys Ser Ser Gln Ser Leu Leu Tyr Ser Ser Asn Gln Lys Asn Tyr Leu
1               5                   10                  15

Ala

```
<210> SEQ ID NO 219
<211> LENGTH: 7
<212> TYPE: PRT
<213> ORGANISM: Mus musculus

<400> SEQUENCE: 219

Trp Ala Ser Thr Arg Glu Ser
1               5

<210> SEQ ID NO 220
<211> LENGTH: 9
<212> TYPE: PRT
<213> ORGANISM: Mus musculus

<400> SEQUENCE: 220

Gln Gln Tyr Tyr Arg Phe Pro Tyr Thr
1               5

<210> SEQ ID NO 221
<211> LENGTH: 18
<212> TYPE: DNA
<213> ORGANISM: Mus musculus
<220> FEATURE:
<221> NAME/KEY: CDS
<222> LOCATION: (1)..(18)
<223> OTHER INFORMATION:

<400> SEQUENCE: 221 agt ggt tat tac tgg acc                                              18
Ser Gly Tyr Tyr Trp Thr
1               5

<210> SEQ ID NO 222
<211> LENGTH: 6
<212> TYPE: PRT
<213> ORGANISM: Mus musculus

<400> SEQUENCE: 222

Ser Gly Tyr Tyr Trp Thr
1               5

<210> SEQ ID NO 223
<211> LENGTH: 48
<212> TYPE: DNA
<213> ORGANISM: Mus musculus
<220> FEATURE:
<221> NAME/KEY: CDS
<222> LOCATION: (1)..(48)
<223> OTHER INFORMATION:

<400> SEQUENCE: 223 tac ata tcc ttc gac ggt acc aat gac tac aac cca tct ctc aaa aat     48
Tyr Ile Ser Phe Asp Gly Thr Asn Asp Tyr Asn Pro Ser Leu Lys Asn
1               5                   10                  15

<210> SEQ ID NO 224
<211> LENGTH: 16
<212> TYPE: PRT
<213> ORGANISM: Mus musculus

<400> SEQUENCE: 224

Tyr Ile Ser Phe Asp Gly Thr Asn Asp Tyr Asn Pro Ser Leu Lys Asn
1               5                   10                  15

<210> SEQ ID NO 225
<211> LENGTH: 18
<212> TYPE: DNA
<213> ORGANISM: Mus musculus
```

```
<220> FEATURE:
<221> NAME/KEY: CDS
<222> LOCATION: (1)..(18)
<223> OTHER INFORMATION:

<400> SEQUENCE: 225 ggc ccc ccc tgt act tac                                          18
Gly Pro Pro Cys Thr Tyr
1               5

<210> SEQ ID NO 226
<211> LENGTH: 6
<212> TYPE: PRT
<213> ORGANISM: Mus musculus

<400> SEQUENCE: 226

Gly Pro Pro Cys Thr Tyr
1               5

<210> SEQ ID NO 227
<211> LENGTH: 30
<212> TYPE: DNA
<213> ORGANISM: Mus musculus
<220> FEATURE:
<221> NAME/KEY: CDS
<222> LOCATION: (1)..(30)
<223> OTHER INFORMATION:

<400> SEQUENCE: 227 agg gcc acc tca agt gta aat tac att tac                          30
Arg Ala Thr Ser Ser Val Asn Tyr Ile Tyr
1               5                   10

<210> SEQ ID NO 228
<211> LENGTH: 10
<212> TYPE: PRT
<213> ORGANISM: Mus musculus

<400> SEQUENCE: 228

Arg Ala Thr Ser Ser Val Asn Tyr Ile Tyr
1               5                   10

<210> SEQ ID NO 229
<211> LENGTH: 18
<212> TYPE: DNA
<213> ORGANISM: Mus musculus
<220> FEATURE:
<221> NAME/KEY: CDS
<222> LOCATION: (1)..(18)
<223> OTHER INFORMATION:

<400> SEQUENCE: 229 aca tcc aac ctg gct cct                                          18
Thr Ser Asn Leu Ala Pro
1               5

<210> SEQ ID NO 230
<211> LENGTH: 6
<212> TYPE: PRT
<213> ORGANISM: Mus musculus

<400> SEQUENCE: 230

Thr Ser Asn Leu Ala Pro
1               5

<210> SEQ ID NO 231
<211> LENGTH: 27
<212> TYPE: DNA
```

```
<213> ORGANISM: Mus musculus
<220> FEATURE:
<221> NAME/KEY: CDS
<222> LOCATION: (1)..(27)
<223> OTHER INFORMATION:

<400> SEQUENCE: 231 cag cag ttt tct agt tcc cca tgg acg                                    27
Gln Gln Phe Ser Ser Ser Pro Trp Thr
1               5

<210> SEQ ID NO 232
<211> LENGTH: 9
<212> TYPE: PRT
<213> ORGANISM: Mus musculus

<400> SEQUENCE: 232

Gln Gln Phe Ser Ser Ser Pro Trp Thr
1               5

<210> SEQ ID NO 233
<211> LENGTH: 15
<212> TYPE: DNA
<213> ORGANISM: Mus musculus
<220> FEATURE:
<221> NAME/KEY: CDS
<222> LOCATION: (1)..(15)
<223> OTHER INFORMATION:

<400> SEQUENCE: 233 cac ttt gtt ttg cac                                                    15
His Phe Val Leu His
1               5

<210> SEQ ID NO 234
<211> LENGTH: 5
<212> TYPE: PRT
<213> ORGANISM: Mus musculus

<400> SEQUENCE: 234

His Phe Val Leu His
1               5

<210> SEQ ID NO 235
<211> LENGTH: 48
<212> TYPE: DNA
<213> ORGANISM: Mus musculus
<220> FEATURE:
<221> NAME/KEY: CDS
<222> LOCATION: (1)..(48)
<223> OTHER INFORMATION:

<400> SEQUENCE: 235 tat att att cct tac aat gat ggt act aag tac aat gag aag ttc aaa        48
Tyr Ile Ile Pro Tyr Asn Asp Gly Thr Lys Tyr Asn Glu Lys Phe Lys
1               5                   10                  15

<210> SEQ ID NO 236
<211> LENGTH: 16
<212> TYPE: PRT
<213> ORGANISM: Mus musculus

<400> SEQUENCE: 236

Tyr Ile Ile Pro Tyr Asn Asp Gly Thr Lys Tyr Asn Glu Lys Phe Lys
1               5                   10                  15

<210> SEQ ID NO 237
<211> LENGTH: 39
```

<212> TYPE: DNA
<213> ORGANISM: Mus musculus
<220> FEATURE:
<221> NAME/KEY: CDS
<222> LOCATION: (1)..(39)
<223> OTHER INFORMATION:

<400> SEQUENCE: 237

```
ggg aat agg tac gac gta ggt tcc tat gct atg gac tac        39
Gly Asn Arg Tyr Asp Val Gly Ser Tyr Ala Met Asp Tyr
1               5                   10
```

<210> SEQ ID NO 238
<211> LENGTH: 13
<212> TYPE: PRT
<213> ORGANISM: Mus musculus

<400> SEQUENCE: 238

```
Gly Asn Arg Tyr Asp Val Gly Ser Tyr Ala Met Asp Tyr
1               5                   10
```

<210> SEQ ID NO 239
<211> LENGTH: 51
<212> TYPE: DNA
<213> ORGANISM: Mus musculus
<220> FEATURE:
<221> NAME/KEY: CDS
<222> LOCATION: (1)..(51)
<223> OTHER INFORMATION:

<400> SEQUENCE: 239

```
aag tcc agt cag agc ctt tta tat agt agc aat caa aag aac tac ttg    48
Lys Ser Ser Gln Ser Leu Leu Tyr Ser Ser Asn Gln Lys Asn Tyr Leu
1               5                   10                  15 gcc                                                                 51
Ala
```

<210> SEQ ID NO 240
<211> LENGTH: 17
<212> TYPE: PRT
<213> ORGANISM: Mus musculus

<400> SEQUENCE: 240

```
Lys Ser Ser Gln Ser Leu Leu Tyr Ser Ser Asn Gln Lys Asn Tyr Leu
1               5                   10                  15

Ala
```

<210> SEQ ID NO 241
<211> LENGTH: 21
<212> TYPE: DNA
<213> ORGANISM: Mus musculus
<220> FEATURE:
<221> NAME/KEY: CDS
<222> LOCATION: (1)..(21)
<223> OTHER INFORMATION:

<400> SEQUENCE: 241

```
tgg gca tcc act agg gaa tct                                21
Trp Ala Ser Thr Arg Glu Ser
1               5
```

<210> SEQ ID NO 242
<211> LENGTH: 7
<212> TYPE: PRT
<213> ORGANISM: Mus musculus

<400> SEQUENCE: 242

Trp Ala Ser Thr Arg Glu Ser
1               5

<210> SEQ ID NO 243
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION:

<400> SEQUENCE: 243 cag caa tat tat agg ttt ccg tac acg                     27
Gln Gln Tyr Tyr Arg Phe Pro Tyr Thr
1               5

<210> SEQ ID NO 244
<211> LENGTH: 9
<212> TYPE: PRT
<213> ORGANISM: Mus musculus

<400> SEQUENCE: 244

Gln Gln Tyr Tyr Arg Phe Pro Tyr Thr
1               5

<210> SEQ ID NO 245
<211> LENGTH: 15
<212> TYPE: DNA
<213> ORGANISM: Mus musculus
<220> FEATURE:
<221> NAME/KEY: CDS
<222> LOCATION: (1)..(15)
<223> OTHER INFORMATION:

<400> SEQUENCE: 245 agc tcc tgg atg cac                                     15
Ser Ser Trp Met His
1               5

<210> SEQ ID NO 246
<211> LENGTH: 5
<212> TYPE: PRT
<213> ORGANISM: Mus musculus

<400> SEQUENCE: 246

Ser Ser Trp Met His
1               5

<210> SEQ ID NO 247
<211> LENGTH: 51
<212> TYPE: DNA
<213> ORGANISM: Mus musculus
<220> FEATURE:
<221> NAME/KEY: CDS
<222> LOCATION: (1)..(51)
<223> OTHER INFORMATION:

<400> SEQUENCE: 247 tac att aat cct agc agt ggt tat act aag tac aat cgg aag ttc agg    48
Tyr Ile Asn Pro Ser Ser Gly Tyr Thr Lys Tyr Asn Arg Lys Phe Arg
1               5                   10                  15 gac                                                                51
Asp

<210> SEQ ID NO 248
<211> LENGTH: 17
<212> TYPE: PRT

<213> ORGANISM: Mus musculus

<400> SEQUENCE: 248

Tyr Ile Asn Pro Ser Ser Gly Tyr Thr Lys Tyr Asn Arg Lys Phe Arg
1               5                   10                  15

Asp

<210> SEQ ID NO 249
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION:

<400> SEQUENCE: 249 ggg ggt aac ggt tac tac ttt gac tac                         27
Gly Gly Asn Gly Tyr Tyr Phe Asp Tyr
1               5

<210> SEQ ID NO 250
<211> LENGTH: 9
<212> TYPE: PRT
<213> ORGANISM: Mus musculus

<400> SEQUENCE: 250

Gly Gly Asn Gly Tyr Tyr Phe Asp Tyr
1               5

<210> SEQ ID NO 251
<211> LENGTH: 33
<212> TYPE: DNA
<213> ORGANISM: Mus musculus
<220> FEATURE:
<221> NAME/KEY: CDS
<222> LOCATION: (1)..(33)
<223> OTHER INFORMATION:

<400> SEQUENCE: 251 aag gcc agt cag gat gtg ggg act gct gta gcc                 33
Lys Ala Ser Gln Asp Val Gly Thr Ala Val Ala
1               5                   10

<210> SEQ ID NO 252
<211> LENGTH: 11
<212> TYPE: PRT
<213> ORGANISM: Mus musculus

<400> SEQUENCE: 252

Lys Ala Ser Gln Asp Val Gly Thr Ala Val Ala
1               5                   10

<210> SEQ ID NO 253
<211> LENGTH: 21
<212> TYPE: DNA
<213> ORGANISM: Mus musculus
<220> FEATURE:
<221> NAME/KEY: CDS
<222> LOCATION: (1)..(21)
<223> OTHER INFORMATION:

<400> SEQUENCE: 253 tgg gca tcc acc cgg cac act                                 21
Trp Ala Ser Thr Arg His Thr
1               5

```
<210> SEQ ID NO 254
<211> LENGTH: 7
<212> TYPE: PRT
<213> ORGANISM: Mus musculus

<400> SEQUENCE: 254

Trp Ala Ser Thr Arg His Thr
1               5

<210> SEQ ID NO 255
<211> LENGTH: 24
<212> TYPE: DNA
<213> ORGANISM: Mus musculus
<220> FEATURE:
<221> NAME/KEY: CDS
<222> LOCATION: (1)..(24)
<223> OTHER INFORMATION:

<400> SEQUENCE: 255 cag caa tat agc aac tat atc acg                              24
Gln Gln Tyr Ser Asn Tyr Ile Thr
1               5

<210> SEQ ID NO 256
<211> LENGTH: 8
<212> TYPE: PRT
<213> ORGANISM: Mus musculus

<400> SEQUENCE: 256

Gln Gln Tyr Ser Asn Tyr Ile Thr
1               5

<210> SEQ ID NO 257
<211> LENGTH: 15
<212> TYPE: DNA
<213> ORGANISM: Mus musculus
<220> FEATURE:
<221> NAME/KEY: CDS
<222> LOCATION: (1)..(15)
<223> OTHER INFORMATION:

<400> SEQUENCE: 257 gac aac aac atg gac                                          15
Asp Asn Asn Met Asp
1               5

<210> SEQ ID NO 258
<211> LENGTH: 5
<212> TYPE: PRT
<213> ORGANISM: Mus musculus

<400> SEQUENCE: 258

Asp Asn Asn Met Asp
1               5

<210> SEQ ID NO 259
<211> LENGTH: 51
<212> TYPE: DNA
<213> ORGANISM: Mus musculus
<220> FEATURE:
<221> NAME/KEY: CDS
<222> LOCATION: (1)..(51)
<223> OTHER INFORMATION:

<400> SEQUENCE: 259 gat att aat act aaa agt ggt ggt tct atc tac aac cag aag ttc aag    48
Asp Ile Asn Thr Lys Ser Gly Gly Ser Ile Tyr Asn Gln Lys Phe Lys
1               5                   10                  15
```

```
ggc                                                              51
Gly

<210> SEQ ID NO 260
<211> LENGTH: 17
<212> TYPE: PRT
<213> ORGANISM: Mus musculus

<400> SEQUENCE: 260

Asp Ile Asn Thr Lys Ser Gly Gly Ser Ile Tyr Asn Gln Lys Phe Lys
1               5                   10                  15

Gly

<210> SEQ ID NO 261
<211> LENGTH: 30
<212> TYPE: DNA
<213> ORGANISM: Mus musculus
<220> FEATURE:
<221> NAME/KEY: CDS
<222> LOCATION: (1)..(30)
<223> OTHER INFORMATION:

<400> SEQUENCE: 261 agg agg agc tac ggc tac tac ttt gac tac                          30
Arg Arg Ser Tyr Gly Tyr Tyr Phe Asp Tyr
1               5                   10

<210> SEQ ID NO 262
<211> LENGTH: 10
<212> TYPE: PRT
<213> ORGANISM: Mus musculus

<400> SEQUENCE: 262

Arg Arg Ser Tyr Gly Tyr Tyr Phe Asp Tyr
1               5                   10

<210> SEQ ID NO 263
<211> LENGTH: 33
<212> TYPE: DNA
<213> ORGANISM: Mus musculus
<220> FEATURE:
<221> NAME/KEY: CDS
<222> LOCATION: (1)..(33)
<223> OTHER INFORMATION:

<400> SEQUENCE: 263 aag gcc agt cag aat gtg ggt act gct gta gcc                      33
Lys Ala Ser Gln Asn Val Gly Thr Ala Val Ala
1               5                   10

<210> SEQ ID NO 264
<211> LENGTH: 11
<212> TYPE: PRT
<213> ORGANISM: Mus musculus

<400> SEQUENCE: 264

Lys Ala Ser Gln Asn Val Gly Thr Ala Val Ala
1               5                   10

<210> SEQ ID NO 265
<211> LENGTH: 21
<212> TYPE: DNA
<213> ORGANISM: Mus musculus
<220> FEATURE:
<221> NAME/KEY: CDS
<222> LOCATION: (1)..(21)
<223> OTHER INFORMATION:
```

```
<400> SEQUENCE: 265 tcg gca tcc tac cgg tac agt                                    21
Ser Ala Ser Tyr Arg Tyr Ser
1               5

<210> SEQ ID NO 266
<211> LENGTH: 7
<212> TYPE: PRT
<213> ORGANISM: Mus musculus

<400> SEQUENCE: 266

Ser Ala Ser Tyr Arg Tyr Ser
1               5

<210> SEQ ID NO 267
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION:

<400> SEQUENCE: 267 cag caa tat aac agc tat cct ctc acg                            27
Gln Gln Tyr Asn Ser Tyr Pro Leu Thr
1               5

<210> SEQ ID NO 268
<211> LENGTH: 9
<212> TYPE: PRT
<213> ORGANISM: Mus musculus

<400> SEQUENCE: 268

Gln Gln Tyr Asn Ser Tyr Pro Leu Thr
1               5
```